(12) United States Patent
Baumert et al.

(10) Patent No.: US 8,518,408 B2
(45) Date of Patent: Aug. 27, 2013

(54) MONOCLONAL ANTI-CLAUDIN 1 ANTIBODIES FOR THE INHIBITION OF HEPATITIS C VIRUS INFECTION

(75) Inventors: Thomas Baumert, Strasbourg (FR); Catherine Schuster, Strasbourg (FR); John Thompson, Freiburg (DE); Fritz Grunert, Freiburg (DE)

(73) Assignees: INSERM (Institut National de la Sante et de la Recherche Medicale), Paris (FR); University de Strasbourg, Strasbourg (FR)

( * ) Notice: Subject to any disclaimer, the term of this patent is extended or adjusted under 35 U.S.C. 154(b) by 166 days.

(21) Appl. No.: 13/119,233

(22) PCT Filed: Sep. 25, 2009

(86) PCT No.: PCT/EP2009/062449
§ 371 (c)(1),
(2), (4) Date: Jun. 1, 2011

(87) PCT Pub. No.: WO2010/034812
PCT Pub. Date: Apr. 1, 2010

(65) Prior Publication Data
US 2011/0236347 A1   Sep. 29, 2011

(30) Foreign Application Priority Data
Sep. 25, 2008   (EP) .................................. 08305597

(51) Int. Cl.
*A61K 39/42*   (2006.01)
*C12N 5/12*    (2006.01)
*C12P 21/08*   (2006.01)

(52) U.S. Cl.
USPC .................. 424/149.1; 530/387.3; 530/388.1; 435/326

(58) Field of Classification Search
None
See application file for complete search history.

(56) References Cited

FOREIGN PATENT DOCUMENTS
EP   1167387   1/2002

OTHER PUBLICATIONS

Bretner, M. Existing and future therapeutic options for hepatitis C virus infection. Acta Biochimica Polonica 2005, vol. 52, No. 1, pp. 57-70.*
Leroux-Roels G. Development of prophylactic and therapeutic vaccines against hepatitis C virus. Expert Review in Vaccines 2005, vol. 4, No. 3, pp. 351-371.*
Perotti et al. Identification of a Broadly Cross-Reacting and Neutralizing Human Monoclonal Antibody Directed against the Hepatitis C Virus E2 Protein. Journal of Virology 2007, vol. 82(2), pp. 1047-1052.*
Eren et al. Preclinical evaluation of two neutralizing human monoclonal antibodies against hepatitis C virus. Journal of Virology 2006, vol. 80, No. 6, pp. 2654-2664.*
Burioni et al. Nonneutralizing Human Antibody Fragments against Hepatitis C Virus E2 Glycoproein Modulate Neutralization of Binding Activity of Human Recombinant Fabs. Virology 2001, vol. 288, Issue 1, pp. 29-35.*
Habersetzer et al. Characterization of Human Monoclonal Antibodies Specific to the Hepatitis C Virus Glycoprotein E2 with in Vitro Binding Neutralization Properties. Virology 1998, vol. 249, pp. 32-41.*

* cited by examiner

*Primary Examiner* — Louise Humphrey
(74) *Attorney, Agent, or Firm* — McAndrews Held & Malloy, Ltd.

(57) ABSTRACT

The present invention provides monoclonal antibodies that specifically bind to the extracellular domain of human Claudin-1 on the cell surface, thereby inhibiting HCV entry into susceptible cells and preventing HCV infection of these cells; and hybridoma cell lines which produce such monoclonal antibodies. Also provided are reagents that comprise such antibodies, and pharmaceutical compositions comprising such antibodies. Methods of treating or preventing HCV infection by administration of an inventive monoclonal antibody, or a pharmaceutical composition thereof are also described.

22 Claims, 34 Drawing Sheets

A
Huh 7.5
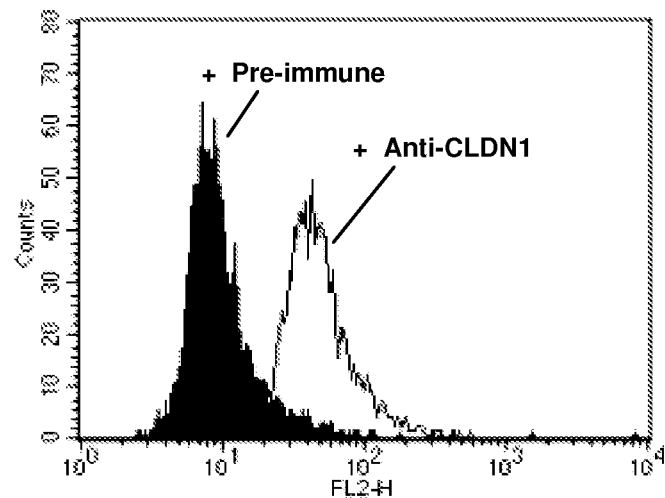
B
Human
Hepatocytes
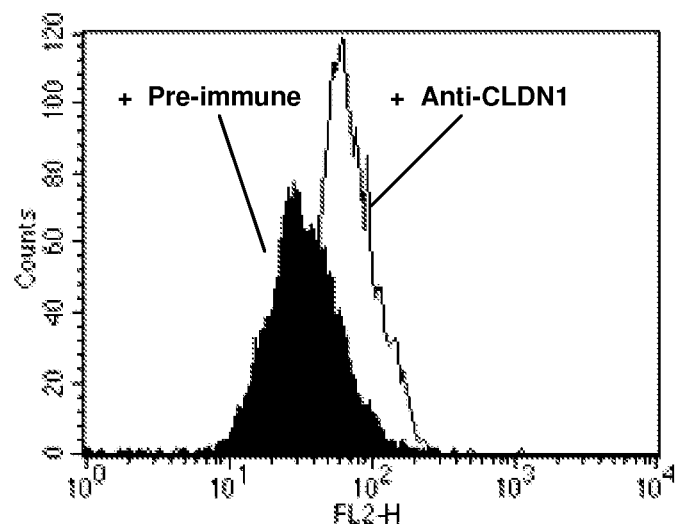
Figure 2

A
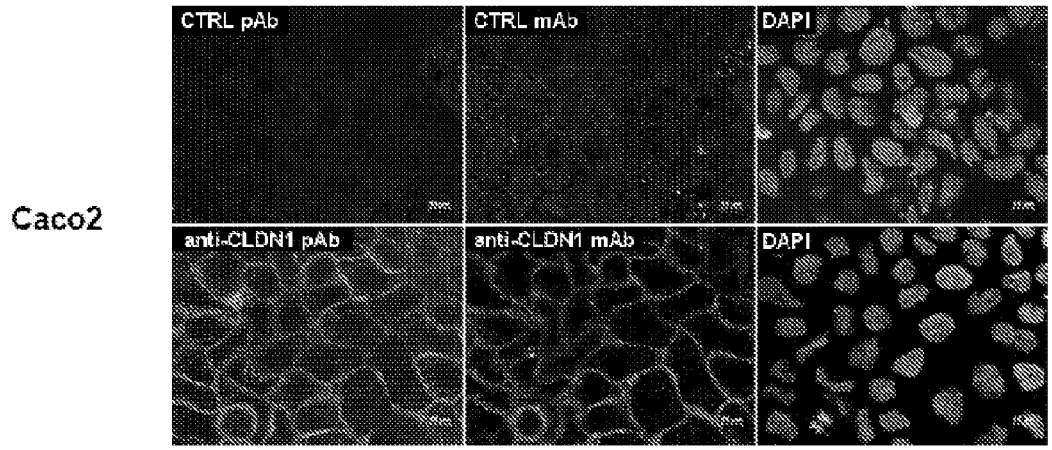
Caco2
B
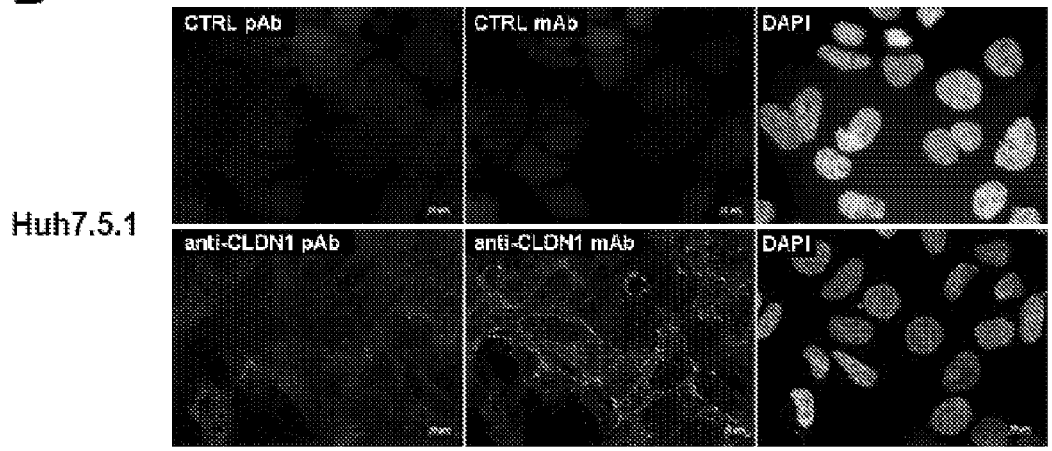
Huh7.5.1
Figure 3

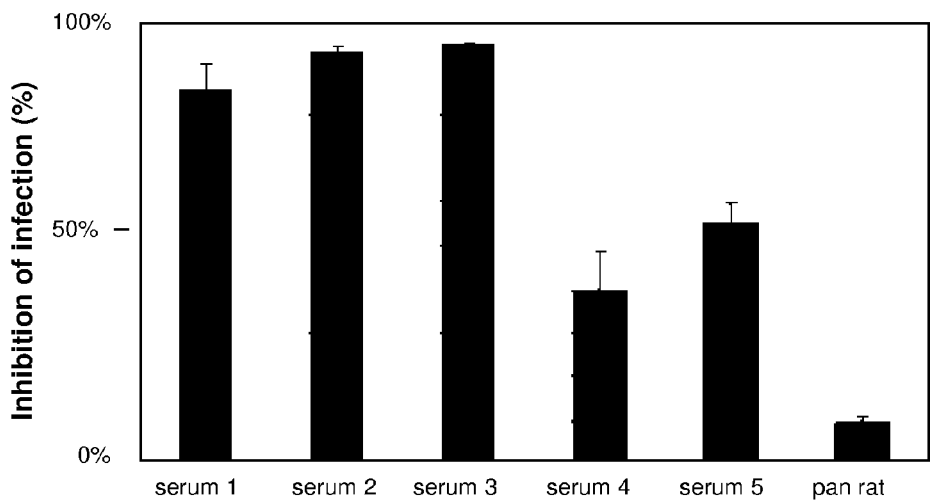
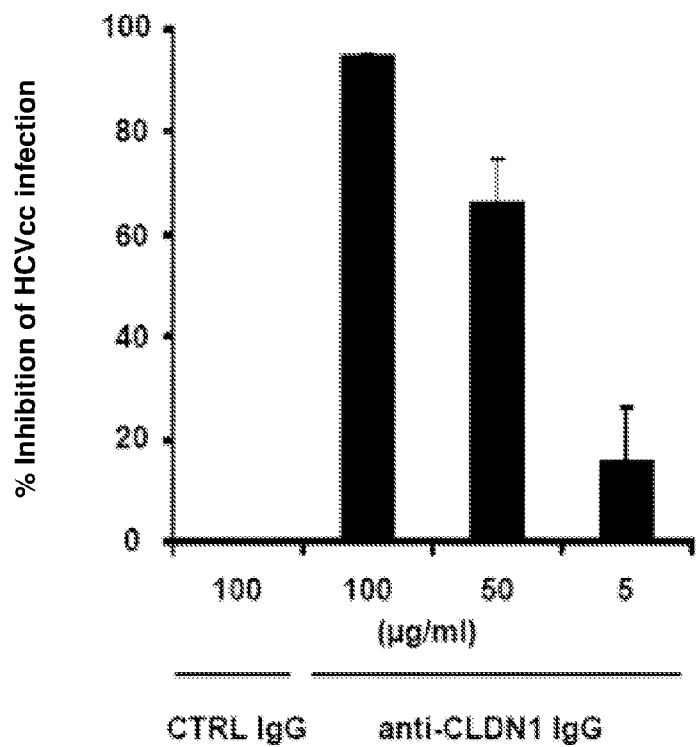
Figure 4

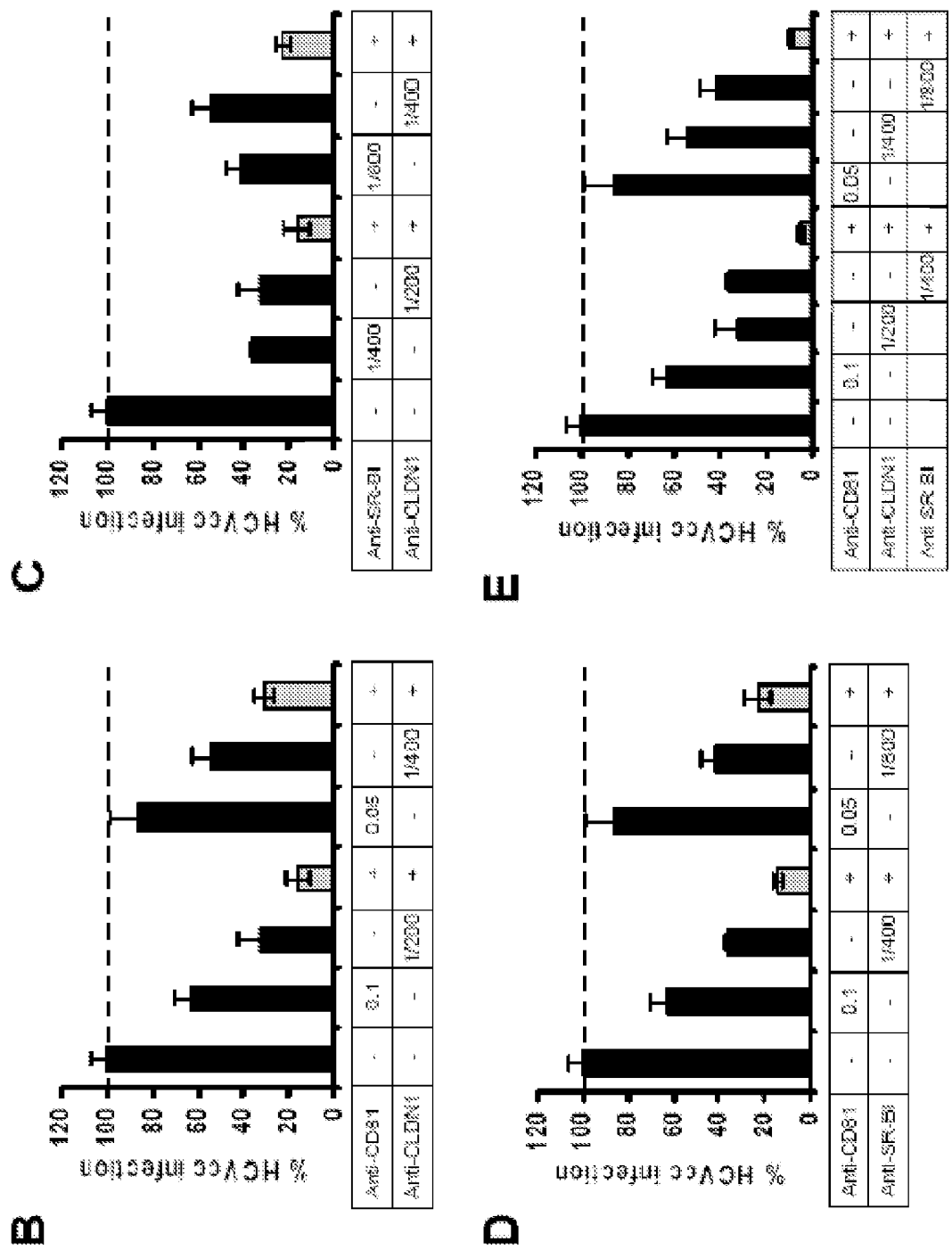
Figure 5(B)-(E)

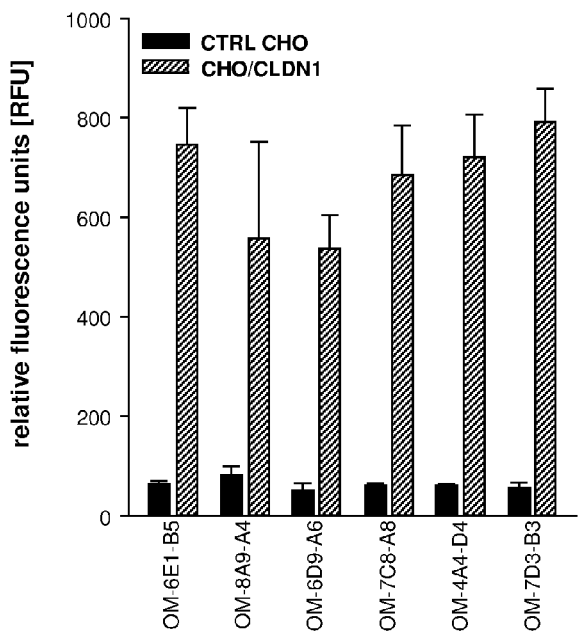
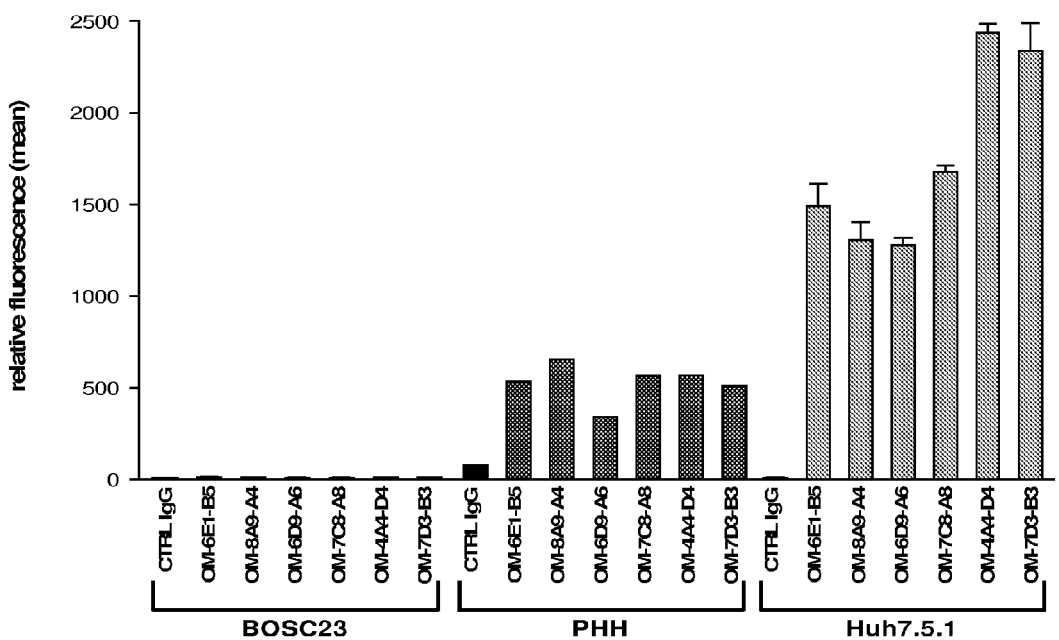
Figure 9(B)-(C)

D
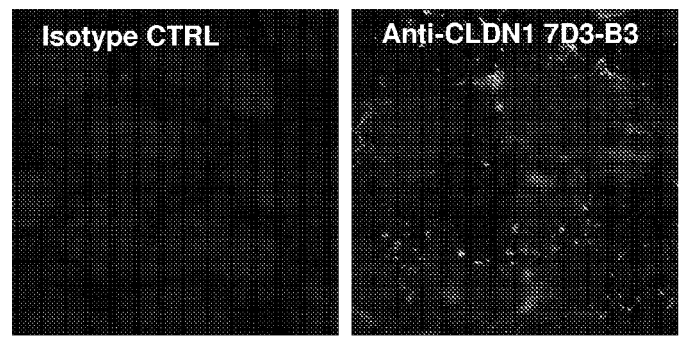
E
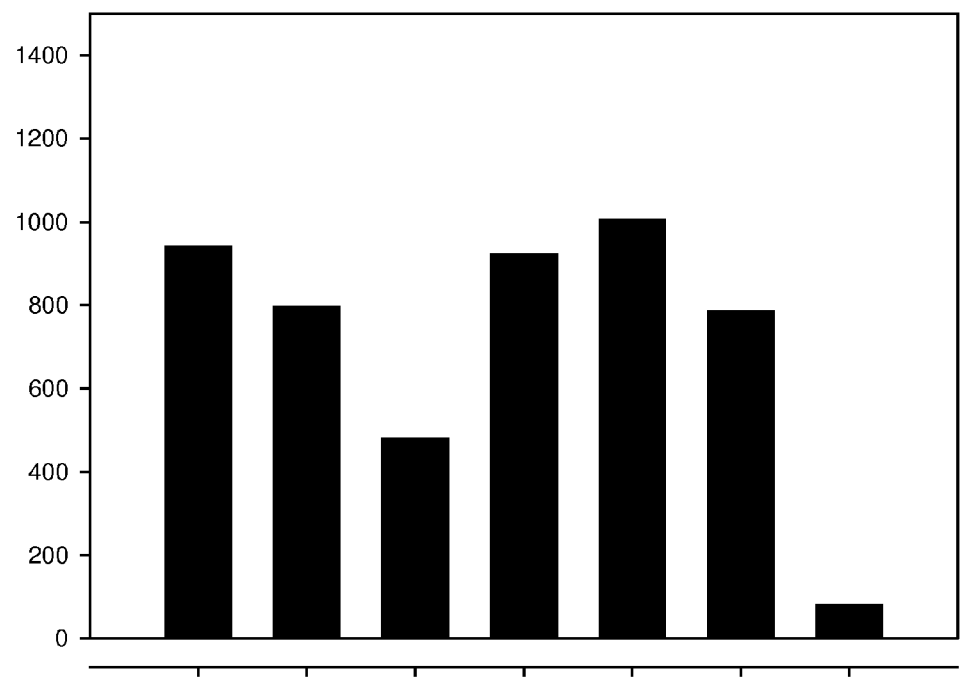
Figure 9(D)-(E)

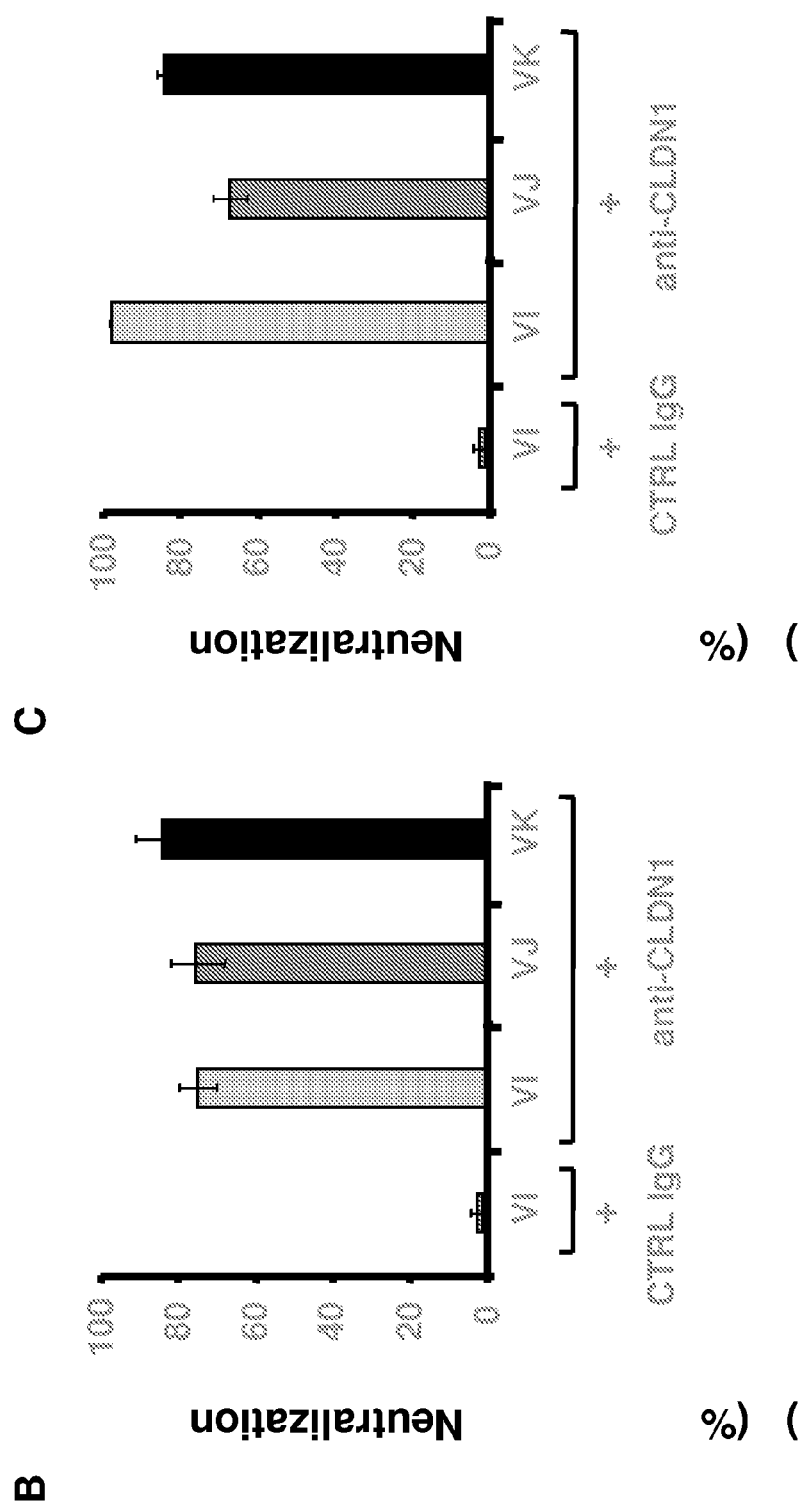
Figure 14(B)-(C)

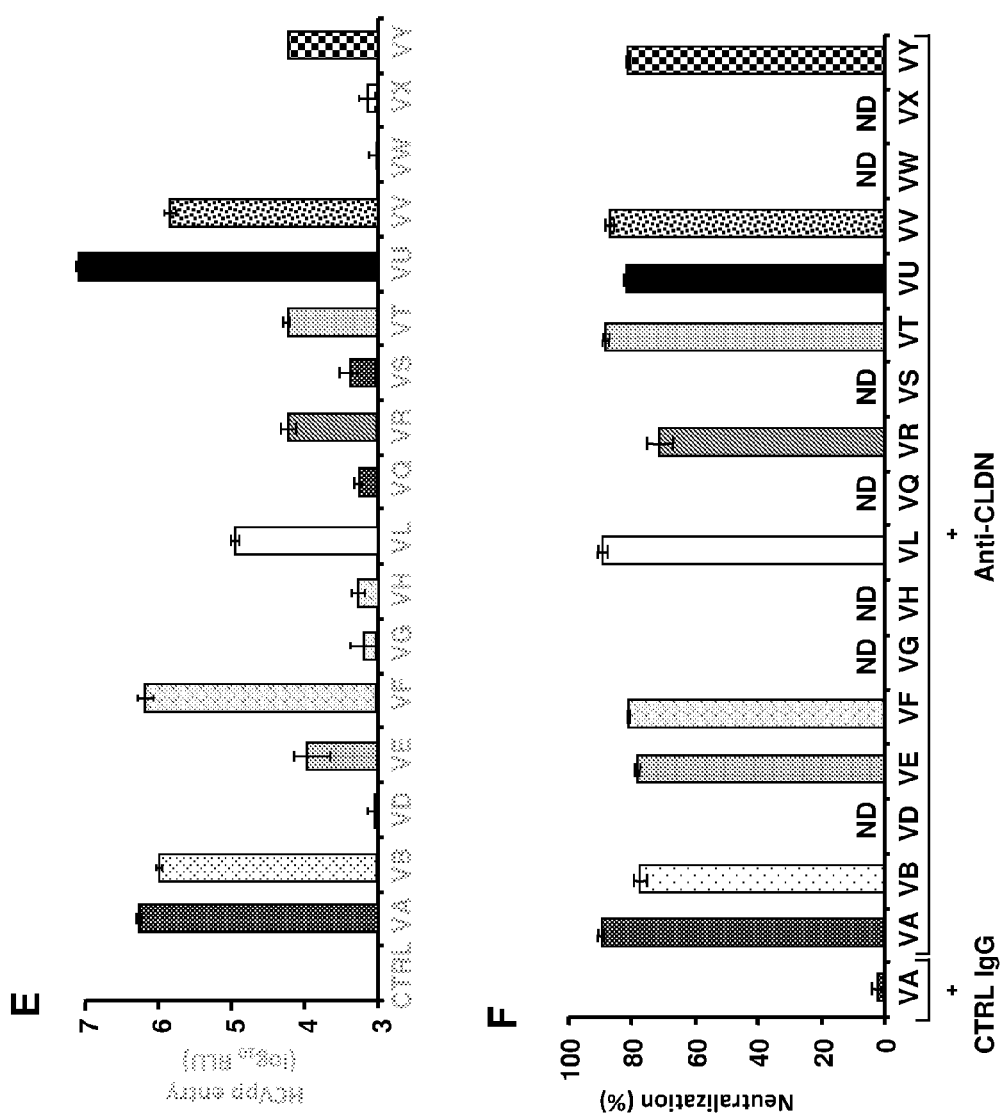
Figure 14(E)-(F)

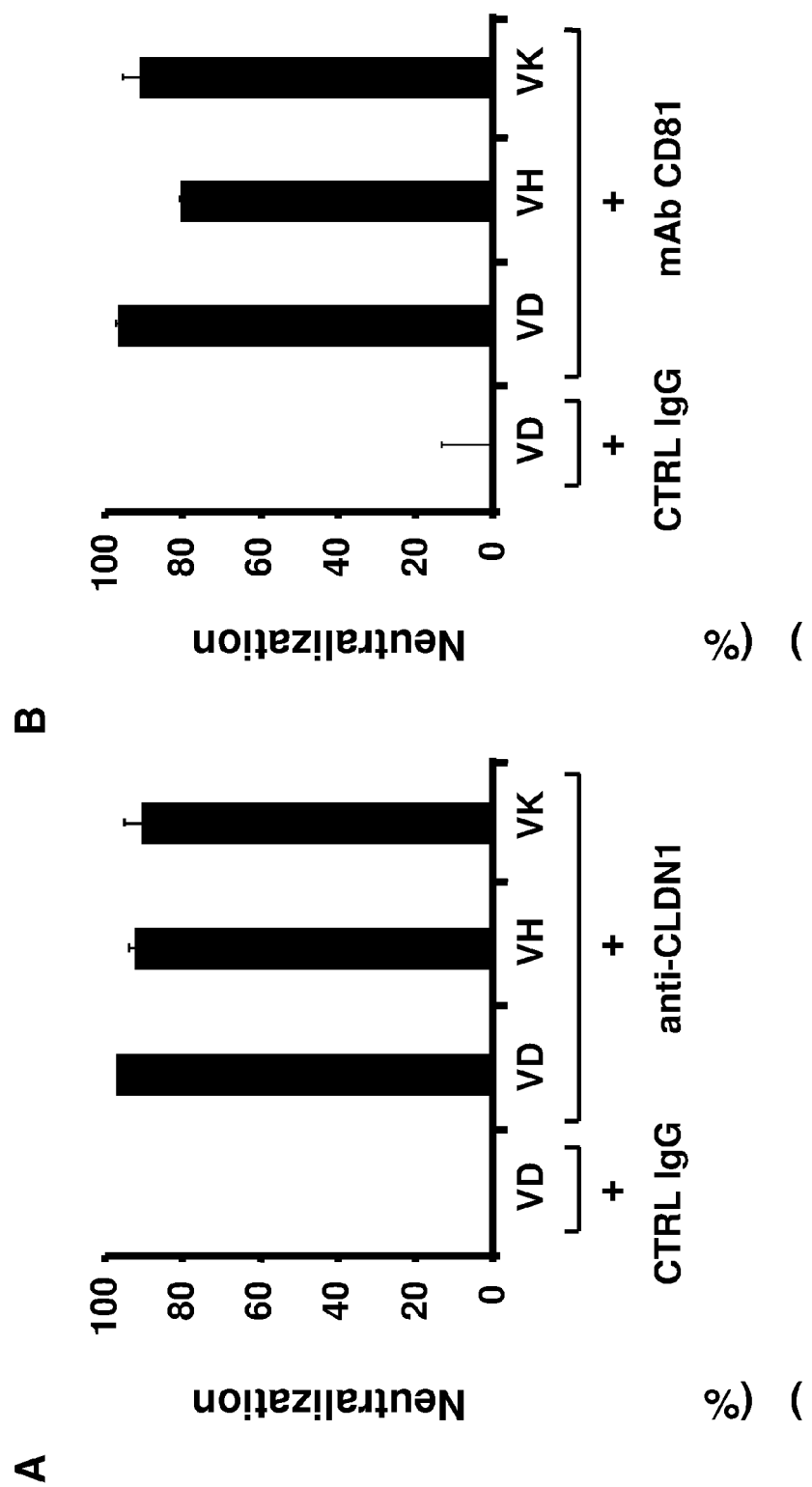
Figure 15 (A)-(B)

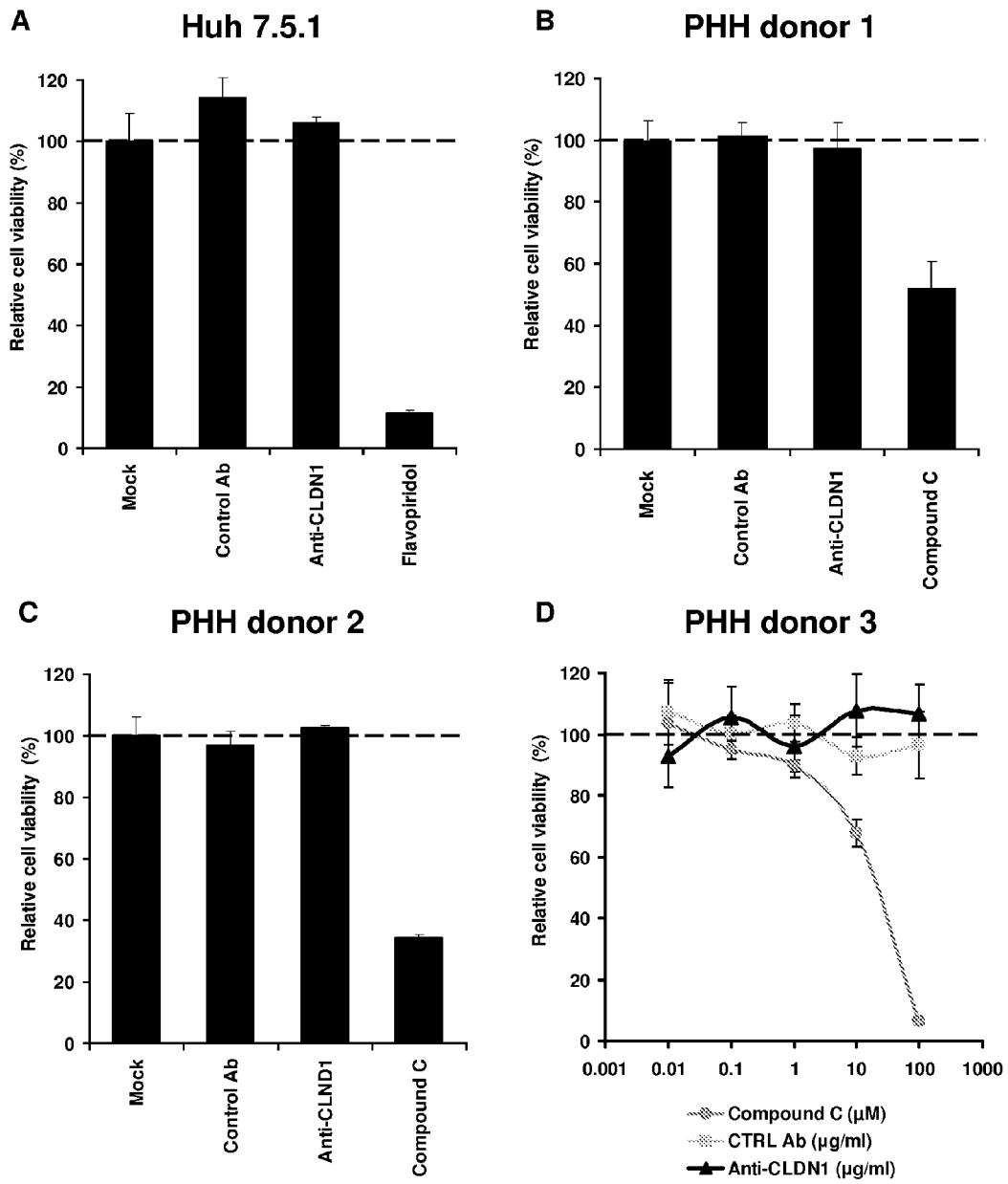
Figure 16 (A)-(D)

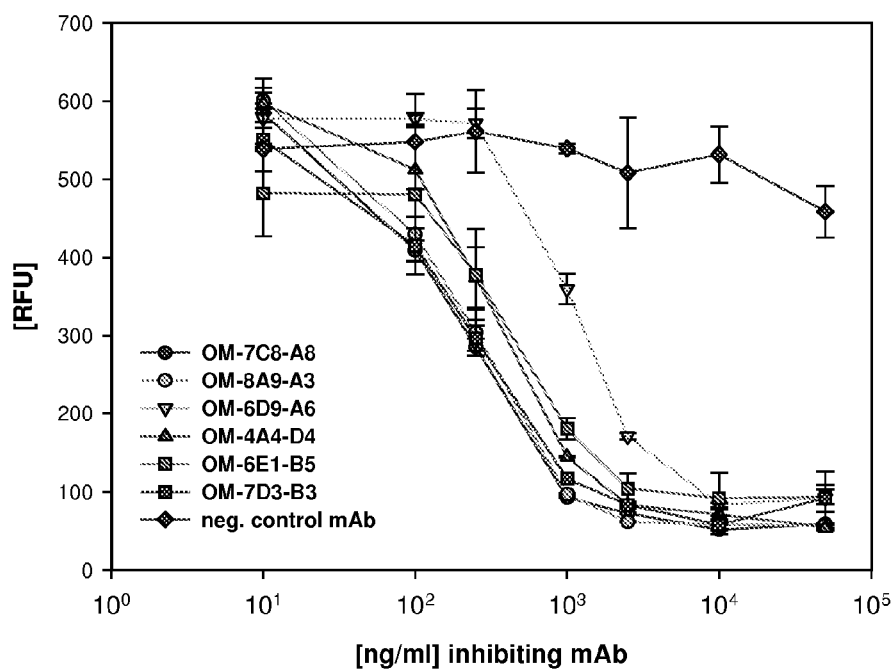
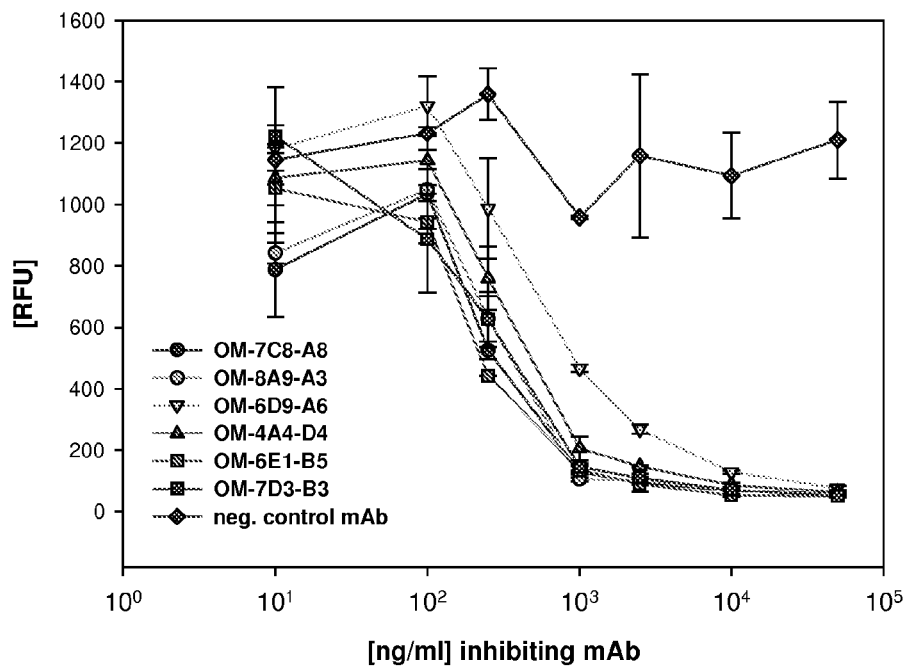
Figure 17 (A)

MONOCLONAL ANTI-CLAUDIN 1 ANTIBODIES FOR THE INHIBITION OF HEPATITIS C VIRUS INFECTION

RELATED APPLICATIONS

The present application is filed pursuant to 35 U.S.C. 371 as a U.S. National Phase application of International Patent Application No. PCT/EP09/62449, which was filed Sep. 25, 2009, claiming the benefit of priority to European Patent Application No. EP 08 305 597.0, which was filed on Sep. 25, 2008. The entire text of the aforementioned applications is incorporated herein by reference in its entirety.

BACKGROUND OF THE INVENTION

Hepatitis C virus (HCV) is a major global health problem, with an estimated 150-200 million people infected worldwide, including at least 5 million infected individuals within the European Union (Pawlotsky, 2004). According to the World Health Organization, 3 to 4 million new infections occur each year. The infection is often asymptomatic; however, the majority of HCV-infected individuals develop chronic infection (Hoofnagle, 2002; Lauer, 2001; and Seeff, 1995). Chronic HCV infection frequently results in serious liver disease, including fibrosis and steatosis (Chisari, 2005). About 20% of patients with chronic HCV infection develop liver cirrhosis, which progresses to hepatocellular carcinoma in 5% of the cases (Hoofnagle, 2002).

Chronic HCV infection is the leading indication for liver transplantations (Seeff, 2002). Unfortunately, liver transplantation is not a cure for hepatitis C; viral recurrence is an invariable problem and leading cause of graft loss (Brown, 2005). No vaccine protecting against HCV is available. Current therapies include administration of ribavirin and/or interferon-alpha (IFN-α), two non-specific anti-viral agents. Using a combination treatment of pegylated IFN-α and ribavirin, persistent clearance is achieved in about 50% of patients with chronic hepatitis C. However, a large number of patients have contraindications to one of the components of the combination, cannot tolerate the treatment, do not respond to IFN therapy at all or experience a relapse when administration is stopped. In addition to limited efficacy and substantial side effects such as neutropenia, haemolytic anemia and severe depression, current antiviral therapies are also characterized by high cost.

Until recently, the development of more effective therapeutics to combat HCV infection has been hampered by the lack of a cell culture system supporting HCV replication. Robust production of infectious HCV in cell culture has now been achieved using a unique HCV genome derived from the blood of a Japanese patient with fulminant hepatitis C (JFH-1) (Wakita, 2005; Lindenbach, 2005; Zhong, 2005). The ability of the JFH-1 strain of HCV to release infectious particles in cell culture (HCVcc) and the development of retroviral HCV pseudoparticles (HCVpp) (Bartosch, 2003; Hsu, 2003) have allowed studies on the mechanism of HCV entry and replication, that have led to the identification of potential therapeutic target biomolecules.

HCV is a positive strand RNA virus classified in the *Hepacivitus* genus, within the Flaviviridae family. Translation of the major open reading frame of the HCV genome results in the production of an approximately 3000 amino acid long polyprotein, which is cleaved co- and post-translationally by the coordinated action of cellular and viral proteases into at least 10 mature proteins, including two envelope glycoproteins (E1 and E2). HCV initiates infection by attaching to molecules or receptors on the surface of hepatocytes. Current evidence suggests that at least four host cell molecules are important for HCV entry in vitro: the tetraspanin CD81 (Pileri, 1998), the scavenger receptor class B type I (SB-RI) (Zeisel, 2007; Bartosch, 2003; Grove, 2007; Kapadia, 2007; Scarselli, 2002), Occludin (Ploss, 2009) and Claudin-1 (CLDN1), an integral membrane protein and a component of tight-junction strands (Evans, 2007). HCV glycoproteins have been reported to interact directly with CD81 and SR-BI (Cocquerel, 2006). Mutagenesis and antibody-blocking studies with tagged versions of CLDN1 suggest that the first extracellular loop is involved in interactions with HCV (Evans, 2007). However, the exact role played by each of the receptors is unclear.

Identification of these receptors or co-receptors for HCV has opened up new avenues for the development of therapeutic and prophylactic agents as drug candidates for the prevention and/or treatment of HCV infection. Thus, for example, Nicosia and coworkers have generated monoclonal antibodies against native human SR-BI that inhibit HCV E2 binding to SR-BI and efficiently block HCVcc infection of hepatoma cells in a dose-dependent manner (Catanese, 2007; WO 2006/005465). European patent application No. EP 1 256 348 discloses substances with antiviral effects (e.g., antibodies, proteins, sulphated polysaccharides and low molecule compounds) that inhibit binding of HCV E2 and CD81. International patent application WO 2007/130646 describes in vitro and cell-based assays for identifying agents that interfere with HCV interactions with Claudin-1 thereby preventing HCV infection. Since the development of novel therapeutic approaches against HCV remains a high-priority goal, these studies are encouraging as they demonstrate that agents that affect HCV entry into susceptible cells may constitute an effective and safe alternative to current HCV therapies.

SUMMARY OF THE INVENTION

The present invention relates to targeted systems and strategies for the prevention and/or treatment of HCV infection and HCV-related diseases. In particular, the present invention is directed to antibodies that interfere with HCV-host cells interactions by binding to the extracellular domain of Claudin-1, a known receptor of HCV. Without wishing to be bound by theory, binding of such an antibody to the extracellular domain of Claudin-1 on a cell surface is believed to inhibit or block HCV entry into the cell and to thereby prevent HCV infection of the cell. The Applicants have shown that anti-Claudin antibodies inhibit the binding of envelope glycoprotein E2 and virions to HCV permissive cell lines in the absence of detectable Claudin-E2 interaction. The Applicants have demonstrated that the antibodies neutralize HCV infectivity by reducing envelope glycoprotein E2 association with the cell surface and disrupting CD81-Claudin-1 interactions. The antibodies can be used in the prophylactic or therapeutic treatment of HCV infection (acute or chronic HCV infection) and HCV-related diseases or disorders (e.g., liver inflammation, cirrhosis, and hepatocellular carcinoma and liver transplantation). Antibodies such as those provided herein that inhibit HCV entry into cells are particularly attractive as antiviral therapeutics. An inhibitor of HCV entry does not need to cross the plasma membrane or to be modified intracellularly. In addition, because viral entry is mediated by conserved structures of the viral and cellular membranes, antibody inhibitors of viral entry can be very potent and less susceptible to the development of viral resistance.

More specifically, in one aspect, the present invention provides hybridoma cell lines which secrete monoclonal antibodies that specifically bind to the extracellular domain of human Claudin-1. In particular, the present Applicants have deposited eight of such hybridoma cell lines at the DSMZ (Deutsche Sammlung von Mikro-organismen and Zellkuturen GmbH, Inhoffenstraβe 7 B, 38124 Braunschweig, Germany) on Jul. 29, 2008. They were assigned Accession Numbers DSM ACC2931, DSM ACC2932, DSM ACC2933, DSM ACC2934, DSM ACC2935, DSM ACC2936, DSM ACC2937, and DSM ACC2938. The deposit was made pursuant to the provisions of the Budapest Treaty on the International recognition of the Deposit of Microorganism for the Purpose of Patent Procedure (Budapest Treaty).

In another aspect, the present invention provides a monoclonal antibody that is secreted by any one of the hybridoma cell lines deposited under Accession Numbers DSM ACC2931, DSM ACC2932, DSM ACC2933, DSM ACC2934, DSM ACC2935, DSM ACC2936, DSM ACC2937, and DSM ACC2938. The monoclonal antibody may or may not be isolated and/or purified from hybridoma cultures. In certain embodiments, the monoclonal antibody is an immunoglobulin of the rIgG2a heavy (H) chain and kappa light (L) chain isotype. In other embodiments, the monoclonal antibody is an immunoglobulin of the rIgG2b heavy (H) chain and kappa light (L) chain isotype.

As demonstrated by the Applicants, monoclonal antibodies secreted by the deposited hybridoma cell lines specifically bind to the extracellular domain of human Claudin-1 and efficiently inhibit HCV infection in vitro. The present invention also encompasses any biologically active fragment of the inventive monoclonal antibodies, i.e., any fragment or portion that retains the ability of the monoclonal antibody to interfere with HCV-host cells interactions, and/or to specifically bind to the extracellular domain of human Claudin-1, and/or to inhibit or block HCV entry into HCV-susceptible cells, and/or to reduce or prevent HCV infection of susceptible cells.

More generally, the present invention encompasses any molecule that comprises an inventive anti-Claudin-1 monoclonal antibody or a fragment thereof, including chimeric antibodies, humanized antibodies, de-immunized antibodies and antibody-derived molecules comprising at least one complementary determining region (CDR) from either a heavy chain or light chain variable region of an inventive anti-Claudin-1 monoclonal antibody as secreted by a hybridoma cell line, including molecules such as Fab fragments, F(ab')$_2$ fragments, Fd fragments, Sc antibodies (single chain antibodies), diabodies, individual antibody light single chains, individual antibody heavy chains, chimeric fusions between antibody chains and other molecules, and antibody conjugates, such as antibodies conjugated to a diagnostic agent (detectable moiety) or therapeutic agent, so long as these antibody-related molecules retain at least one biologically relevant property of the inventive monoclonal antibody from which it is "derived". The biologically relevant property may be the ability to interfere with HCV-host cells interactions, to specifically bind to the extracellular domain of human Claudin-1, to inhibit or block HCV entry into HCV-susceptible cells, and/or to reduce or prevent HCV infection of susceptible cells. In certain preferred embodiments, a biologically active fragment of a monoclonal antibody of the invention specifically binds to the extracellular domain of human Claudin-1.

The Applicants have shown that monoclonal antibodies secreted by the deposited hybridoma cell lines recognize an epitope that is strongly affected by mutations in the conserved motif in human Claudin-1 first extracellular loop. This motif is: W(30)-GLW(51)-C(54)-C(64). Consequently, in certain embodiments, a monoclonal antibody according to the present invention, or a biologically active fragment thereof, recognize an epitope that is dependent on the conserved motif W(30)-GLW(51)-C(54)-C(64) structure in Claudin-1 first extracellular loop.

Similarly, the Applicants have shown that monoclonal antibodies secreted by the deposited hybridoma cell lines do not cross-react with murine Claudin-1 but do cross-react with its orthologue in the non-human primate cynomolgus monkey (*Macaca fascicularis*). Therefore, in certain embodiments, a monoclonal antibody according to the present invention, or a biologically active fragment thereof, does not bind to rodent Claudin-1 but binds to non-human primate Claudin-1.

Generally, an antibody of the present invention inhibits the binding of envelope glycoprotein E2 or infectious virions to HCV permissive cell lines; and inhibits CD81-Claudin-1 association(s).

The monoclonal antibodies and antibody-related molecules of the present invention can find application in a variety of prophylactic and therapeutic treatments. Accordingly, in another aspect, the inventive monoclonal and antibody-related molecules are provided for preventing HCV infection of a cell (e.g., a susceptible cell or a population of susceptible cells); for preventing or treating HCV infection or a HCV-related disease in a subject; for controlling chronic HCV infection; and for preventing HCV recurrence in a liver transplantation patient. HCV infection may be due to HCV of a genotype selected from the group consisting of genotype 1, genotype 2, genotype 3, genotype 4, genotype 5 and genotype 6, or more specifically of a subtype selected from the group consisting of subtype 1a, subtype 1b, subtype 2a, subtype 2b, subtype 2c, subtype 3a, subtype 4a-f, subtype 5a, and subtype 6a.

In a related aspect, the present invention provides a method of reducing the likelihood of a susceptible cell of becoming infected with HCV as a result of contact with HCV, which comprises contacting the susceptible cell with an effective amount of an inventive antibody or antibody-related molecule. Also provided is a method of reducing the likelihood of a subject's susceptible cells of becoming infected with HCV as a result of contact with HCV, which comprises administering to the subject an effective amount of an inventive antibody or antibody-related molecule. The present invention also provides a method of treating or preventing HCV infection or a HCV-associated disease (e.g., a liver disease or pathology) in a subject in need thereof which comprises administering to the subject an effective amount of an inventive monoclonal antibody or antibody-related molecule. The invention also provides a method for controlling chronic HCV infection in a subject in need thereof which comprises administering to the subject an effective amount of an inventive monoclonal antibody or antibody-related molecule.

Also provided is a method of preventing HCV recurrence in a liver transplantation patient, which comprises administering to the patient an effective amount of an inventive monoclonal antibody or antibody-related molecule. Administration of an inventive antibody or antibody-related molecule to a subject may be by any suitable route, including, for example, parenteral, aerosol, oral and topical routes. The inventive monoclonal antibody or antibody-related molecule may be administered alone or in combination with a therapeutic agent, such as an anti-viral agent.

The inventive monoclonal antibodies and antibody-related molecules may be administered per se or as pharmaceutical compositions. Accordingly, in another aspect, the present invention provides for the use of an inventive monoclonal antibody or antibody-related molecule for the manufacture of medicaments, pharmaceutical compositions, or pharmaceutical kits for the treatment and/or prevention of HCV infection and HCV-associated diseases.

In a related aspect, the present invention provides a pharmaceutical composition comprising an effective amount of an inventive monoclonal antibody or antibody-related molecule and at least one pharmaceutically acceptable carrier or excipient. In certain embodiments, the pharmaceutical composition is adapted for administration in combination with an additional therapeutic agent, such as an antiviral agent. In other embodiments, the pharmaceutical composition further comprises an additional therapeutic agent, such as an antiviral agent. Antiviral agents suitable for use in methods and pharmaceutical compositions of the present invention include, but are not limited to, interferons (e.g., interferon-alpha, pegylated interferon-alpha), ribavirin, anti-HCV (monoclonal or polyclonal) antibodies, RNA polymerase inhibitors, protease inhibitors, IRES inhibitors, helicase inhibitors, antisense compounds, ribozymes, and any combination thereof.

When conjugated to a detectable moiety, a monoclonal antibody or antibody-related molecule of the invention can find applications in a variety of non-therapeutic methods, for example in the diagnosis and/or prognosis of certain diseases such as cancers. Indeed, the expression level of claudin-1 has been demonstrated to be a useful diagnostic or prognostic marker for different cancers. Accordingly, in another aspect, the present invention provides for the use of an inventive monoclonal antibody or antibody-related molecule for the manufacture of compositions or kits for the diagnosis and/or prognosis of certain cancers.

In a related aspect, the present invention provides a method for detecting Claudin-1 in a biological sample which comprises contacting the biological sample with an inventive antibody for a time and under conditions allowing an antibody-Claudin-1 complex to form between the antibody and claudin-1 present in the biological sample; and detecting (and/or quantitating) the presence of any antibody-Claudin-1 complex formed. The inventive antibody (or antibody-related molecule) used in such a method is preferably conjugated to a detectable moiety. In certain embodiments, the biological sample is obtained from a subject, for example, a subject suspected of having a cancer. Diagnosis or prognosis may be provided based on the presence, absence or quantity of antibody-Claudin-1 complex formed, for example, after comparison with results obtained under identical conditions for a biological sample obtained from a healthy subject.

These and other objects, advantages and features of the present invention will become apparent to those of ordinary skill in the art having read the following detailed description of the preferred embodiments.

BRIEF DESCRIPTION OF THE DRAWING

FIG. 2 is a set of three graphs demonstrating the interaction of anti-CLDN-1 antibodies with the CLDN-1 ectodomain on Huh7.5.1 human hepatoma cells (FIG. 2A), human hepatocytes (FIG. 2B). Cell surface expression of CLDN-1 was determined by flow cytometry using rat anti-human CLDN-1 serum or control pre-immune serum (see Example 1). Histograms corresponding to cell surface expression of the respective cell surface molecules (open curves) are overlaid with histograms of cells incubated with the appropriate isotype control (grey shaded curves). Rat anti-human CLDN-1 serum specifically detected CLDN-1 on the cell surface of human hepatoma Huh7.5.1 cells, and human primary hepatocytes.

FIG. 3 is a set of immunofluorescence images showing CLDN1 expression in Caco2 (A) and Huh7.5.1 (B) cells. The lower panels of FIG. 3A and FIG. 3B show Caco2 cells and Huh7.5.1 cells, respectively, that were stained for CLDN1 using anti-CLDN1 polyclonal antibodies directed against the CLDN1 ectodomains ("anti-CLDN1 pAb"), and a commercial anti-CLDN1 antibody directed against the intracellular C-terminal domain ("anti-CLDN1 mAb") and for the nucleus using DAPI, as described in Example 1. Controls are shown in the upper panels of FIG. 3A and FIG. 3B, where Caco2 cells and Huh7.5.1 cells, respectively, were incubated with rat polyclonal IgG ("control pAb"), mouse monoclonal IgG ("control mAb"), and DAPI. The scale bars represent 10 μm.

FIG. 4 is a set of two graphs showing the inhibition of HCV infection (Jc1 HCVcc infection) by anti-CLDN-1 antibodies (rat polyclonal anti-CLDN-1 antiserum). FIG. 4A shows the results obtained for Huh7.5.1 cells that were pre-incubated for 1 hour at 37° C. with anti-CLDN-1 rat serum (dilution 1/50) or control serum ("pan rat") before infection with JC1 HCVcc for 3 hours at 37° C. HCV infection was assessed by HCV RNA quantitation in lysates of infected Huh7.5.1 cells 72 hours post-infection. Total RNA was isolated and HCV RNA was quantified by pRT-PCR. FIG. 4B shows the inhibition of Jc1 HCVcc infection by purified anti-CLDN-1 immunoglobulin. Anti-CLDN-1 IgG was purified from serum No. 2 and added to Huh7.5.1 cells as described in Example 1 (CTRL—control IgG). HCV infection was assessed by HCV RNA quantitation as described above. Results are expressed as mean % HCVcc infectivity±SD from duplicate determinations of one out of at least two independent experiments.

FIG. 5(B)-(E) is a set of four graphs showing the additive effect of anti-SR-BI, anti-CD81 and anti-CLDN1 antibodies in the inhibition of HCVcc entry. Huh7.5.1 cells were preincubated for 1 hour at 37° C. with rat anti-SR-BI (1/400, 1/800), rat anti-CLDN1 (1/200, 1/400) and mouse anti-CD81 (0.05, 0.1 μg/mL) either alone (black bars) or in combination (grey bars) before infection with Luc-Jc1 HCVcc for 4 hours at 37° C. HCVcc infection was assessed as described in (A). Data are expressed as percent Luc-Jc1 HCVcc infectivity in the absence of antibody. Means±SD of four independent experiments performed in duplicate are shown.

FIG. 9(B) is a graph showing the specific binding of six monoclonal anti-human CLDN1 antibodies to CLDN1 expressed on the cell surface of transfected CHO cells studied by flow cytometry. CHO cells were transfected with pCMV-SPORT6-CLDN1 (striped bars) or control vector (pCMV-SPORT6; black bars). FIG. 9(C) is a graph showing the binding of the six monoclonal antibodies to cell surface expressed CLDN1 on Huh7.5.1 hepatoma cells and primary human hepatocytes (PHH) and as a negative control on BOSC23 cells. Results are shown as the mean relative fluorescent units (RFU) calculated for each experiment performed in duplicate. FIG. 9(D) shows the imaging of cell surface CLDN1 on living, non-permeabilized Huh7.5.1 cells by an anti-CLDN1 monoclonal antibody. Huh7.5.1 cells were incubated with rat isotype control or anti-CLDN10M-7D3-A3 antibodies (10 μg/mL), a Cy5-conjugated anti-rat secondary antibody and analyzed as described in Example 2. Cell nuclei were stained with DAPI. FIG. 9(E) is a graph showing the binding of the six monoclonal antibodies to cell surface expressed CLDN1 on primary cynomolgus hepatocytes studied by flow cytometry.

FIG. 14 shows that anti-CLDN1 monoclonal antibodies cross-neutralize the infection by HCV-quasispecies in two individual patients with chronic HCV infection (see Example 2). FIG. 14(B)-(C) is a set of two graphs showing the inhibition of infection of HCVpp bearing envelope glycoproteins of viral quasispecies in this patient by anti-CLDN1 OM-7D3 (25 µg/mL) in Huh7.5.1 cells (B) and primary human hepatocytes (C). FIG. 14(E)-(F) is a set of two graphs showing infection of Huh7.5.1 cells by HCVpp bearing envelope glycoproteins of viral quasispecies of the second patient with chronic hepatitis C (D) and its neutralization by anti-CLDN1 OM-7D3 (25 µg/mL) (E). Infection of HCVpp was analyzed as described in Example 2. Neutralization by anti-CLDN1 antibody was only assessed for HCVpp derived from quasispecies with detectable infectivity. Viral variants containing a stop codon are indicated by an asterix. Mean±SD from a representative experiment performed in triplicate are shown. ND—not done; CTRL IgG—rat isotype control antibody.

FIG. 15 is a set of two graphs showing the prevention of HCV infection of HCVpp bearing envelope glycoproteins from patients with escape from host neutralizing responses and re-infection of the liver-graft. HCVpp (strains termed VD, VH, VK) bearing envelope glycoproteins from three different patients with escape from host neutralizing responses and re-infection of the liver graft (HCV subtype 1b) were produced as described in Example 2. Prevention of HCVpp infection was assessed by pre-incubating primary human hepatocytes with anti-CLDN1 antibody OM-7D3 (25 µg/ml) or anti-CD81 or isotype control (CTRL) antibodies (25 µg/ml) for 1 hour at 37° C. before infection with HCVpp for 4 hours at 37° C. Infection was analyzed as described in Example 2. Mean±SD from representative experiments performed in triplicate are shown.

FIG. 16 is a set of graphs showing the lack of toxicity of anti-CLDN1 monoclonal antibodies in Huh7.5.1 cells and primary human hepatocytes (PHH). Cytotoxic effects on cells were assessed in triplicates by metabolization of MTT. Huh7.5.1 cells (A) and primary human hepatocytes from three different donors (B-D) were incubated with rat monoclonal antibody, anti-CLDN1 OM-7D3-B3 (10 µg/ml), flavopiridol (10 µM) or compound C (20 µM) for 48 hours and analyzed by MTT metabolization. Relative cell viability was assessed in comparison to mock incubated primary human hepatocytes or Huh7.5.1 cells (=100%) (D) Compound C (0.01-100 µM), anti-CLDN1 OM-7D3 antibody (0.01-100 µM) or isotype control antibody were added to primary human hepatocytes in increasing doses and toxicity assessed as described in panels (B) and (C).

FIG. 17(A): Competition between anti-CLDN1 MAbs was measured using a cell-based ELISA. Huh7.5.1 cells were incubated with 0.1 µg/mL biotinylated anti-CLDN1 mAb (OM-8A9-A3—upper panel or OM-7D3-B3—lower panel) together with increasing concentrations of unlabeled anti-CLDN1 MAbs as competitors. Following washing of cells in PBS, binding of biotinylated antibody was detected by incubation with streptavidin labelled with horseradish peroxidase. Binding was measured as relative fluorescence units (RFU). Curves determined by measurement of binding in the presence of an isotype-matched control (negative control mAb) were compared to those determined in the presence of the competing antibody. FIG. 17(B): Cross-competition between the entire panel of anti-CLDN1 monoclonal antibodies. Cross-competition was analyzed as shown in panel A using 0.1 µg/mL biotinylated anti-CLDN1 mAb (shown on the x-axis) and 10 µg/ml of the competing unlabeled anti-CLDN1 or an isotype control mAb (irr control antibody) (shown on the y-axis). Binding of biotinylated anti-CLDN1 mAb occurred only in the presence of isotype control antibody. FIG. 17(C): Cross-competition of antibodies in infection studies. Huh7.5.1 cells were pre-incubated with rat anti-CLDN1 or isotype control antibodies for 1 hour at 37° C. before infection with Luc-Jc1 HCVcc as described in Example 2. To study cross-competition, low concentrations of anti-CLDN1 mAbs (0.5 µg/ml) were added simultaneously prior to HCV infection. The use of antibody concentrations that sub-maximally blocked HCV infection allowed observation of additive or synergistic effects. The effect of antibody combinations is indicated by a "+" (final concentration 1 µg/ml) (striped bars).

DEFINITIONS

Figure 1:
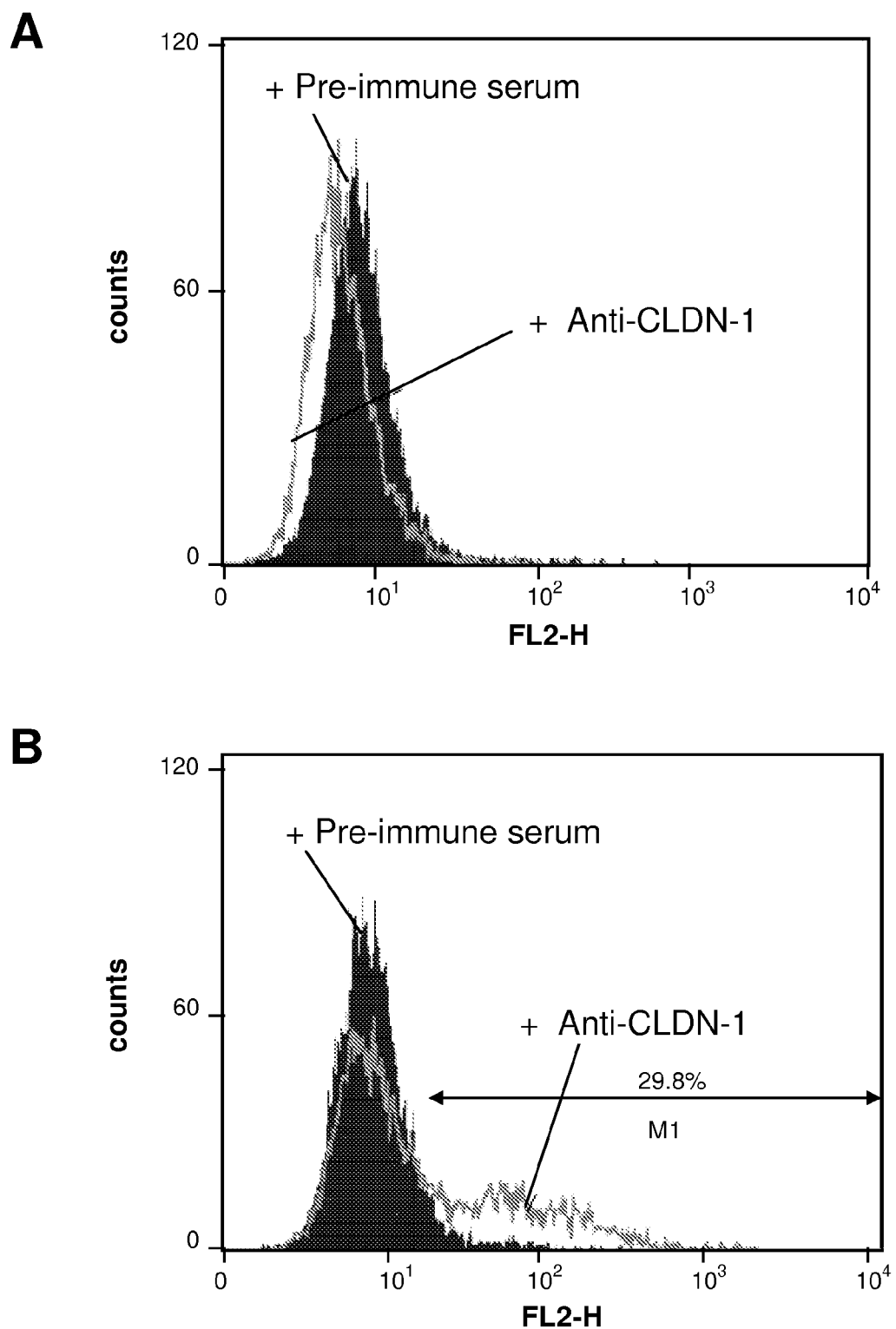
FIG. 1 is a set of two graphs illustrating the specific binding of rat anti-human CLDN-1 serum to CLDN-1 expressed in CHO cells. Anti-CLDN-1 polyclonal serum directed against the CLDN-1 ectodomain loop was raised by genetic immunization of Wistar rats using a plasmid harboring human CLDN-1 cDNA (see Example 1). CHO cells were transfected with pcDNA-CLDN-1 or a control vector (pcDNA). Flow cytometry of CLDN-1 or control transfected non-permeabilized CHO cells incubated with rat anti-human CLDN-1 polyclonal serum and PE-conjugated anti-rat IgG demonstrated specific interaction of anti-CLDN-1 antibodies with human CLDN-1 (FIG. 1B). In contrast, no interaction was observed in CHO cells transfected with the control vector and incubated with anti-CLDN-1 serum (FIG. 1A).
Figure 5A:
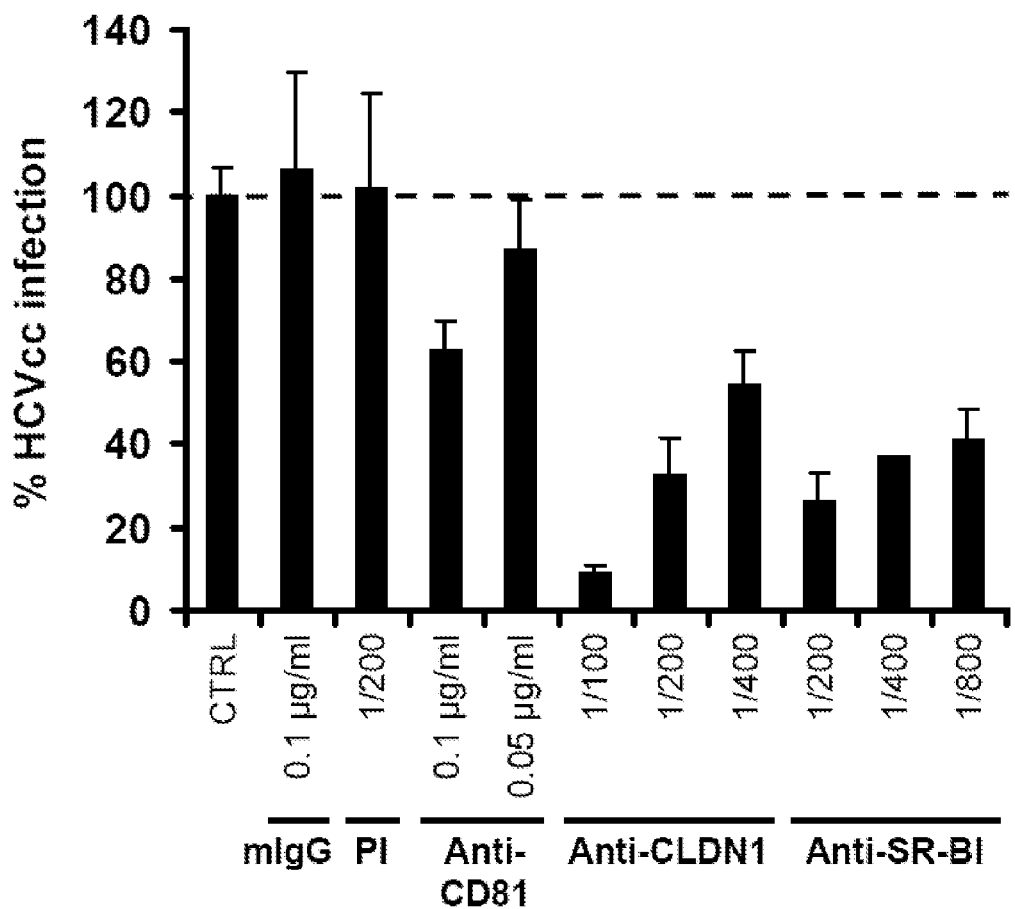
FIG. 5(A) shows the dose-dependence inhibition of Luc-Jc1 HCVcc infection by anti-SR-BI, anti-CD81 and anti-CLDN1 antibodies. The use of antibody concentrations that sub-maximally blocked HCV infection allowed the observation of additive or synergistic effects. Huh7.5.1 cells were preincubated for 1 hour at 37° C. with anti-CD81 mAb (0.1 and 0.05 μg/mL), control mouse mAb (mIgG: 0.1 and 0.05 μg/mL), rat-anti-SR-BI serum (1/200, 1/400, and 1/800), rat anti-CLDN1 serum (1/100, 1/200, 1/400) or control rat-pre-immune serum (CTRL: 1/200) before infection with Luc-Jc1 HCVcc for 4 hours at 37° C. HCV infection was assessed by measurement of luciferase activity 48 hours post-infection. Data are expressed as percent Luc-Jc1 HCVcc infectivity in the absence of antibody. Means±SD of four independent experiments performed in duplicate are shown.

Throughout the specification, several terms are employed that are defined in the following paragraphs.

As used herein, the term "subject" refers to a human or another mammal (e.g., primate, dog, cat, goat, horse, pig, mouse, rat, rabbit, and the like), that can be the host of Hepatitis C virus (HCV), but may or may not be infected with the virus, and/or may or may not suffer from a HCV-related disease. Non-human subjects may be transgenic or otherwise modified animals. In many embodiments of the present invention, the subject is a human being. In such embodiments, the subject is often referred to as an "individual". The term "individual" does not denote a particular age, and thus encompasses newborns, children, teenagers, and adults.

As used herein, the term "HCV" refers to any major HCV genotype, subtype, isolate and/or quasispecies. HCV genotypes include, but are not limited to, genotypes 1, 2, 3, 4, 5, and 6; HCV subtypes include, but are not limited to, subtypes 1a, 1b, 2a, 2b, 2c, 3a, 4a-f, 5a and 6a.

The terms "afflicted with HCV" or "infected with HCV" are used herein interchangeably. When used in reference to a subject, they refer to a subject that has at least one cell which is infected by HCV. The term "HCV infection" refers to the introduction of HCV genetic information into a target cell, such as by fusion of the target cell membrane with HCV or an HCV envelope glycoprotein-positive cell.

The terms "HCV-related disease" and "HCV-associated disease" are herein used interchangeably. They refer to any disease or disorder known or suspected to be associated with and/or caused, directly or indirectly, by HCV. HCV-related (or HCV-associated) diseases include, but are not limited to, a wide variety of liver diseases, such as subclinical carrier state of acute hepatitis, chronic hepatitis, cirrhosis, and hepatocellular carcinoma. The term includes symptoms and side effects of any HCV infection, including latent, persistent and sub-clinical infections, whether or not the infection is clinically apparent.

The term "treatment" is used herein to characterize a method or process that is aimed at (1) delaying or preventing the onset of a disease or condition (e.g., HCV infection or HCV-related disease); (2) slowing down or stopping the progression, aggravation, or deterioration of the symptoms of the disease or condition; (3) bringing about amelioration of the symptoms of the disease or condition; or (4) curing the disease or condition. A treatment may be administered prior to the onset of the disease or condition, for a prophylactic or preventive action. Alternatively or additionally, a treatment may be administered after initiation of the disease or condition, for a therapeutic action.

A "pharmaceutical composition" is defined herein as comprising an effective amount of at least one antibody (or a fragment thereof) of the invention, and at least one pharmaceutically acceptable carrier or excipient.

As used herein, the term "effective amount" refers to any amount of a compound, agent, antibody, or composition that is sufficient to fulfil its intended purpose(s), e.g., a desired biological or medicinal response in a cell, tissue, system or subject. For example, in certain embodiments of the present invention, the purpose(s) may be: to prevent HCV infection, to prevent the onset of a HCV-related disease, to slow down, alleviate or stop the progression, aggravation or deterioration of the symptoms of a HCV-related disease (e.g., chronic hepatitis C, cirrhosis, and the like); to bring about amelioration of the symptoms of the disease, or to cure the HCV-related disease.

The term "pharmaceutically acceptable carrier or excipient" refers to a carrier medium which does not interfere with the effectiveness of the biological activity of the active ingredient(s) and which is not excessively toxic to the host at the concentration at which it is administered. The term includes solvents, dispersion, media, coatings, antibacterial and antifungal agents, isotonic agents, and adsorption delaying agents, and the like. The use of such media and agents for pharmaceutically active substances is well known in the art (see for example "*Remington's Pharmaceutical Sciences*", E. W. Martin, 18$^{th}$ Ed., 1990, Mack Publishing Co.: Easton, Pa., which is incorporated herein by reference in its entirety).

The term "antibody", as used herein, refers to any immunoglobulin (i.e., an intact immunoglobulin molecule, an active portion of an immunoglobulin molecule, etc.) that binds to a specific epitope. The term encompasses monoclonal antibodies and polyclonal antibodies. All derivatives and fragments thereof, which maintain specific binding ability, are also included in the term. The term also covers any protein having a binding domain, which is homologous or largely homologous to an immunoglobulin-binding domain. These proteins may be derived from natural sources, or partly or wholly synthetically produced.

The term "specific binding", when used in reference to an antibody, refers to an antibody binding to a predetermined antigen. Typically, the antibody binds with an affinity of at least $1\times10^7$ M$^{-1}$, and binds to the predetermined antigen with an affinity that is at least two-fold greater than the affinity for binding to a non-specific antigen (e.g., BSA, casein).

The term "human Claudin-1 or human CLDN1" refers to a protein having the sequence shown in NCBI Accession Number NP_066924, or any naturally occurring variants commonly found in HCV permissive human populations. The term "extracellular domain" or "ectodomain" of Claudin-1 refers to the region of the Claudin-1 sequence that extends into the extracellular space (i.e., the space outside a cell).

The terms "susceptible cell" and "HCV-susceptible cell" are used interchangeably. They refer to any cell that may be infected with HCV. Susceptible cells include, are not limited to, liver or hepatic cells, primary cells, hepatoma cells, CaCo2 cells, dendritic cells, placental cells, endometrial cells, lymph node cells, lymphoid cells (B and T cells), peripheral blood mononuclear cells, and monocytes/macrophages.

The term "preventing, inhibiting or blocking HCV infection" when used in reference to an inventive antibody or antibody-related molecule, means reducing the amount of HCV genetic information introduced into a susceptible cell or susceptible cell population as compared to the amount that would be introduced in the absence of the antibody or antibody-related molecule.

The term "isolated", as used herein in reference to a protein or polypeptide, means a protein or polypeptide, which by virtue of its origin or manipulation is separated from at least some of the components with which it is naturally associated or with which it is associated when initially obtained. By "isolated", it is alternatively or additionally meant that the protein or polypeptide of interest is produced or synthesized by the hand of man.

The terms "protein", "polypeptide", and "peptide" are used herein interchangeably, and refer to amino acid sequences of a variety of lengths, either in their neutral (uncharged) forms or as salts, and either unmodified or modified by glycosylation, side-chain oxidation, or phosphorylation. In certain embodiments, the amino acid sequence is a full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversions of the chains such as oxidation of sulfydryl groups. Thus, the term "protein" (or its equivalent terms) is intended to include the amino acid sequence of the full-length native protein, or a fragment thereof, subject to those modifications that do not significantly change its specific properties. In particular, the term "protein" encompasses protein isoforms, i.e., variants that are encoded by the same gene, but that differ in their pI or MW, or both. Such isoforms can differ in their amino acid sequence (e.g., as a result of allelic variation, alternative splicing or limited proteolysis), or in the alternative, may arise from differential post-translational modification (e.g., glycosylation, acylation, phosphorylation).

The term "analog", as used herein in reference to a protein, refers to a polypeptide that possesses a similar or identical function as the protein but need not necessarily comprise an amino acid sequence that is similar or identical to the amino acid sequence of the protein or a structure that is similar or identical to that of the protein. Preferably, in the context of the present invention, a protein analog has an amino acid sequence that is at least 30%, more preferably, at least 35%, 40%, 45%, 50%, 55%, 60%, 65%, 70%, 75%, 80%, 85%, 90%, 95% or 99% identical to the amino acid sequence of the protein.

The term "fragment" or the term "portion", as used herein in reference to a protein, refers to a polypeptide comprising an amino acid sequence of at least 5 consecutive amino acid residues (preferably, at least about: 10, 15, 20, 25, 30, 35, 40, 50, 60, 70, 80, 90, 100, 125, 150, 175, 200, 250 or more amino acid residues) of the amino acid sequence of a protein. The fragment of a protein may or may not possess a functional activity of the protein.

The term "biologically active", as used herein to characterize a protein variant, analog or fragment, refers to a molecule that shares sufficient amino acid sequence identity or homology with the protein to exhibit similar or identical properties to the protein. For, example, in many embodiments of the present invention, a biologically active fragment of an inventive antibody is a fragment that retains the ability of the antibody to bind to the extracellular domain of Claudin-1.

The term "homologous" (or "homology"), as used herein, is synonymous with the term "identity" and refers to the sequence similarity between two polypeptide molecules or between two nucleic acid molecules. When a position in both compared sequences is occupied by the same base or same amino acid residue, the respective molecules are then homologous at that position. The percentage of homology between two sequences corresponds to the number of matching or homologous positions shared by the two sequences divided by the number of positions compared and multiplied by 100. Generally, a comparison is made when two sequences are aligned to give maximum homology. Homologous amino acid sequences share identical or similar amino acid sequences. Similar residues are conservative substitutions for, or "allowed point mutations" of, corresponding amino acid residues in a reference sequence. "Conservative substitutions" of a residue in a reference sequence are substitutions that are physically or functionally similar to the corresponding reference residue, e.g. that have a similar size, shape, electric charge, chemical properties, including the ability to form covalent or hydrogen bonds, or the like. Particularly preferred conservative substitutions are those fulfilling the criteria defined for an "accepted point mutation" as described by Dayhoff et al. ("Atlas of Protein Sequence and Structure", 1978, Nat. Biomed. Res. Foundation, Washington, D.C., Suppl. 3, 22: 354-352).

The terms "labeled", "labeled with a detectable agent" and "labeled with a detectable moiety" are used herein interchangeably. These terms are used to specify that an entity (e.g., an antibody) can be visualized, for example, following binding to another entity (e.g., an antigen). Preferably, a detectable agent or moiety is selected such that it generates a signal which can be measured and whose intensity is related to the amount of bound entity. Methods for labeling proteins and polypeptides, including antibodies, are well-known in the art. Labeled polypeptides can be prepared by incorporation of or conjugation to a label, that is directly or indirectly detectable by spectroscopic, photochemical, biochemical, immunochemical, electrical, optical or chemical means, or any other suitable means. Suitable detectable agents include, but are not limited to, various ligands, radionuclides, fluorescent dyes, chemiluminescent agents, microparticles, enzymes, colorimetric labels, magnetic labels, and haptens.

The terms "approximately" and "about", as used herein in reference to a number, generally include numbers that fall within a range of 10% in either direction of the number (greater than or less than the number) unless otherwise stated or otherwise evident from the context (except where such number would exceed 100% of a possible value).

DETAILED DESCRIPTION OF CERTAIN PREFERRED EMBODIMENTS

As mentioned above, the present invention provides monoclonal antibodies that prevent HCV infection by interfering with HCV-host cells interactions, and hybridoma cell lines which secrete such monoclonal antibodies.

I—Hybridomas and Anti-Claudin-1 Monoclonal Antibodies

As shown in the Examples section below, the present Applicants have produced polyclonal antibodies directed against the extracellular domain of human Claudin-1 by genetic immunization using an expression vector containing the full-length CLDN1 gene. The polyclonal antibodies thus produced were found to efficiently inhibit HCV infection using HCVcc and HCVpp based systems (see Example 1). In view of these encouraging results, the Applicants have used genetic immunization of rats and screening methods to generate hybridoma cell lines which secrete monoclonal antibodies that specifically bind to the extracellular domain of human Claudin-1 and efficiently inhibit HCV infection (see Example 2).

A. Hybridoma Cell Lines and Anti-Claudin-1 Monoclonal Antibodies

Accordingly, the present invention provides hybridoma cell lines which secrete monoclonal antibodies that specifically bind to the extracellular domain of human Claudin-1, and, in particular, to W(30)-GLW(51)-C(54)-C(64), a conserved motif located in the first extracellular loop of Claudin-1. More specifically, the present invention provides eight of such hybridoma cell lines, generated by genetic immunization as described in Example 2 (Lohrmann, 2003). These hybridoma cell lines, which are called OM-4A4-D4, OM-7C8-A8, OM-6D9-A6, OM-7D4-C1, OM-6E1-B5, OM-3E5-B6, OM-8A9-A3, and OM-7D3-B3, were deposited on Jul. 29, 2008 in the DSMZ (Deutsche Sammlung von Mikro-organismen and Zellkuturen GmbH, Inhoffenstraβe 7 B, 38124 Braunschweig, Germany) under Accession Numbers DSM ACC2931, DSM ACC2932, DSM ACC2933, DSM ACC2934, DSM ACC2935, DSM ACC2936, DSM ACC2937, and DSM ACC2938, respectively.

Also provided by the present invention are monoclonal antibodies secreted by any one of these hybridoma cell lines. Methods for the production and isolation of monoclonal antibodies from hybridoma cultures are well known in the art. Hybridoma cells are grown using standard methods, in suitable culture media such as, for example, D-MEM and RPMI-1640 medium. An anti-Claudin-1 monoclonal antibody can be recovered and purified from hybridoma cell cultures by protein A purification, ammonium sulphate or ethanol precipitation, acid extraction, anion or cation exchange chromatography, phosphocellulose chromatography, hydrophobic interaction chromatography, affinity chromatography, such as Protein A column, hydroxylapatite chromatography, lectin chromatography, or any suitable combination of these methods. High performance liquid chromatography (HPLC) can also be employed for purification.

Each of the anti-Claudin-1 monoclonal antibodies secreted by the hybridoma cell lines of the invention was determined to be an immunoglobulin of the rIgG2b heavy (H) chain and kappa light (L) chain isotype or an immunoglobulin of the rIgG2a heavy (H) chain and kappa light (L) chain isotype. However, monoclonal antibodies of the present invention more generally comprise any monoclonal antibody (or fragment thereof), that is secreted by an inventive hybridoma cell line (or a derivatized cell line), and that specifically binds to the extracellular domain of human Claudin-1. Without wishing to be bound by any theory, it is believed that binding of a monoclonal antibody to the extracellular domain of Claudin-1 on a susceptible cell interferes with HCV-host cells interactions, and thereby prevents, inhibits or blocks HCV from entering into the cell and from infecting the cell.

Instead of using the hybridomas described herein as a source of the antibodies, the monoclonal antibodies may be prepared by any other suitable method known in the art. For example, an inventive anti-Claudin-1 monoclonal antibody may be prepared by recombinant DNA methods. These methods generally involve isolation of the genes encoding the desired antibody, transfer of the genes into a suitable vector, and bulk expression in a cell culture system. The genes or DNA encoding the desired monoclonal antibody may be readily isolated and sequenced using conventional procedures (e.g., by using oligonucleotide probes that are capable of binding specifically to genes encoding the heavy and light chains of murine antibodies). The hybridoma cell lines provided herein serve as a preferred source of such DNA. Suitable host cells for recombinant production of monoclonal antibodies include, but are not limited to, appropriate mammalian host cells, such as CHO, HeLa, or CV1. Suitable expression plasmids include, without limitation, pcDNA3.1 Zeo, pIND(SP1), pREP8 (all commercially available from Invitrogen, Carlsbad, Calif., USA), and the like. The antibody genes may be expressed via viral or retroviral vectors, including MLV-based vectors, vaccinia virus-based vectors, and the like. Antibodies of the present invention may be expressed as single chain antibodies. Isolation and purification of recombinantly produced monoclonal antibodies may be performed as described above.

B. Antibody Fragments

In certain embodiments, an inventive monoclonal antibody is used in its native form. In other embodiments, it may be truncated (e.g., via enzymatic cleavage or other suitable method) to provide immunoglobulin fragments or portions, in particular, fragments or portions that are biological active. Biologically active fragments or portions of an inventive monoclonal antibody include fragments or portions that retain the ability of the monoclonal antibody to interfere with HCV-host cells interactions, and/or to specifically bind to the extracellular domain of human Claudin-1, and/or to inhibit or block HCV entry into susceptible cells, and/or to reduce or prevent HCV infection of susceptible cells. Biologically active fragments or portions of inventive monoclonal antibodies described herein are encompassed by the present invention.

A biologically active fragment or portion of an inventive monoclonal antibody may be an Fab fragment or portion, an F(ab')$_2$ fragment or portion, a variable domain, or one or more CDRs (complementary determining regions) of the antibody. Alternatively, a biologically active fragment or portion of an inventive monoclonal antibody may be derived from the carboxyl portion or terminus of the antibody protein and may comprise an Fc fragment, an Fd fragment or an Fv fragment.

Antibody fragments of the present invention may be produced by any suitable method known in the art including, but not limited to, enzymatic cleavage (e.g., proteolytic digestion of intact antibodies) or by synthetic or recombinant techniques. F(ab')$_2$, Fab, Fv and ScFv (single chain Fv) antibody fragments can, for example, be expressed in and secreted from mammalian host cells or from E. coli. Antibodies can also be produced in a variety of truncated forms using antibody genes in which one or more stop codons have been introduced upstream of the natural stop site. The various portions of antibodies can be joined together chemically by conventional techniques, or can be prepared as a contiguous protein using genetic engineering techniques.

C. Fusion Proteins

Antibodies of the present invention (or fragments thereof) may be produced in a modified form, such as a fusion protein (i.e., an immunoglobulin molecule or portion linked to a polypeptide entity). Preferably, fusion proteins of the invention retain the binding capability of the monoclonal antibody towards the extracellular domain of human Claudin-1. A polypeptide entity to be fused to an inventive monoclonal antibody, or a fragment thereof, may be selected to confer any of a number of advantageous properties to the resulting fusion protein. For example, the polypeptide entity may be selected to provide increased expression of the recombinant fusion protein. Alternatively or additionally, the polypeptide entity may facilitate purification of the fusion protein by, for example, acting as a ligand in affinity purification. A proteolytic cleavage site may be added to the recombinant protein so that the desired sequence can ultimately be separated from the polypeptide entity after purification. The polypeptide entity may also be selected to confer an improved stability to the fusion protein, when stability is a goal. Examples of suitable polypeptide entities include, for example, polyhistidine tags, that allow for the easy purification of the resulting fusion protein on a nickel chelating column. Glutathione-S-transferase (GST), maltose B binding protein, or protein A are other examples of suitable polypeptide entities.

Depending on the use intended, an antibody of the invention may be re-engineered so as to optimize stability, solubility, in vivo half-like, or ability to bind additional targets. Genetic engineering approaches as well as chemical modifications to accomplish any or all of these changes in properties are well known in the art. For example, the addition, removal, and/or modification of the constant regions of an antibody are known to play a particularly important role in the bioavailability, distribution, and half-life of therapeutically administered antibodies. The antibody class and subclass, determined by the Fc or constant region of the antibody (which mediates effector functions), when present, imparts important additional properties. Thus, anti-Claudin-1 antibodies with reconfigured, redesigned, or otherwise altered constant domains are encompassed by the present invention.

Additional fusion proteins of the invention may be generated through the techniques of DNA shuffling well known in the art (see, for example, U.S. Pat. Nos. 5,605,793; 5,811,238; 5,830,721; 5,834,252; and 5,837,458). DNA shuffling may be employed to modulate the activity of antibodies, or fragments thereof, for example, to obtain antibodies with higher affinity and lower dissociation rates. In such methods, polynucleotides encoding antibodies of the invention may be altered through random mutagenesis by error-prone PCR, random nucleotide insertion or other methods prior to recombination. Alternatively, one or more portions of a polynucleotide encoding an inventive antibody may be recombined with one or more components, motifs, sections, parts, domains, fragments, etc of one or more heterologous molecules.

Alternatively, an inventive antibody may be linked to another antibody, e.g., to produce a bispecific or a multispecific antibody. For example, an anti-Claudin-1 monoclonal antibody of the present invention, or a biologically active fragment thereof, may be linked to an antibody (or a fragment thereof) that specifically binds to another receptor of HCV on susceptible cells, such as CD81 and SR-BI. Methods for producing bispecific and multispecific antibodies are known in the art and include, for example, chemical synthesis involving cross-linking through reducible disulfide bonds or non-reducible thioether bonds, and recombinant methods.

D. Chimeric/Humanized or De-immunized Antibodies

Anti-Claudin-1 monoclonal antibodies of the present invention can also be "humanized": sequence differences between rodent antibodies and human sequences can be minimized by replacing residues which differ from those in the human sequences by site-directed mutagenesis of individual residues or by grafting of entire regions or by chemical synthesis. Humanized antibodies can also be produced using recombinant methods. In the humanized form of the antibody, some, most or all of the amino acids outside the CDR regions are replaced with amino acids from human immunoglobulin molecules, while some, most or all amino acids within one or more CDR regions are unchanged. Small additions, deletions, insertions, substitutions or modifications of amino acids are permissible as long as they do not abrogate the ability of the resulting antibody to bind to the extracellular domain of human Claudin-1. Suitable human "replacement" immunoglobulin molecules include IgG1, IgG2, IgG2a, IgG2b, IgG3, IgG4, IgA, IgM, IgD or IgE molecules, and fragments thereof. Alternatively, the T-cell epitopes present in rodent antibodies can be modified by mutation (de-immunization) to generate non-immunogenic rodent antibodies that can be applied for therapeutic purposes in humans (see www.accurobio.com).

E. Antibody Conjugates

A monoclonal antibody of the invention, or a biologically active variant or fragment thereof, may be functionally linked (e.g., by chemical coupling, genetic fusion, non-covalent association or otherwise) to one or more other molecular entities. Methods for the preparation of such modified antibodies (or conjugated antibodies) are known in the art. (see, for example, "*Affinity Techniques. Enzyme Purification: Part B*", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32). Preferably, molecular entities are attached at positions on the antibody molecule that do not interfere with the binding properties of the resulting conjugate, i.e., positions that do not participate in the specific binding of the antibody to the extracellular domain of human Claudin-1.

In certain embodiments, the antibody molecule and molecular entity are covalently, directly linked to each other. The direct covalent binding can be through a linkage such as an amide, ester, carbon-carbon, disulfide, carbamate, ether, thioether, urea, amine or carbonate linkage. Covalent binding can be achieved by taking advantage of functional groups present on the antibody and the molecular entity. An activating agent, such as a carbodiimide, can be used to form a direct linkage. In other embodiments, the antibody molecule and the molecular entity are covalently linked to each other through a linker group. This can be accomplished by using any of a wide variety of stable bifunctional agents well known in the art, including homofunctional and heterofunctional linkers.

In certain embodiments, an antibody of the present invention (or a biologically active fragment thereof) is conjugated to a therapeutic moiety. Any of a wide variety of therapeutic moieties may be suitable for use in the practice of the present invention including, without limitation, cytotoxins (e.g., cytostatic or cytocidal agents), therapeutic agents, and radioactive metal ions (e.g., alpha-emitters and alpha-emitters attached to macrocyclic chelators such as DOTA). Cytotoxins or cytotoxc agents include any agent that is detrimental to cells. Examples include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, thymidine kinase, endonuclease, RNAse, and puromycin and fragments, variants or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin and doxorubicin), antibiotics (e.g., dactinomycin, bleomycin, mithramycin, and anthramycin), and anti-mitotic agents (e.g., vincristine and vinblastine). The resulting antibody conjugates may find application in the treatment of liver cancer associated with HCV infection (see below).

Other therapeutic moieties include proteins or polypeptides possessing a desired biological activity. Such proteins include, but are not limited to, toxins (e.g., abrin, ricin A, alpha toxin, pseudomonas exotoxin, diphtheria toxin, saporin, momordin, gelonin, pokeweed antiviral protein, alpha-sarcin and cholera toxin); proteins such as tumor necrosis factor, alpha-interferon, beta-interferon, nerve growth factor, platelet derived growth factor, tissue plasminogen activator; apoptotic agents (e.g., TNF-$\alpha$, TNF-$\beta$) or, biological response modifiers (e.g., lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors).

Alternatively or additionally, an antibody of the present invention (or a biologically active fragment thereof) may be conjugated to a detectable agent. Any of a wide variety of detectable agents can be used in the practice of the present invention, including, without limitation, various ligands, radionuclides (e.g., $^3$H, $^{125}$I, $^{131}$I, and the like), fluorescent dyes (e.g., fluorescein isothiocyanate, rhodamine, phycoerythrin, phycocyanin, allophycocyanin, o-phthalaldehyde and fluorescamine), chemiluminescent agents (e.g., luciferin, luciferase and aequorin), microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available. The resulting detectable antibodies may be used in diagnostic and/or prognostic methods (see below).

Other molecular entities that can be conjugated to an antibody of the present invention (or a biologically active fragment thereof) include, but are not limited to, linear or branched hydrophilic polymeric groups, fatty acid groups, or fatty ester groups.

Thus, in addition to anti-Claudin-1 monoclonal antibodies secreted by the hybridoma cell lines described herein, and any biologically active variants or fragments thereof, the present invention also encompasses chimeric antibodies, humanized antibodies, and antibody-derived molecules comprising at least one complementary determining region (CDR) from either a heavy chain or light chain variable region of an inventive anti-Claudin-1 monoclonal antibody, including molecules such as Fab fragments, F(ab')$_2$ fragments, Fd fragments, Fabc fragments, Sc antibodies (single chain antibodies), diabodies, individual antibody light single chains, individual antibody heavy chains, chimeric fusions between antibody chains and other molecules, and antibody conjugates, such as antibodies conjugated to a diagnostic or therapeutic agent. All these antibodies and antibody-related molecules encompassed by the present invention retain specifically bind to the extracellular domain of human Claudin-1.

F. Activity and Specificity of Inventive Monoclonal Antibodies and Related Molecules Each of the inventive anti-Claudin-1 monoclonal antibodies described in Example 2 was produced from a hybridoma cell line provided herein and was selected for its ability to inhibit HCVcc infection of Huh7.5.1 cells. As will be appreciated by those skilled in the art, the HCV infection inhibitory effect of other antibodies and antibody-related molecules of the invention may also be assessed using a HCVcc infection system. The inhibitory effect of antibodies and antibody-related molecules on HCV infection may, alternatively or additionally, be assessed using retroviral HCV pseudotyped particles (HCVpp) as known in the art. Preferably, an antibody or antibody-related molecule of the present invention will be shown to inhibit HCV infection of susceptible cells by HCVcc or HCVpp in a dose-dependent manner.

Other methods that can be used for testing the specificity of antibodies and reagents of the present invention include, but are not limited to, flow cytometry analysis, Western blot analysis, ELISA and inhibiting binding assays involving ligand/receptor binding by the antibody. These methods can be used for testing supernatants from hybridomas producing antibodies, for testing the activity of isolated/purified antibodies, and/or for testing the activity of modified antibodies (antibody-related molecules). Binding specificity testing may be performed using the antibody or antibody-related molecule against a panel of cells, e.g., human cells, including, without limitation, liver cell lines (such as, for example, Huh7, Hep3b or HepG2), embryonic kidney cells (293T), fibroblasts (HeLa), B cells, T cells (e.g., Molt-4, Sup-TI, or Hut-78), monocytic cells (THP-I), astrocytic cells (U87), hepatoma cells (PLC/PRF:5) or other liver cell types, e.g., the liver adenocarcinoma SkHepI, human peripheral blood cells and various fractionated subtypes thereof including lymphocytes and monocytes or other cell lines including CaCo2 cells. Flow cytometry analysis can reveal binding specificity of the antibody or antibody-related molecule for Claudin-1 on various cell types. Cells from non-human mammals may also be used in such assays.

Using such assays, IC50 values may be determined for the antibodies and antibody-related molecules of the present invention. These values, which give an indication of the concentration of antibody or antibody-related molecule required for 50% inhibition of viral infectivity, provide meaningful and significant quantitative criteria and allow comparison of the infection inhibiting activity of different antibodies and antibody-related molecules.

The inventive anti-Claudin-1 monoclonal antibodies described in Example 2 have been found to potently cross-neutralize HCV infection from all major genotypes as well as all isolates of the entire quasispecies population from two chronically HCV infected patients. The ability of other antibodies and antibody-related molecules of the invention to cross-neutralize HCV infection from major HCV genotypes and from isolates of quasispecies of individual patients may be assessed using any suitable method such as by using HCV pseudotyped particles (HCVpp) bearing HCV envelope glycoproteins from a specific HCV genotype, or HCVpp bearing HCV envelope glycoproteins from an individual patient chronically infected with HCV, as described in Example 2. Preferably, an antibody or antibody-related molecule of the present invention will be shown to inhibit HCV infection from major HCV genotypes and from quasispecies of an HCV-infected patient in a dose-dependent manner.

Similarly, an antibody or antibody-related molecule of the present invention has been shown not to cross-react with rodent Claudin-1 (such as murine Claudin-1) but to specifically bind to non-human primate Claudin-1 (such as cynomolgus monkey Claudin-1).

II—Treatment or Prevention of HCV Infection and HCV-associated Diseases

A. Indications

Anti-Claudin-1 antibodies of the present invention may be used in therapeutic and prophylactic methods to treat and/or prevent HCV infection, or to treat and/or prevent a liver disease or a pathological condition affecting HCV-susceptible cells, such as liver cells, lymphoid cells, or monocytes/macrophages. An inventive anti-Claudin-1 antibody interferes with HCV-host cells interactions by binding to the extracellular domain of Claudin-1 on a cell surface, thereby reducing, inhibiting, blocking or preventing HCV entry into the cell and/or HCV infection of the cell.

Methods of treatment of the present invention may be accomplished using an inventive antibody or a pharmaceutical composition comprising an inventive antibody (see below). These methods generally comprise administration of an effective amount of at least one inventive anti-Claudin-1 antibody, or a pharmaceutical composition thereof, to a subject in need thereof. Administration may be performed using any of the methods known to one skilled in the art. In particular, the antibody or composition may be administered by various routes including, but not limited to, aerosol, parenteral, oral or topical route.

In general, an inventive antibody or composition will be administered in an effective amount, i.e. an amount that is sufficient to fulfill its intended purpose. The exact amount of antibody or pharmaceutical composition to be administered will vary from subject to subject, depending on the age, sex, weight and general health condition of the subject to be treated, the desired biological or medical response (e.g., prevention of HCV infection or treatment of HCV-associated liver disease), and the like. In many embodiments, an effective amount is one that inhibits or prevents HCV from entering into a subject's susceptible cells and/or infecting a subject's cells, so as to thereby prevent HCV infection, treat or prevent liver disease or another HCV-associated pathology in the subject.

Antibodies and compositions of the present invention may be used in a variety of therapeutic or prophylactic methods. In particular, the present invention provides a method for treating or preventing a liver disease or pathology in a subject, which comprises administering to the subject an effective amount of an inventive antibody (or composition thereof) which inhibits HCV from entering or infecting the subject's cells, so as to thereby treat or prevent the liver disease or pathology in the subject. The liver disease or pathology may be inflammation of the liver, liver fibrosis, cirrhosis, and/or hepatocellular carcinoma (i.e., liver cancer) associated with HCV infection.

The present invention also provides a method for treating or preventing a HCV-associated disease or condition (including a liver disease) in a subject, which comprises administering to the subject an effective amount of an inventive antibody (or composition thereof) which inhibits HCV from entering or infecting the subject's cells, so as to thereby treat or prevent the HCV-associated disease or condition in the subject. In certain embodiments of the present invention, the antibody or composition is administered to a subject diagnosed with acute hepatitis C. In other embodiments of the invention, the antibody or composition is administered to a subject diagnosed with chronic hepatitis C.

Administration of an inventive antibody or composition according to such methods may result in amelioration of at least one of the symptoms experienced by the individual including, but not limited to, symptoms of acute hepatitis C such as decreased appetite, fatigue, abdominal pain, jaundice, itching, and flu-like symptoms; symptoms of chronic hepatitis C such as fatigue, marked weight loss, flu-like symptoms, muscle pain, joint pain, intermittent low-grade fevers, itching, sleep disturbances, abdominal pain, appetite changes, nausea, diarrhea, dyspepsia, cognitive changes, depression, headaches, and mood swings; symptoms of cirrhosis such as ascites, bruising and bleeding tendency, bone pain, varices (especially in the stomach and esophagus), steatorrhea, jaundice and hepatic encephalopathy; and symptoms of extrahepatic manifestations associated with HCV such as thyroiditis, porphyria cutanea tarda, cryoglobulinemia, glomerulonephritis, sicca syndrome, thrombocytopenia, lichen planus, diabetes mellitus and B-cell lymphoproliferative disorders.

Alternatively or additionally, administration of an inventive antibody or composition according to such methods may slow, reduce, stop or alleviate the progression of HCV infection or an HCV-associated disease, or reverse the progression to the point of eliminating the infection or disease. Administration of an inventive antibody or composition according to such methods may also result in a reduction of the number of viral infections, reduction of the number of infectious viral particles, and/or reduction in the number of virally infected cells.

The effects of a treatment according to the invention may be monitored using any of the assays known in the art for the diagnosis of HCV infection and/or liver disease. Such assays include, but are not limited to, serological blood tests, liver function tests to measure one or more of albumin, alanine transaminase (ALT), alkaline phosphatase (ALP), aspartate transaminase (AST), and gamma glutamyl transpeptidase (GGT), and molecular nucleic acid tests using different techniques such as polymerase chain reaction (PCR), transcription mediated amplification (TMA), or branched DNA (bDNA).

Antibodies and compositions of the present invention may also be used in immunization therapies. Accordingly, the present invention provides a method of reducing the likelihood of susceptible cells of becoming infected with HCV as a result of contact with HCV. The method comprises contacting the susceptible cells with an effective amount of an inventive antibody or composition which inhibits HCV from entering or infecting the susceptible cells, so as to reduce the likelihood of the cells to become infected with HCV as a result of contact with HCV. The present invention also provides a method of reducing the likelihood of a subject's susceptible cells of becoming infected with HCV as a result of contact with HCV. In this method, contacting the susceptible cells with the inventive antibody or composition may be performed by administrating the antibody or composition to the subject.

Reducing the likelihood of susceptible cells or of a subject of becoming infected with HCV means decreasing the probability of susceptible cells or a subject to become infected with HCV as a result of contact with HCV. The decrease may be of any significant amount, e.g., at least a 2-fold decrease, more than a 2-fold decrease, at least a 10-fold decrease, more than a 10-fold decrease, at least a 100-fold decrease, or more than a 100-fold decrease.

In certain embodiments, the subject is infected with HCV prior to administration of the inventive antibody or composition. In other embodiments, the subject is not infected with HCV prior to administration of the inventive antibody or composition. In yet other embodiments, the subject is not infected with, but has been exposed to, HCV. In certain embodiments, the subject may be infected with HIV or HBV.

For example, the methods of the present invention may be used to reduce the likelihood of a subject's susceptible cells of becoming infected with HCV as a result of liver transplant. As already mentioned above, when a diseased liver is removed from a HCV-infected patient, serum viral levels plummet. However, after receiving a healthy liver transplant, virus levels rebound and can surpass pre-transplant levels within a few days (Powers, 2006). Liver transplant patients may benefit from administration of an inventive antibody that binds to the ectodomain of Claudin-1 on the surface of hepatocytes and thereby reduce, inhibit, block or prevent HCV entry into the cells. Administration may be performed prior to liver transplant, during liver transplant, and/or following liver transplant.

Other subjects that may benefit from administration of an inventive antibody or composition include, but are not limited to, babies born to HCV-infected mothers, in particular if the mother is also HIV-positive; health-care workers who have been in contact with HCV-contaminated blood or blood contaminated medical instruments; drug users who have been exposed to HCV by sharing equipments for injecting or otherwise administering drugs; and people who have been exposed to HCV through tattooing, ear/body piercing and acupuncture with poor infection control procedures.

Other subjects that may benefit from administration of an inventive antibody or composition include, but are not limited to, subjects that exhibit one or more factors that are known to increase the rate of HCV disease progression. Such factors include, in particular, age, gender (males generally exhibit more rapid disease progression than females), alcohol consumption, HIV co-infection (associated with a markedly increased rate of disease progression), and fatty liver.

In certain embodiments, an inventive antibody or composition is administered alone according to a method of treatment of the present invention. In other embodiments, an inventive antibody or composition is administered in combination with at least one additional therapeutic agent. The inventive antibody or composition may be administered prior to administration of the therapeutic agent, concurrently with the therapeutic agent, and/or following administration of the therapeutic agent.

Therapeutic agents that may be administered in combination with an inventive antibody or composition may be selected among a large variety of biologically active compounds that are known to have a beneficial effect in the treatment or prevention of HCV infection, or a HCV-associated disease or condition. Such agents include, in particular, antiviral agents including, but not limited to, interferons (e.g., interferon-alpha, pegylated interferon-alpha), ribavirin, anti-HCV (monoclonal or polyclonal) antibodies, RNA polymerase inhibitors, protease inhibitors, IRES inhibitors, helicase inhibitors, antisense compounds, ribozymes, and any combination thereof.

B. Administration

An inventive antibody, (optionally after formulation with one or more appropriate pharmaceutically acceptable carriers or excipients), in a desired dosage can be administered to a subject in need thereof by any suitable route. Various delivery systems are known and can be used to administer antibodies of the present invention, including tablets, capsules, injectable solutions, encapsulation in liposomes, microparticles, microcapsules, etc. Methods of administration include, but are not limited to, dermal, intradermal, intramuscular, intraperitoneal, intralesional, intravenous, subcutaneous, intranasal, pulmonary, epidural, ocular, and oral routes. An inventive antibody or composition may be administered by any convenient or other appropriate route, for example, by infusion or bolus injection, by absorption through epithelial or mucocutaneous linings (e.g., oral, mucosa, rectal and intestinal mucosa, etc). Administration can be systemic or local. Parenteral administration may be preferentially directed to the patient's liver, such as by catheterization to hepatic arteries or into a bile duct. As will be appreciated by those of ordinary skill in the art, in embodiments where an inventive antibody is administered in combination with an additional therapeutic agent, the antibody and therapeutic agent may be administered by the same route (e.g., intravenously) or by different routes (e.g., intravenously and orally).

C. Dosage

Administration of an inventive antibody (or composition) of the present invention will be in a dosage such that the amount delivered is effective for the intended purpose. The route of administration, formulation and dosage administered will depend upon the therapeutic effect desired, the severity of the HCV-related condition to be treated if already present, the presence of any infection, the age, sex, weight, and general health condition of the patient as well as upon the potency, bioavailability, and in vivo half-life of the antibody or composition used, the use (or not) of concomitant therapies, and other clinical factors. These factors are readily determinable by the attending physician in the course of the therapy. Alternatively or additionally, the dosage to be administered can be determined from studies using animal models (e.g., chimpanzee or mice). Adjusting the dose to achieve maximal efficacy based on these or other methods are well known in the art and are within the capabilities of trained physicians. As studies are conducted using the inventive monoclonal antibodies, further information will emerge regarding the appropriate dosage levels and duration of treatment.

A treatment according to the present invention may consist of a single dose or multiple doses. Thus, administration of an inventive antibody, or composition thereof, may be constant for a certain period of time or periodic and at specific intervals, e.g., hourly, daily, weekly (or at some other multiple day interval), monthly, yearly (e.g., in a time release form). Alternatively, the delivery may occur at multiple times during a given time period, e.g., two or more times per week; two or more times per month, and the like. The delivery may be continuous delivery for a period of time, e.g., intravenous delivery.

In general, the amount of monoclonal antibody administered will preferably be in the range of about 1 ng/kg to about 100 mg/kg body weight of the subject, for example, between about 100 ng/kg and about 50 mg/kg body weight of the subject; or between about 1 µg/kg and about 10 mg/kg body weight of the subject, or between about 100 µg/kg and about 1 mg/kg body weight of the subject.

III—Pharmaceutical Compositions

As mentioned above, anti-Claudin-1 antibodies (and related molecules) of the invention may be administered per se or as a pharmaceutical composition. Accordingly, the present invention provides pharmaceutical compositions comprising an effective amount of an inventive antibody described herein and at least one pharmaceutically acceptable carrier or excipient. In some embodiments, the composition further comprises one or more additional biologically active agents.

Inventive antibodies and pharmaceutical compositions may be administered in any amount and using any route of administration effective for achieving the desired prophylactic and/or therapeutic effect. The optimal pharmaceutical formulation can be varied depending upon the route of administration and desired dosage. Such formulations may influence the physical state, stability, rate of in vivo release, and rate of in vivo clearance of the administered active ingredient.

The pharmaceutical compositions of the present invention may be formulated in dosage unit form for ease of administration and uniformity of dosage. The expression "unit dosage form", as used herein, refers to a physically discrete unit of an inventive anti-Claudin-1 antibody for the patient to be treated. It will be understood, however, that the total daily dosage of the compositions will be decided by the attending physician within the scope of sound medical judgement.

A. Formulation

Injectable preparations, for example, sterile injectable aqueous or oleaginous suspensions may be formulated according to the known art using suitable dispersing or wetting agents, and suspending agents. The sterile injectable preparation may also be a sterile injectable solution, suspension or emulsion in a non-toxic parenterally acceptable diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspending medium. For this purpose any bland fixed oil can be employed including synthetic mono- or di-glycerides. Fatty acids such as oleic acid may also be used in the preparation of injectable formulations. Sterile liquid carriers are useful in sterile liquid form compositions for parenteral administration.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Liquid pharmaceutical compositions which are sterile solutions or suspensions can be administered by, for example, intravenous, intramuscular, intraperitoneal or subcutaneous injection. Injection may be via single push or by gradual infusion. Where necessary or desired, the composition may include a local anesthetic to ease pain at the site of injection.

In order to prolong the effect of an active ingredient (here an inventive anti-Claudin-1 antibody), it is often desirable to slow the absorption of the ingredient from subcutaneous or intramuscular injection. Delaying absorption of a parenterally administered active ingredient may be accomplished by dissolving or suspending the ingredient in an oil vehicle. Injectable depot forms are made by forming micro-encapsulated matrices of the active ingredient in biodegradable polymers such as polylactide-polyglycolide. Depending upon the ratio of active ingredient to polymer and the nature of the particular polymer employed, the rate of ingredient release can be controlled. Examples of other biodegradable polymers include poly(orthoesters) and poly(anhydrides). Depot injectable formulations can also be prepared by entrapping the active ingredient in liposomes or microemulsions which are compatible with body tissues.

Liquid dosage forms for oral administration include, but are not limited to, pharmaceutically acceptable emulsions, microemulsions, solutions, suspensions, syrups, elixirs, and pressurized compositions. In addition to the anti-Claudin-1 antibody, the liquid dosage form may contain inert diluents commonly used in the art such as, for example, water or other solvent, solubilising agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols, and fatty acid esters of sorbitan and mixtures thereof. Besides inert diluents, the oral compositions can also include adjuvants such as wetting agents, suspending agents, preservatives, sweetening, flavouring, and perfuming agents, thickening agents, colors, viscosity regulators, stabilizes or osmoregulators. Examples of suitable liquid carriers for oral administration include water (potentially containing additives as above, e.g., cellulose derivatives, such as sodium carboxymethyl cellulose solution), alcohols (including monohydric alcohols and polyhydric alcohols such as glycols) and their derivatives, and oils (e.g., fractionated coconut oil and arachis oil). For pressurized compositions, the liquid carrier can be halogenated hydrocarbon or other pharmaceutically acceptable propellant.

Solid dosage forms for oral administration include, for example, capsules, tablets, pills, powders, and granules. In such solid dosage forms, an inventive anti-Claudin-1 antibody may be mixed with at least one inert, physiologically acceptable excipient or carrier such as sodium citrate or dicalcium phosphate and one or more of: (a) fillers or extenders such as starches, lactose, sucrose, glucose, mannital, and silicic acid; (b) binders such as, for example, carboxymethylcellulose, alginates, gelatine, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; absorption accelerators such as quaternary ammonium compounds; (g) wetting agents such as, for example, cetyl alcohol and glycerol monostearate; (h) absorbents such as kaolin and bentonite clay; and (i) lubricants such as talc, calcium stearate, magnesium stearate, solid polyethylene glycols, sodium lauryl sulphate, and mixtures thereof. Other excipients suitable for solid formulations include surface modifying agents such as non-ionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. In the case of capsules, tablets and pills, the dosage form may also comprise buffering agents.

Solid compositions of a similar type may also be employed as fillers in soft and hard-filled gelatine capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition such that they release the active ingredient(s) only, or preferably, in a certain part of the intestinal tract, optionally, in a delaying manner. Examples of embedding compositions which can be used include polymeric substances and waxes.

In certain embodiments, it may be desirable to administer an inventive composition locally to an area in need of treatment (e.g., the liver). This may be achieved, for example, and not by way of limitation, by local infusion during surgery (e.g., liver transplant), topical application, by injection, by means of a catheter, by means of suppository, or by means of a skin patch or stent or other implant.

For topical administration, the composition is preferably formulated as a gel, an ointment, a lotion, or a cream which can include carriers such as water, glycerol, alcohol, propylene glycol, fatty alcohols, triglycerides, fatty acid esters, or mineral oil. Other topical carriers include liquid petroleum, isopropyl palmitate, polyethylene glycol, ethanol (95%), polyoxyethylenemonolaurat (5%) in water, or sodium lauryl sulphate (5%) in water. Other materials such as antioxidants, humectants, viscosity stabilizers, and similar agents may be added as necessary.

In addition, in certain instances, it is expected that the inventive compositions may be disposed within transdermal devices placed upon, in, or under the skin. Such devices include patches, implants, and injections which release the active ingredient by either passive or active release mechanisms. Transdermal administrations include all administration across the surface of the body and the inner linings of bodily passage including epithelial and mucosal tissues. Such administrations may be carried out using the present compositions in lotions, creams, foams, patches, suspensions, solutions, and suppositories (rectal and vaginal).

Transdermal administration may be accomplished through the use of a transdermal patch containing an active ingredient (i.e., an inventive anti-Claudin-1 antibody) and a carrier that is non-toxic to the skin, and allows the delivery of the ingredient for systemic absorption into the bloodstream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may be suitable. A variety of occlusive devices may be used to release the active ingredient into the bloodstream such as a semi-permeable membrane covering a reservoir containing the active ingredient with or without a carrier, or a matrix containing the active ingredient.

Suppository formulations may be made from traditional materials, including cocoa butter, with or without the addition of waxes to alter the suppository's melting point, and glycerine. Water soluble suppository bases, such as polyethylene glycols of various molecular weights, may also be used.

When a pharmaceutical composition of the present invention is used as "vaccine" to prevent HCV-susceptible cells to become infected with HCV, the pharmaceutical composition may further comprise vaccine carriers known in the art such as, for example, thyroglobulin, albumin, tetanus toxoid, and polyamino acids such as polymers of D-lysine and D-glutamate. The vaccine may also include any of a variety of well known adjuvants such as, for example, incomplete Freund's adjuvant, alum, aluminium phosphate, aluminium hydroxide, monophosphoryl lipid A (MPL, GlaxoSmithKline), a saponin, CpG oligonucleotides, montanide, vitamin A and various water-in-oil emulsions prepared from biodegradable oils such as squalene and/or tocopherol, Quil A, Ribi Detox, CRL-1005, L-121 and combinations thereof.

Materials and methods for producing various formulations are known in the art and may be adapted for practicing the subject invention. Suitable formulations for the delivery of antibodies can be found, for example, in "*Remington's Pharmaceutical Sciences*", E. W. Martin, $18^{th}$ Ed., 1990, Mack Publishing Co.: Easton, Pa.

B. Additional Biologically Active Agents

In certain embodiments, an inventive anti-Claudin-1 antibody is the only active ingredient in a pharmaceutical composition of the present invention. In other embodiments, the pharmaceutical composition further comprises one or more biologically active agents. Examples of suitable biologically active agents include, but are not limited to, vaccine adjuvants and therapeutic agents such as anti-viral agents (as described above), anti-inflammatory agents, immunomodulatory agents, analgesics, antimicrobial agents, antibacterial agents, antibiotics, antioxidants, antiseptic agents, and combinations thereof.

In such pharmaceutical compositions, the anti-Claudin-1 antibody and additional therapeutic agent(s) may be combined in one or more preparations for simultaneous, separate or sequential administration of the anti-Claudin-1 antibody and therapeutic agent(s). More specifically, an inventive composition may be formulated in such a way that the antibody and therapeutic agent(s) can be administered together or independently from each other. For example, an anti-Claudin-1 antibody and a therapeutic agent can be formulated together in a single composition. Alternatively, they may be maintained (e.g., in different compositions and/or containers) and administered separately.

C. Pharmaceutical Packs of Kits

In another aspect, the present invention provides a pharmaceutical pack or kit comprising one or more containers (e.g., vials, ampoules, test tubes, flasks or bottles) containing one or more ingredients of an inventive pharmaceutical composition, allowing administration of an anti-Claudin-1 antibody of the present invention.

Different ingredients of a pharmaceutical pack or kit may be supplied in a solid (e.g., lyophilized) or liquid form. Each ingredient will generally be suitable as aliquoted in its respective container or provided in a concentrated form. Pharmaceutical packs or kits may include media for the reconstitution of lyophilized ingredients. Individual containers of the kits will preferably be maintained in close confinement for commercial sale.

In certain embodiments, a pharmaceutical pack or kit includes one or more additional therapeutic agent(s) (e.g., one or more anti-viral agents, as described above). Optionally associated with the container(s) can be a notice or package insert in the form prescribed by a governmental agency regulating the manufacture, use or sale of pharmaceutical or biological products, which notice reflects approval by the agency of manufacture, use or sale for human administration. The notice of package insert may contain instructions for use of a pharmaceutical composition according to methods of treatment disclosed herein.

An identifier, e.g., a bar code, radio frequency, ID tags, etc., may be present in or on the kit. The identifier can be used, for example, to uniquely identify the kit for purposes of quality control, inventory control, tracking movement between workstations, etc.

IV—Non-Therapeutic Uses of Anti-Claudin-1 Monoclonal Antibodies

Antibodies of the present invention, e.g., an anti-claudin-1 monoclonal antibody produced by a hybridoma cells line provided herein, may be employed in a variety of non-therapeutic applications, such as purification, screening and diagnostic methods.

A. Purification Methods

Thus, antibodies of the invention may be used as affinity purification agents. In this application, an inventive antibody is immobilized on a solid phase such as Sephadex resin or filter paper, using methods well known in the art. The immobilized antibody is contacted with a sample containing human Claudin-1 (or a fragment thereof) to be purified, and thereafter the support is washed with a suitable solvent that will remove substantially all the material in the sample except the Claudin-1 protein, which is bound to the immobilized antibody. Finally, the support is washed with another suitable solvent which will release the Claudin-1 protein from the antibody.

B. Screening Methods

Anti-Claudin-1 antibodies of the present invention may also be used in drug screening methods based on competitive binding assays. Such methods may involve the steps of allowing competitive binding between a test compound (e.g., a test antibody) in a sample and a known amount of an inventive anti-Claudin-1 monoclonal antibody, for binding to cells to which the inventive antibody binds, and measuring the amount of the known monoclonal antibody bound. The inventive monoclonal antibody is appropriately labeled, for example, with an enzymatic, chemiluminescent, or fluorescent label.

C. Diagnostic Methods

Anti-Claudin-1 antibodies of the present invention may also be useful in diagnostic and/or prognostic assays, in particular for the diagnosis and/or prognosis of different cancers, e.g., by detecting the expression of Claudin-1 in specific cells, tissues, or serum. Thus, for example, decreased expression of claudin-1 has been shown to be a strong predictor of colon cancer recurrence and poor patient survival in stage 11 colon cancer (Resnick, 2005); increased expression of Claudin-1 is a good diagnostic marker for the detection of cervical intraepithelial neoplasia (Sobel, 2005) and has been reported to be a useful marker for malignant transformation of cervical squamous cells (Lee, 2005); decreased expression of Claudin-1 correlates with high tumor grade and biochemical disease recurrence in prostatic adenocarcinoma (Sheeban, 2007); decreased expression of Claudin-1 has been demonstrated to correlate with recurrence status and malignant potential of breast cancer (Morohashi, 2007).

Diagnosis and/or prognosis assays of the present invention generally comprise contacting a biological sample obtained from a patient with an inventive anti-claudin-1 antibody for a time and under conditions allowing an antibody-Claudin-1 complex to form between the antibody and claudin-1 present in the biological sample; and detecting (and/or quantitating) the presence or absence of any antibody-Claudin-1 complex formed. The presence or quantity determined may be used as an indication of the presence of a given condition (e.g., a cancer). In certain methods, the quantity measured is compared to the quantity of antibody-Claudin-1 complex formed under the same conditions for a biological sample obtained from a healthy subject (or from a series of biological samples obtained from a significant number of healthy subjects).

These methods may be applied to the study of any type of biological samples. Examples of suitable biological samples include, but are not limited to, whole blood, urine, serum, plasma, saliva, synovial fluid, seminal fluid, lymphatic fluid, cerebrospinal fluid, peritoneal fluid, as well as endocervical, uretral, rectal, and vaginal samples. Biological samples may include sections of tissue (e.g., breast biopsy samples), frozen sections, and archival samples with known diagnosis, treatment and/or outcome history. Biological samples may be collected by any non-invasive means, such as, for example, by drawing blood from a subject, or using fine needle aspiration or biopsy.

The diagnostic methods may be performed on the biological sample itself without, or with limited, processing of the sample. Alternatively, they may be performed after processing of the biological sample. Processing of a biological sample may involve one or more of: filtration, distillation, centrifugation, extraction, concentration, dilution, purification, inactivation of interfering components, addition of reagents, and the like. For example, the method of diagnostic may be performed on a protein extract prepared from the biological sample. Methods of protein extraction are well known in the art.

In the diagnostic methods described above, detection of an antibody-Claudin-1 complex may be carried out by any suitable method (see, for example, E. Harlow and A. Lane, "*Antibodies: A Laboratories Manual*", 1988, Cold Spring Harbor Laboratory: Cold Spring Harbor, N.Y.). For example, detection of an antibody-Claudin-1 complex may be performed using an immunoassay. A wide range of immunoassay techniques is available, including radioimmunoassay, enzyme immunoassays (EIA), enzyme-linked immunosorbent assays (ELISA), and immunofluorescence immunoprecipitation. Immunoassays are well known in the art. Methods for carrying out such assays as well as practical applications and procedures are summarized in textbooks (see, for example, P. Tijssen, In: Practice and theory of enzyme immunoassays, eds. R. H. Burdon and v. P. H. Knippenberg, Elsevier, Amsterdam (1990), pp. 221-278 and various volumes of Methods in Enzymology, Eds. S. P. Colowick et al., Academic Press, dealing with immunological detection methods, especially volumes 70, 73, 74, 84, 92 and 121). Immunoassays may be competitive or non-competitive.

In certain embodiments, the inventive antibody is immobilized by being either covalently or passively bound to the surface of solid carrier or support. The solid support is any solid support known in the art to which the antibody can be operably affixed; Operably affixed refers to the antibody being affixed in a manner permitting the formation of a complex between the affixed antibody and the extracellular domain of Claudin-1. Examples of suitable carrier or support materials include, but are not limited to, agarose, cellulose, nitrocellulose, dextran, Sephadex, Sepharose, carboxymethyl cellulose, polyacrylamides, polystyrene, polyvinyl chloride, polypropylene, gabbros, magnetic, ion-exchange resin, glass, polyamine-methyl-vinyl-ether-maleic acid copolymer, amino acid copolymer, ethylene-maleic acid copolymer, nylon, silk, and the like. Immobilization of an antibody on the surface of a solid carrier or support may involve crosslinking, covalent binding or physical adsorption, using methods well known in the art. The solid carrier or support may be in the form of a bead, a particle, a microplate well, an array, a cuvette, a tube, a membrane or any other shape suitable for condition an immunoassay. In certain embodiments, immobilization of an antigen to a solid carrier or support includes gel electrophoresis followed by transfer to a membrane (typically nitrocellulose or PVDF) in a process called western blotting (or immunoblot) well known in the art.

D. Diagnostic Kits

The present invention also provides kits comprising materials, including at least one inventive anti-Claudin-1 monoclonal antibody, useful for carrying out the screening or diagnostic methods described above. Preferably, the kit comprises a combination of reagents in predetermined amounts with instructions for performing one of the methods. In embodiments where the antibody is labelled with an enzyme, the kit will include substrates and cofactors required by the enzyme (e.g., a substrate precursor which provides the detectable chromophore or fluorophore). In addition, other additives may be included such as stabilizers, buffers (e.g. a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration. The antibody may or may not be immobilized on a substrate surface (e.g., beads, array and the like). The kits may also contain a notice in the form prescribed by a governmental agency regulating the manufacture, use or sale of pharmaceuticals or biological products.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data are actually obtained.

Some of the results reported below for polyclonal antisera were presented at the 15$^{th}$ International Symposium on Hepatitis C Virus and Related Viruses (San Antonio, Tex., USA, 5-9 Oct., 2008) and are summarized in an Abstract entitled "Production of anti-claudin1 antibodies potently inhibiting HCV infection reveals that Claudin-1 is required for an entry step closely linked to SR-BI and CD81" by S. Krieger et al. Other results are presented in S. Krieger et al., "Inhibition of hepatitis C virus infection by anti-Claudin antibodies is mediated by inhibition of E2-CD81-CLDN1 association", which has been submitted for publication in August 2009 as well as S. Krieger et al., "Monoclonal anti-claudin-1 antibodies for prevention and treatment of hepatitis C virus infection", which will be submitted for publication in October 2009.

Example 1

Polyclonal Antibodies Against Human Claudin 1

Materials and Methods

Cells. Chinese hamster ovary cells (CHO), BOSC23 cells, and Huh7.5.1 hepatoma cells used in the present studies have been described (Barth, 2005; Barth, 2003; Bartosch, 2003; Blight, 2002). BOSC23 cells are HEK293-derived ecotropic packaging cells which do not express endogenous CLDN1 (Pear, 1993). Primary human hepatocytes were isolated and cultured as described by David, 1998 (which is incorporated herein by reference in its entirety).

Production of Anti-CLDN1 Polyclonal Antibodies. Antibodies directed against the extracellular loop of human Claudin-1 were raised by genetic immunization of Wistar rats using a pcCMVSport 6-expression vector containing the full-length human CLDN-1 cDNA (pcDNA CLDN-1). In brief, animals received five applications of pcDNA CLDN-1, intradermally at 2-week intervals. Pre-immune control serum was collected from the same animal bled before immunization. To analyze the specificity of the produced anti-CLDN-1 polyclonal serum, BOSC23 or CHO cells were transfected with pcDNA (control vector) or pcDNA CLDN-1 using liposome-mediated gene transfer (Lipofectamine; Invitrogen, Karlsruhe, Germany) according to the manufacturer's protocol. BOSC23 or CHO cells were then incubated with anti-CLDN-1 polyclonal serum or pre-immune control serum and analyzed for cell surface CLDN-1 expression by flow cytometry as previously described (Barth, 2005).

Characterization of Anti-CLDN1 Polyclonal Antibodies by Immunofluorescence. Caco2 cells and Huh7.5.1 cells were seeded onto glass coverslips, fixed with 3% paraformaldehyde in PBS for 20 minutes, and stained for CLDN1 using anti-CLDN1 antibodies directed against the CLDN1 ectodomains (i.e., inventive polyclonal antibodies, "anti-CLDN1 pAb", 50 μg/mL of rat anti-CLDN1 IgG), an anti-CLDN1 antibody directed against the intracellular C-terminal domain ("anti-CLDN1 mAb", clone 105-D9, Abnova), and for the nucleus using DAPI (4',6'-diamidino-2-phenylindole). Control rat polyclonal IgG ("control pAb") and mouse monoclonal IgG ("control mAb") were used as controls. Bound primary antibodies were visualized using anti-rat-Cy5 and anti-mouse Alexa Fluor® 488 secondary antibodies and a Zeiss Axio Observer microscope (Carl Zeiss S. A. S, Le Pecq, France).

Production of Recombinant HCV and Infection Assays. Plasmids pFK-Jc1 (Pietschmann, 2006) encode the full length HCV JFH1 cDNA or the chimeric HCV genome designated Jc1 which consists of H6CF and JFH1 segments. In vitro HCV RNA synthesis and RNA transfection was carried out as described (Wakita, 2005). Culture supernatants from transfected cells were cleared and concentrated as previously described using Amicon Ultra 15 (Millipore, Billerica, Mass., USA) and used directly or were stored at 4° C. or −80° C.

Viruses were titered by using the limiting dilution assay on Huh7.5.1 cells with a few minor modifications and TCID50 (the 50% tissue culture infective dose) was calculated based on the method described by Lindenbach, 2005. Huh7.5.1 cells were mixed with anti-CLDN-1 or control serum (starting at a concentration of 5 µg/mL to 100 µg/mL) and pre-incubated for 1 hour at 37° C. HCVcc were added and incubated for 16 hours at 37° C. The supernatants were removed and cells incubated in regular medium for 72 hours at 37° C. and HCV infection was determined by qRT-PCR of intracellular HCV RNA as described. Antibody-mediated neutralization was assessed by the specific infectivity.

Production of Retroviral HCV Pseudoparticles and Antibody-mediated Inhibition of HCVpp Infection. HCVpp bearing envelope proteins from strain H77 or other strains and VSVpp were generated as described (Bartosch, 2003). HCVpp without envelope glycoproteins (control pp) served as negative control. For the study of antibody-mediated neutralization, Huh7.5.1 cells were seeded the day before infection assays in 96-well plates at a density of $0.5 \times 10^4$ cells/well. Huh7.5.1 cells were mixed with anti-CLDN-1 or control serum (starting at a dilution of 1/20) and pre-incubated for 1 hour at 37° C. The supernatants were removed and cells incubated in regular medium for 72 hours at 37° C. HCV entry was determined by analysis of Luciferase reporter gene expression as described. Antibody-mediated neutralization was assessed by the specific infectivity of HCVpp in the presence of anti-claudin1 serum or pre-immune serum.

Results

Production of Polyclonal Antibodies Directed against the Extracellular Loop of Claudin-1 Expressed on BOSC23 or CHO cells Expressing Claudin-1. To assess the function role of CLDN-1 in the initiation of HCV infection, rat polyclonal anti-CLDN-1 sera directed against the extracellular loop of CLDN-1 were first generated by genetic immunization as described above. Following completion of immunization, antibodies were selected for their ability to bind to human CLDN-1 expressed on the cell surface of non-permeabilized transfected BOSC23 or CHO cells. As shown in FIG. 1, incubation of CHO cells expressing human CLDN-1 with rat polyclonal anti-CLDN-1 antibodies resulted in specific interaction of the serum with the extracellular ectodomain of CLDN-1 (FIG. 1B). In contrast, no interaction was seen in CHO cells transfected with the pcDNA3.1 control vector and incubated with rat anti-CLDN-1 serum or in CHO cells incubated with human CLDN-1 expressing cDNA and incubated with rat pre-immune serum (FIG. 1A).

To study whether anti-human CLDN-1 recognizes CLDN-1 on cells susceptible to HCV infection, human hepatocytes and Huh7.5.1 hepatoma cells were incubated with the sera and analyzed by flow cytometry. As shown in FIG. 2, incubation of human Huh7.5.1 cells (FIG. 2A) and human hepatocytes (FIG. 2B) with rat polyclonal anti-CLDN-1 antibody demonstrated that the antibody recognized CLDN-1 expressed on HCV target cells including human hepatocytes. Taken together, these data demonstrate that anti-CLDN1 polyclonal antibodies produced by genetic immunization bind to the ectodomain of human CLDN1 expressed on human hepatocytes as well as human hepatoma cells.

Characterization of Anti-CLDN-1 Polyclonal Antibodies by immunofluorescence. The results obtained by immunofluorescence are presented on FIG. 3. They demonstrate that, as expected, bound anti-CLDN1 polyclonal antibodies are localized at the cell surface.

Inhibition of HCV Infection by Anti-CLDN-1 Polyclonal Antibodies. To assess the role of CLDN-1 for HCV infection, JFH1 HCVcc infection of Huh7.5.1 cells was studied in the presence of anti-CLDN-1 antibodies directed against epitopes of the CLDN-1 extracellular loops. FIG. 4A shows that anti-CLDN-1 rat serum inhibited JC1 HCVcc infection by more than 80% at a concentration of 100 µg/mL. In contrast, the control pre-immune serum had no effect on HCVcc infection (FIG. 4A). Taken together, these data demonstrate that antibodies directed against the CLDN1 ectodomain efficiently inhibit HCV infection.

To confirm that inhibition of JFH1 HCVcc infection was indeed mediated by anti-CLDN-1 antibodies, IgG was purified from rat anti-CLDN-1 serum and from control serum. As shown in FIG. 4B, anti-claudin-1 purified IgG markedly inhibited HCVcc infection of Huh7.5.1 cells in a similar manner to anti-CLDN-1 serum. In contrast, control IgG (100 µg/mL) purified from pre-immune serum did not inhibit HCVcc infection (FIG. 4B). These data clearly demonstrate that the inhibitory effect of anti-CLDN-1 serum is mediated by anti-CLDN1 antibody and not by other substances present in the serum (such as CLDN-1 ligands potentially interfering with CLDN-1 function).

Furthermore, the inhibitory effect of purified anti-claudin-1 antibodies on HCV infection was confirmed using retroviral HCV pseudotyped particles (HCVpp). Anti-claudin-1 antibodies, but not control antibodies, inhibited infection of Huh7 cells by HCVpp in a dose-dependent manner (data not shown).

In conclusion, these results demonstrate that anti-claudin-1 polyclonal antibodies efficiently inhibit HCV infection.

Figure 6:
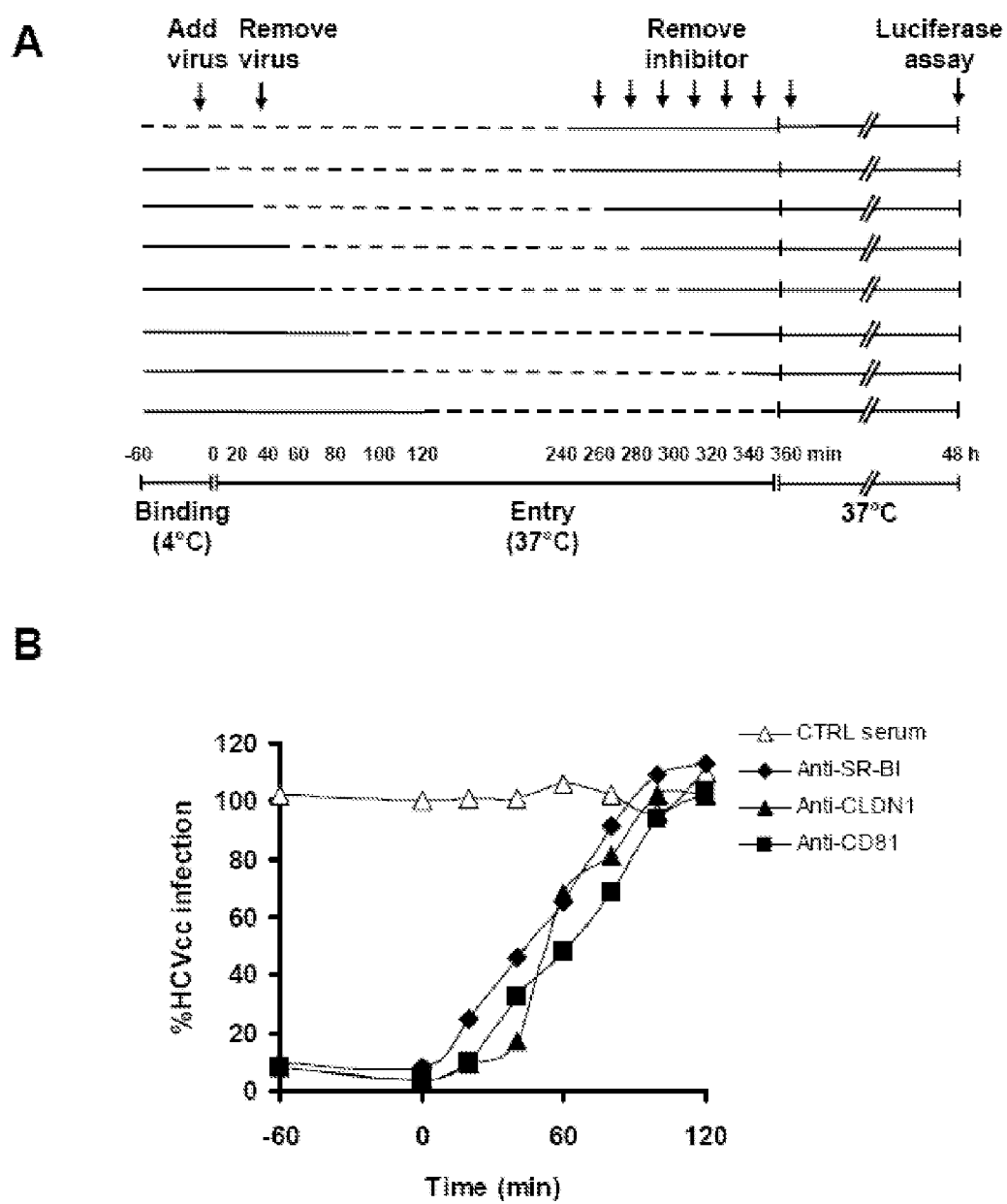
FIG. 6(B) shows the kinetics of inhibition of HCVcc entry into human hepatoma cells by anti-CD81 mAb (■), rat anti-SR-BI serum (♦), rat anti-CLDN1 serum (▲) or control rat serum (Δ). Inhibition of Luc-Jc1 HCVcc entry into Huh7.5.1 cells by rat anti-CLDN1 serum (1/100), rat anti-SR-BI serum (1/100), rat control serum (1/100) or anti-CD81 monoclonal antibody (5 μg/mL) was performed as shown in the schematic drawing of the experimental setup presented in FIG. 6(A). After virus binding to target cells, cells were washed, and inhibitors were added every 20 minutes for 120 minutes at 37° C. to allow entry to proceed. Dashed lines indicate the time intervals where inhibitors were present. Luciferase activity was determined 48 hours later and is expressed relative to control infections performed in the same way but without addition of inhibitors. Results in (B) are expressed as percent Luc-Jc1 HCVcc infectivity in the absence of antibody. Means±SD of one out of three experiments performed in duplicate are shown.

Using an anti-CD81 monoclonal antibody, rat-anti-SR-BI serum, and rat anti-CLDN1 serum obtained as described above, the Applicants have shown that blocking of CLDN1 and CD81, or CLDN1 and SR-BI, or CLDN1, CD81 and SR-BI inhibited HCVcc infection more potently than blocking of each entry factor alone (see FIG. 5(A)-(E)). Taken together, these data suggest that CLDN1 mediates HCV entry in cooperation with CD81 and SR-BI. The anti-CD81 monoclonal antibody, rat-anti-SR-BI serum, and rat anti-CLDN1 serum were also found to inhibit HCVcc infection of Huh7.5.1 cells with similar kinetics, suggesting that CLDN1, SR-BI and CD81act almost simultaneously during the HCV entry process in Huh7.5.1 cells (see FIG. 6).

Example 2

Anti-Claudin-1 Monoclonal Antibodies

Materials and Methods

Cell Lines and Primary Hepatocytes. Culture of human Huh7 (Steinmann, 2004), Huh7.5.1 (Zhong, 2005), 293T (Pestka, 2007), BOSC23 (Pear, 1993), hamster CHO (Barth, 2005) and murine Hepa1.6 cells (Steinmann, 2004) have been described previously. Primary human and mouse hepatocytes were isolated and cultured as described (Codran, 2006; Lan, 2008; Zeisel, 2007). Primary cynomolgus hepatocytes were purchased from PRIMACYT Cell Culture Technology GmbH, Germany.

Binding of anti-CLDN1 Mabs to Primary Human Hepatocytes and Cross-Competition Analysis. Huh7.5.1 cells or primary human or cynomolgus hepatocytes ($2 \times 10^5$ cells/well) were incubated for 30 minutes at room temperature with increasing concentrations of anti-CLDN1 mAbs in phosphate-buffered saline (PBS)-3% fetal calf serum (FCS). MAb binding was revealed by incubation with PE-conjugated anti-rat IgG mAb (Southern Biotechnology Associates). As a control, isotype-matched rat IgG2b (Genovac) was used. FACS acquisitions and analysis were performed with a FACScan (Beckton Dickinson) and CellQuest software. Competition between anti-CLDN1 MAbs was measured by a cell-based ELISA. Huh7.5.1 human hepatoma cells ($2 \times 10^5$ cells/well) were seeded in 96-well plates. After blocking the wells, the cells were incubated for 60 minutes with 0.1 µg/mL biotinylated anti-CLDN1 MAb together with increasing concentrations of unlabeled anti-CLDN1 MAbs as competitors. Following washing of cells in PBS binding of biotinylated antibody was detected by incubation with streptavidin labelled with horseradish peroxidise (BD). Binding was measured as relative fluorescence units (590 nm) after washing and development with Amplex Red reagent. Curves determined by measurement of binding in the presence of an isotype-matched control were compared to those determined in the presence of the competing antibody. Biotin labelling was performed using Sulfo-NHS-LC-Biotin (Thermo Scientific) according to the manufacturer's recommendations.

Imaging Studies of Cell Surface CLDN1. Living Huh7.5.1 cells were incubated with rat isotype control or rat anti-CLDN1 OM-7D3-B3 (10 µg/mL) and a Cy5-conjugated anti-rat secondary antibody (1/300; Jackson Immunoresearch) in the absence of permeabilization reagents. Following staining, the cells were fixed, mounted and observed using a Leica LSR2CLSM (IGBMC Imaging Center, Illkirch, France).

Mapping of Epitopes Targeted by anti-CLDN1 MAbs. Epitope mapping was performed using pQCXIN-hClaudin1 plasmids encoding for wild-type CLDN1 or CLDN1 containing defined mutations introduced by site-directed mutagenesis (Cukierman, 2009). These CLDN1-mutant plasmids were kindly provided by Dr. Tanya Dragic (Department of Microbiology and Immunology, Albert Einstein College of Medicine, Bronx, N.Y.). Wild-type and mutant CLDN1 contain a cytoplasmic N-terminal hemagglutinin (HA)-Tag, allowing quantification of transfection efficiency and protein expression (Cukierman, 2009). To study binding of anti-CLDN1 MAbs to mutant CLDN1, CLDN1-negative BOSC23 cells were transiently transfected with CLDN1 expression constructs (0.05 µg DNA; Lipofectamine). 48 hours later, binding of monoclonal antibody OM-7D3-B3 or OM-8A9-A3 to BOSC23-cells transiently transfected with pQCXIN-hClaudin1 plasmids was determined by flow cytometry. Flow cytometry quantitation of HA-tag expression using an anti-HA antibody served as internal control. The transfected cells were either permeabilized with Cytoperm/Cytofix (BD) for analysis of cytoplasmic HA-Tag expression or untreated for analysis of anti-CLDN1-mutant CLDN1 interactions. For FACS analysis, transfected cells were incubated with anti-CLDN1 mAb or anti-HA (Covance) for 30 minutes followed by incubation with 10 µg/mL anti-rat IgG mAb (for anti-CLDN1) or 10 µg/mL anti-mouse IgG mAb labelled with phycoerythrin (for anti-HA).

HCVcc Production and Infection. HCVcc (strains Jc1, Luc-Jc1, Luc-Con1) were generated as described previously (Haberstroh, 2008; Koutsoudakis, 2006; Pietschmann, 2006; Wakita, 2005; and Zeisel, 2007). For infection experiments, Huh7.5.1 cells were seeded in 48-well tissue culture plates at a density of $2 \times 10^4$ cells/well. Cells were pre-incubated in the presence or absence of antibodies for 1 hour at 37° C. and then infected at 37° C. for 4 hours with Jc1 HCVcc or Luc-Jc1 HCVcc. 48 hours later, HCV infection was analyzed in cell lysates by quantification of intracellular HCV RNA using RT-PCR or luciferase activity as described previously (Haberstroh, 2008; Koutsoudakis, 2006; Tscherne, 2006; and Zeisel, 2007).

HCV Pseudoparticle (HCVpp) Production and Infection. MLV- or HIV-based HCVpp (strains H77, HCV-J, JFH-1, UKN3A.1.28, UKN4A.21.16, UKN5.14.4, UKN6.5.340, VI, VJ, VD, VH, VK and VA-VY) and VSVpp were produced as described (Lavilette, 2005; Bartosch, 2003; Pietschmann, 2006; Zeisel, 2007; Fafi-Kremer, 2009). For infection experiments, HEK293T, 293T/CLDN1+ and Huh7.5 cells were plated in 24-well plates the day prior to kinetic experiments as described previously (Haberstroh, 2008). 72 hours later, the cells were lysed and HCVpp entry was analyzed by quantitation of luciferase reporter gene expression as described (Koutsoudakis, 2006).

Toxicity Assays. Cytotoxic effects on cells were assessed in triplicate by analyzing the ability to metabolize 3-(4,5-dimethylthiazoyl-2-yl)-2,5-diphenyl-tetrazolium bromide (MTT) (Mosmann, 1983). Huh7.5.1 cells and primary human hepatocytes from three different donors were incubated with rat monoclonal antibody, anti-CLDN1 OM-7D3-B3 (0.01-100 µg/mL), flavopiridol (10 µM, Sigma) or compound C (0.01-100 µM, Sigma). The final concentration of MTT was 0.6 mg/mL. Formazan crystals produced by the cells were solubilised and measured as described (Mosmann, 1983).

Statistical Analysis. Results were expressed as the mean±standard deviation (SD). Statistical analyses were performed using Student's t test with a P value of <0.05 being considered statistically significant.

Results

Production of Monoclonal Antibodies Specific for the Extracellular Domains of Cell Surface CLDN1. Five rats were immunized with a full-length human Claudin-1 cDNA (NCBI Accession Number: NM_021101) in a mammalian expression vector applying standard genetic immunization protocols used by Genovac GmbH as summarized elsewhere (Lohrmann, 2003, which is incorporated herein by reference in its entirety), with screening based on a Genovac system described in German Patent No. DE 198 52 800 (which is incorporated herein by reference in its entirety). Briefly, for this screening, sera and hybridoma supernatants are tested against mammalian cells transfected with tagged cDNA constructs expressing the targets against which antibodies are being generated. The DNA vectors are so designed that the resulting protein is secreted and temporarily attached to the plasma membrane. This allows a cell-based screening assay using flow cytometry or a cell-based ELISA.

Figure 7:
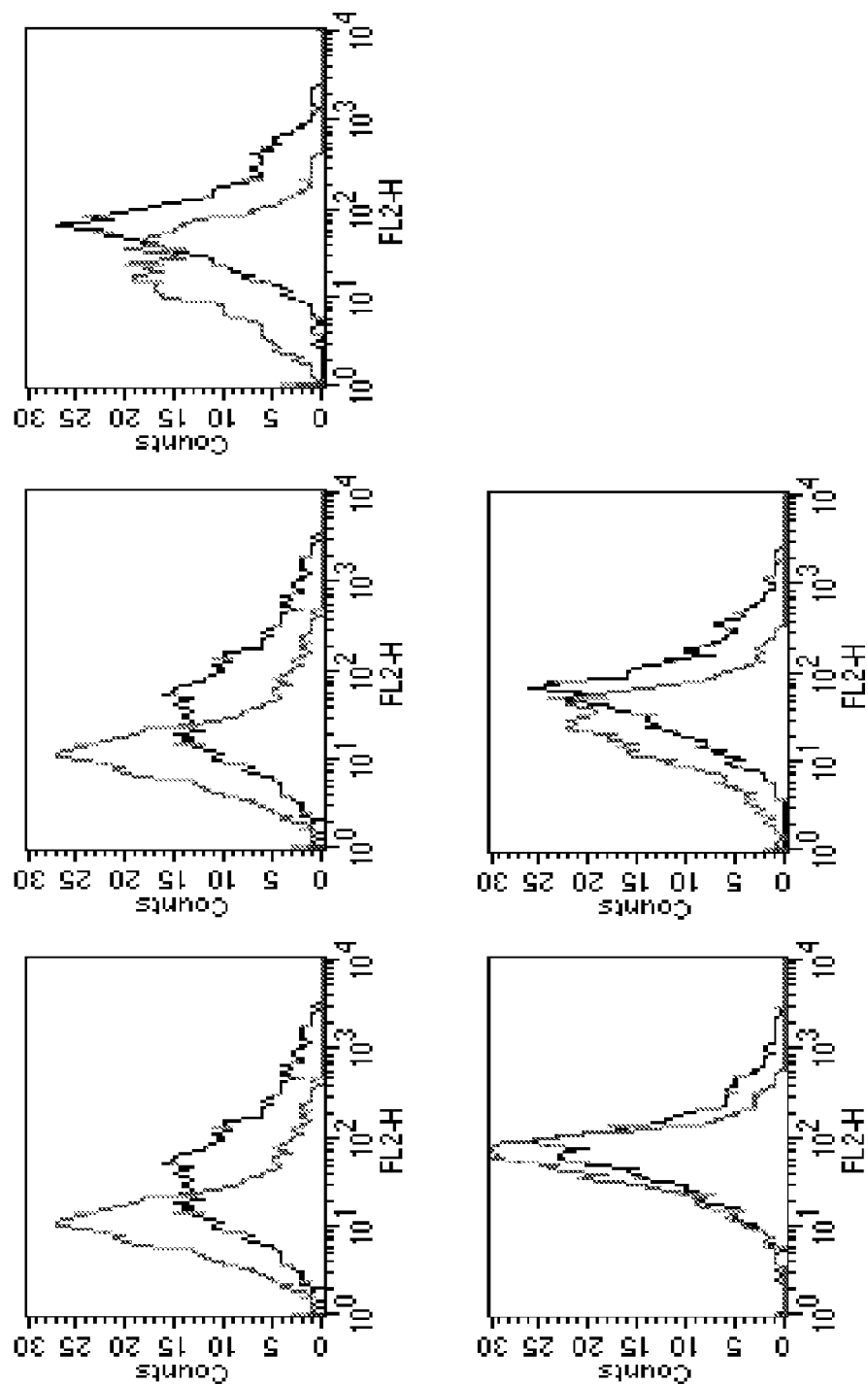
FIG. 7 is a set of five graphs showing the results of flow cytometry analysis for sera obtained from 5 rats immunized against human Claudin-1 (as described in Example 2). The black curves show results on mammalian cells (BOSC23) transiently transfected with a human Claudin-1 expression vector and the red curves with an irrelevant cDNA. A shift of the black curve to the right indicates positivity. Antibodies were detected with a PE-labeled anti-rat IgG antibody (FL2).

Following several DNA boosts, the animals were sacrificed, and sera and lymphocytes were collected from the individual animals. Sera from each animal were tested by flow cytometry for recognition of the human Claudin-1 protein, following transient transfection of the Claudin-1 cDNA into mammalian cells (FIG. 7).

The lymphocytes from rat 3 were removed and fused with SP2/0/Ag14 mouse myeloma cells (ATCC Number: CRL-1581) using standard PEG conditions and the resulting hybridomas were plated onto 96-well plates under standard selection conditions (see, for example, E. Harlow and D. Lane, in "Antibodies, A Laboratory Manual", Chapter 6, 1988, Cold Spring Harbor). After two weeks, the hybridoma supernatants were tested in a cell-based ELISA against mammalian cells that had been transiently transfected with the Claudin-1 cDNA and cells transfected with an irrelevant cDNA as a negative expression control. This pre-selection allowed the identification of positive hybridomas that were transferred for expansion onto 24-well plates followed by 6-well plates and their supernatants were re-tested by flow cytometry against mammalian cells that had been transiently transfected with the same positive and negative cDNA constructs as used for the cell-based ELISA.

Figure 8:
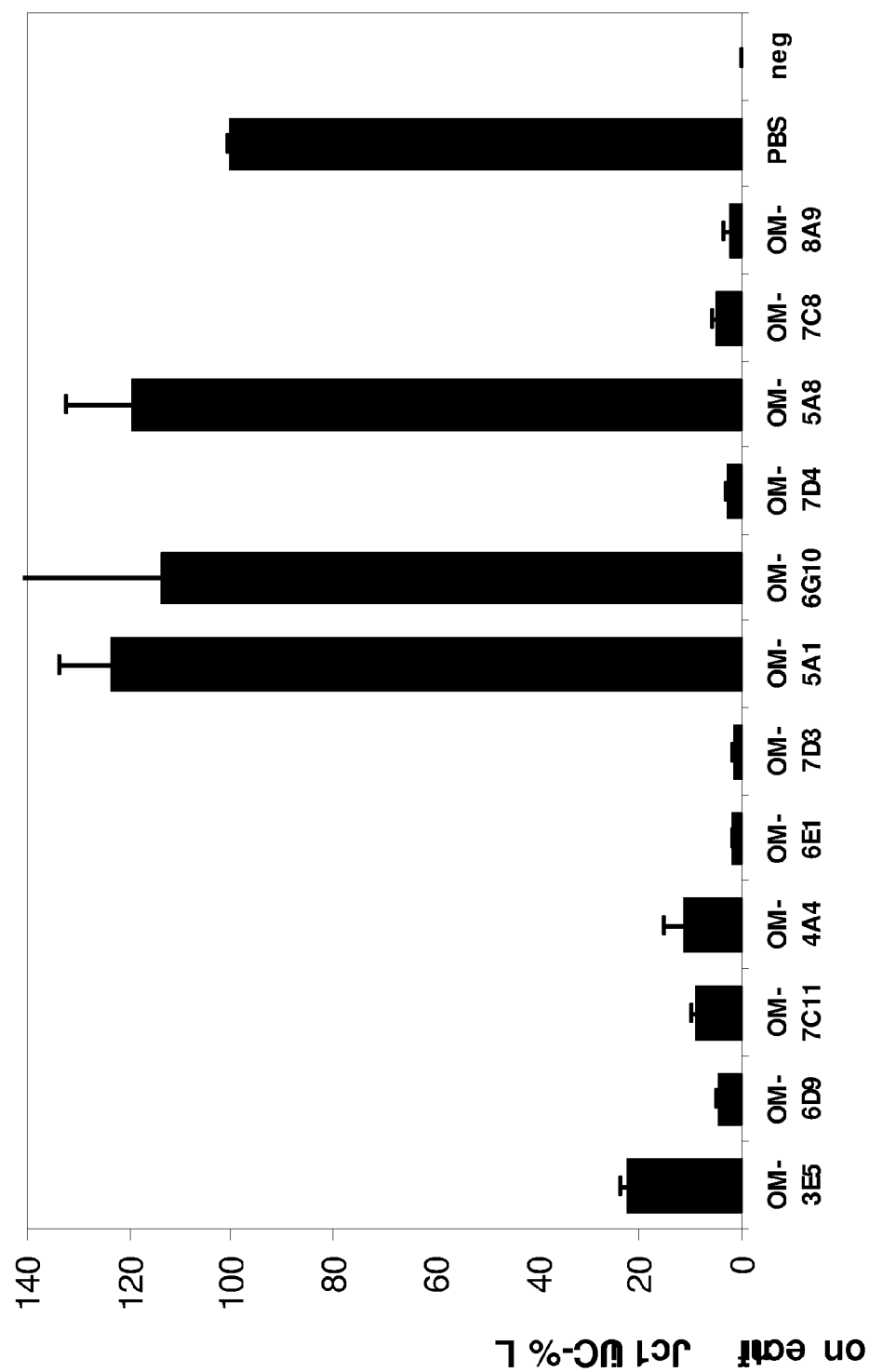
FIG. 8 is a graph showing results of the analysis of inhibition of infection with recombinant infectious HCV (HCVcc Luc-Jc1) with hybridoma supernatants containing anti-CLDN-1 antibodies (the names of which are indicated on the x-axis). The hybridoma supernatants were obtained as described in Example 2. The results are expressed as percentage HCVcc Luc-Jc1 infection in the presence or absence of hybridoma supernatant (with infection in the presence of PBS=100%). OM-3E5, OM-6D9, OM-7C11, OM-4A4, OM-6E1, OM-7D3, OM-7D4, OM-7C8 and OM-8A9 showed a marked inhibition of HCV infection, while OM-5A1, OM-6G10, and OM-5A8 showed no effect. Negative control corresponds to non-infected cells.

An analysis of the inhibition of infection with recombinant infectious HCV (HCVcc Luc-Jc1) by hybridoma supernatants containing anti-CLDN-1 antibodies was then performed. More specifically, Huh7 cells were incubated with 100 μL of hybridoma supernatant containing antibodies for 1 hour at 37° C. Then, infectious HCVcc (TCID 10$^5$/mL; derived from the Luc-Jc1 strain containing a luciferase reporter element) were added for 3 hours at 37° C. The supernatant was then removed and replaced by fresh medium (DMEM, 10% FBS). Two or three days later, viral infection was quantitated by expression of luciferase reporter gene in cell lysates (Zeisel, 2007). The results obtained, expressed as percent HCVcc Luc-Jc1 infection in the presence or absence of hybridoma supernatant (infection in the presence of PBS=100%) are presented in FIG. 8. As can be seen on this Figure, OM-3E5, OM-6D9, OM-7C11, OM-4A4, OM-6E1, OM-7D3, OM-7D4, OM-7C8 and OM-8A9 showed a marked inhibition of HCV infection, whereas OM-5A1, OM-6G10, and OM-5A8 showed no effect.

Following analysis of their blocking activity, the mother clones OM-3E5, OM-6D9, OM-7C11, OM-4A4, OM-6E1, OM-7D3, OM-7D4, OM-7C8 and OM-8A9 were subcloned by plating them into a semi-solid medium, picking the resulting subclone colonies and transferring them into 96-well plates (OM7C11 revealed blocking activity but as this was an inefficient producer of antibodies it was not subcloned). The resulting subclones were picked and re-tested for their ability to bind to human CLDN1 expressed on the cell surface of transfected, non-permeabilized human BOSC23 as well as transfected hamster CHO cells. Human BOSC23 cells are HEK293-derived ecotropic packaging cells (Pear, 1993) which do not express endogenous CLDN1 (data not shown). The results of these analyses are presented in FIG. 9. The following subclones were selected: OM-3E5-B6, OM-6D9-A6, OM-4A4-D4, OM-6E1-B5, OM-7D3-B3, OM-7D4-C1, OM-7C8-A8 and OM-8A9-A3.

Figure 9A:
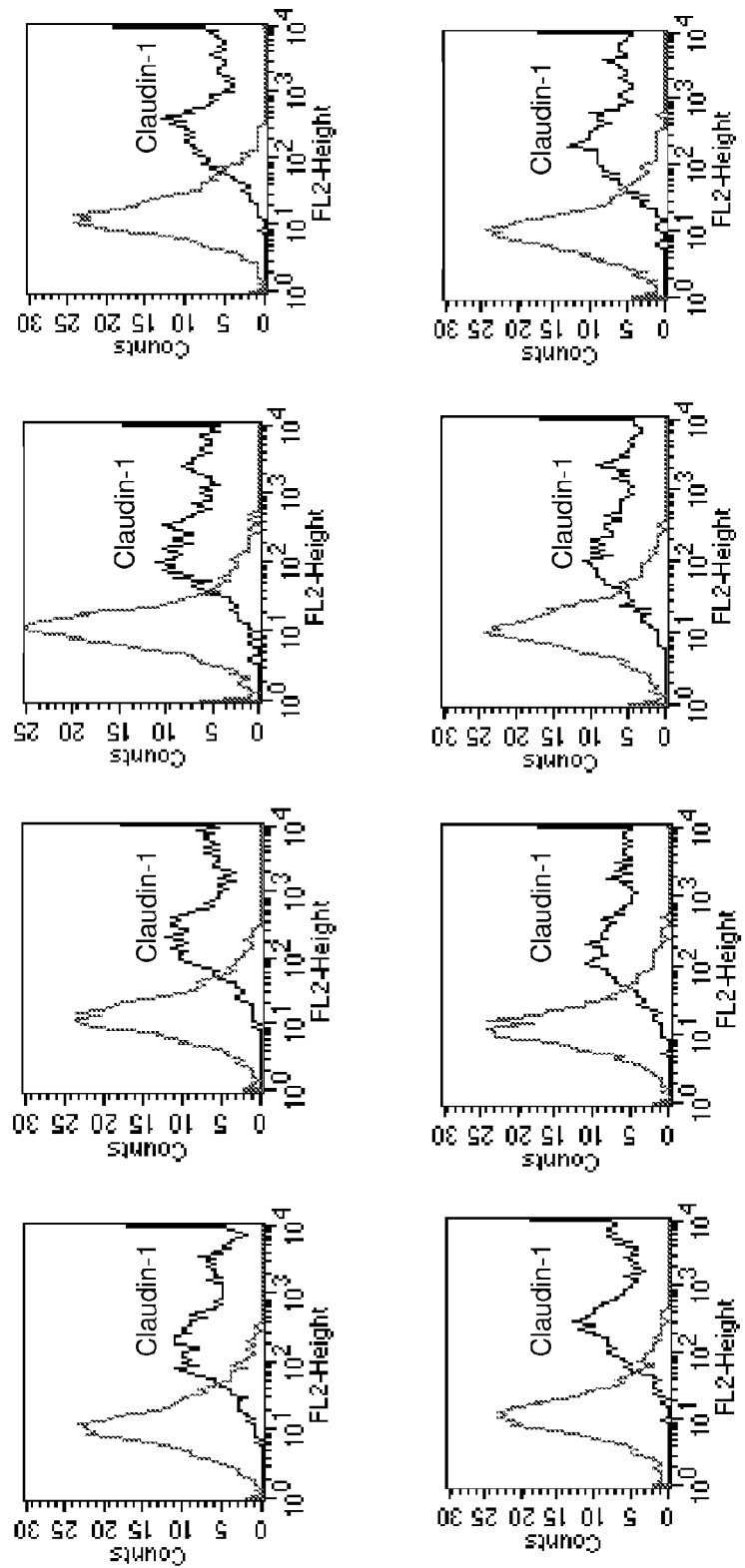
FIG. 9(A) is a set of eight graphs showing the results of flow cytometry analysis for monoclonal antibody supernatants obtained from pooled lymphocytes from rats immunized against human Claudin-1 (as described in Example 2). The black curves show results on mammalian cells transiently transfected with a human Claudin-1 expression vector (pCMV-SPORT6-CLDN1) and the red curves with an irrelevant cDNA (pCMV-SPORT6). A shift of the black curve to the right indicates positivity. Antibodies were detected with a PE-labeled anti-rat IgG antibody (FL2). The x and y axes show mean fluorescence intensities and relative numbers of stained cells, respectively.

Incubation of BOSC23 and CHO cells expressing human CLDN1 with rat monoclonal anti-human CLDN1 antibodies resulted in a specific interaction with human CLDN1 (FIG. 9A and FIG. 9B).

To study whether anti-human CLDN1 antibodies bind to the extracellular loops of CLDN1 on the cell surface of the HCV permissive Huh7.5.1 cells and primary human hepatocytes, cells were incubated with anti-CLDN1 antibodies and analyzed by flow cytometry in the absence of permeabilization reagents. Positive staining of native human Huh7.5.1 hepatoma cells and human hepatocytes with monoclonal anti-CLDN1 antibodies demonstrated that these antibodies bind to CLDN1 expressed on the cell surface of primary hepatocytes and HCV permissive cell lines (FIG. 9C). In contrast, no staining was observed for human CLDN1-deficient BOSC23 cells (FIG. 9A) incubated with anti-CLDN mAbs or Huh7.5.1, CHO/CLDN+ cells or primary human hepatocytes incubated with isotype control antibodies (FIG. 9B). Staining of native cell surface CLDN1 by monoclonal antibodies was also confirmed by immunofluorescence on living, non-permeabilized Huh7.5.1 cells (FIG. 9D). Taken together, these data demonstrate that monoclonal anti-CLDN1 antibodies produced by genetic immunization specifically bind to the extracellular loops of native CLDN1 expressed on the cell surface of HCV permissive cell lines and human hepatocytes.

Figure 19:
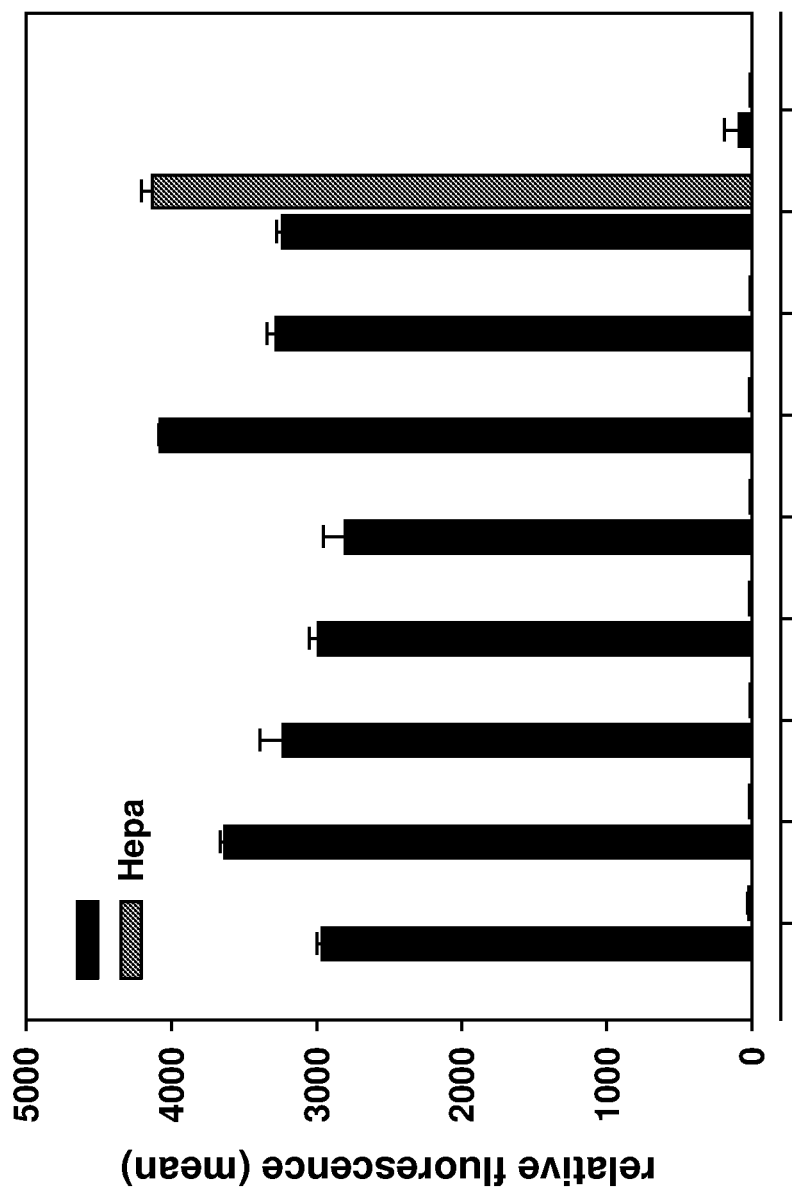
FIG. 19 is a graph showing the binding of the six monoclonal antibodies to cell surface expression of CLDN1 on human Huh7.5.1 hepatoma cells and mouse Hepa 1.6 hepatoma cells studied by flow cytometry. Results are shown as the mean relative fluorescent and each experiment was performed in duplicate. An anti-CD81 monoclonal antibody was used as positive control.

To investigate whether anti-human CLDN1 antibodies cross-react with murine CLDN1, the binding of mAbs to murine CLDN1 expressed on murine liver-derived cell lines was studied. Interestingly, monoclonal anti-CLDN1 antibodies did not interact with murine CLDN1 expressed on the mouse hepatoma cell line Hepa1.6. Furthermore, as shown in FIG. 9 anti-CLDN1 antibodies did not stain hamster cell line CHO. These findings suggest no cross-reactivity of anti-human CLDN1 antibodies with the extracellular loops of murine or hamster CLDN1 (FIG. 9 and FIG. 19). In contrast, rat monoclonal anti-CLDN1 showed cross-reactivity with primary hepatocytes of the non-human primate cynomolgus monkey (Macaca fascicularis) (FIG. 9E). These data suggest that the epitope(s) targeted by the antibodies is conserved among primates but different in rodents such as mouse or hamster.

Each sub-clone was frozen down and a portion expanded in serum-free ISF-1 medium (Biochrom AG, Catalogue Number: 9061-01). The antibodies were purified on a protein G column and their concentrations were determined in PBS buffer. Isotypes were determined for each clone using a commercial ELISA test from BD-Pharmingen (Catalogue Number: 557081). The nature of the light chains was also determined using the same commercial ELISA kit. The results of these analyses are shown in Table 1 below.

TABLE 1

Characteristics of the monoclonal antibodies secreted by the selected hybridoma cell lines

| Hybridoma Cell Line | Secreted Monoclonal Antibody | |
|---|---|---|
| | Isotype | Light Chain |
| OM-6E1-B5 | rIgG2b | kappa |
| OM-8A9-A3 | rIgG2b | kappa |
| OM-6D9-A6 | rIgG2b | kappa |
| OM-7D4-C1 | rIgG2b | kappa |
| OM-3E5-B6 | rIgG2a | kappa |
| OM-7C8-A8 | rIgG2b | kappa |
| OM-4A4-D4 | rIgG2a | kappa |
| OM-7D3-B3 | rIgG2b | kappa |

Figure 10A:
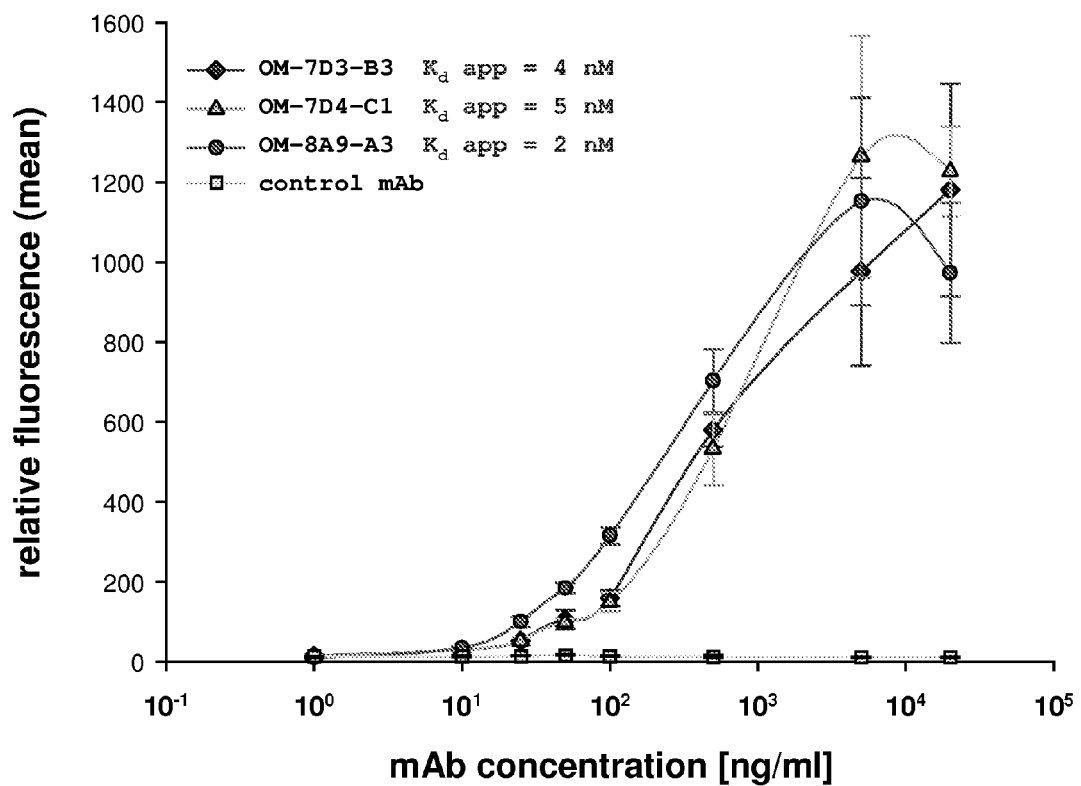
FIG. 10 is a set of two graphs showing the binding properties of anti-CLDN1 mAbs to HCV permissive cell lines Huh7.5.1. Huh7.5.1 cells were incubated with increasing concentrations of anti-CLDN1 MAbs as described in Example 2. MAb binding was revealed by flow cytometry using PE-conjugated anti-rat IgG mAb. As a control, an isotype-matched human IgG2 was used.
Figure 10B:
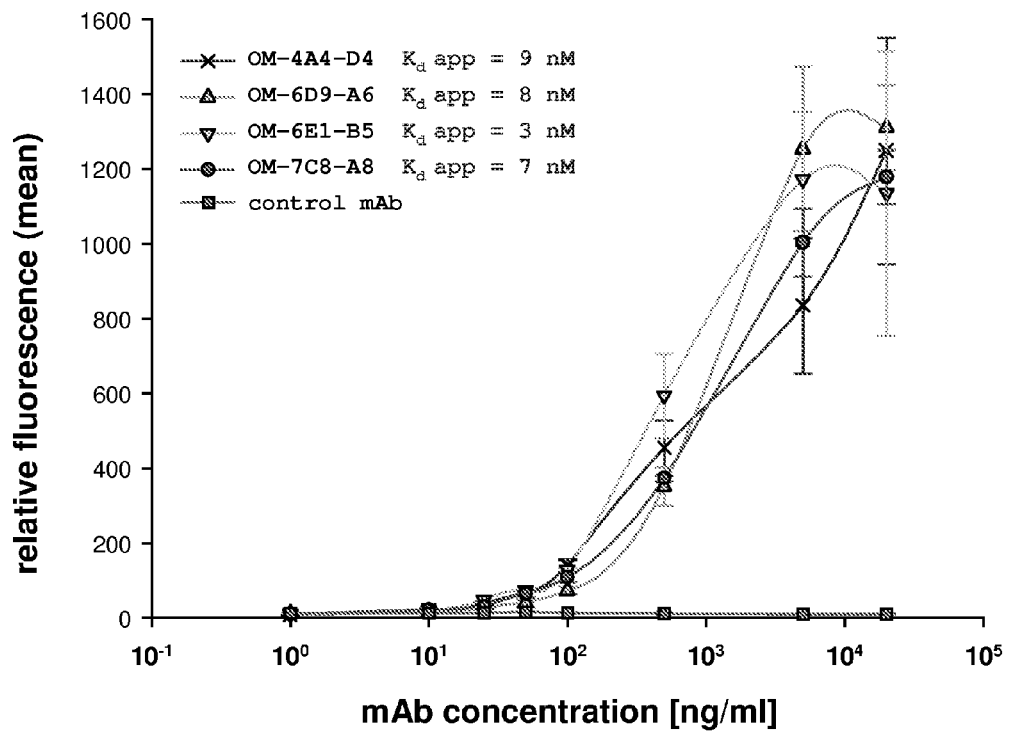

Characterization of Binding Properties of anti-CLDN1 mAbs to HCV-permissive Cells and Primary Human Hepatocytes. The binding properties of anti-CDLN1 mAbs to HCV permissive cells and primary human hepatocytes were characterized by flow cytometry. As shown in FIG. 10, the measured half-saturating concentrations for binding to Huh7.5.1 cells—which corresponds to the apparent $K_D$ of the antibodies, were as follows: 7D3-B3 4 nM; 7D4-C1 5 nM; 8A9-A3 2 nM; 4A4-D4 9 nM, 6D9-A6 8 nM, 6E1-B5 3 nM, 7C8-A8 7 nM (FIG. 10A). Similar half-saturating concentrations and apparent KD of the antibodies were obtained for antibody binding to primary human hepatocytes (data not shown). These results demonstrate that anti-CDLN1 antibodies bind to HCV permissive cell lines and human hepatocytes with high affinity.

Figure 11:
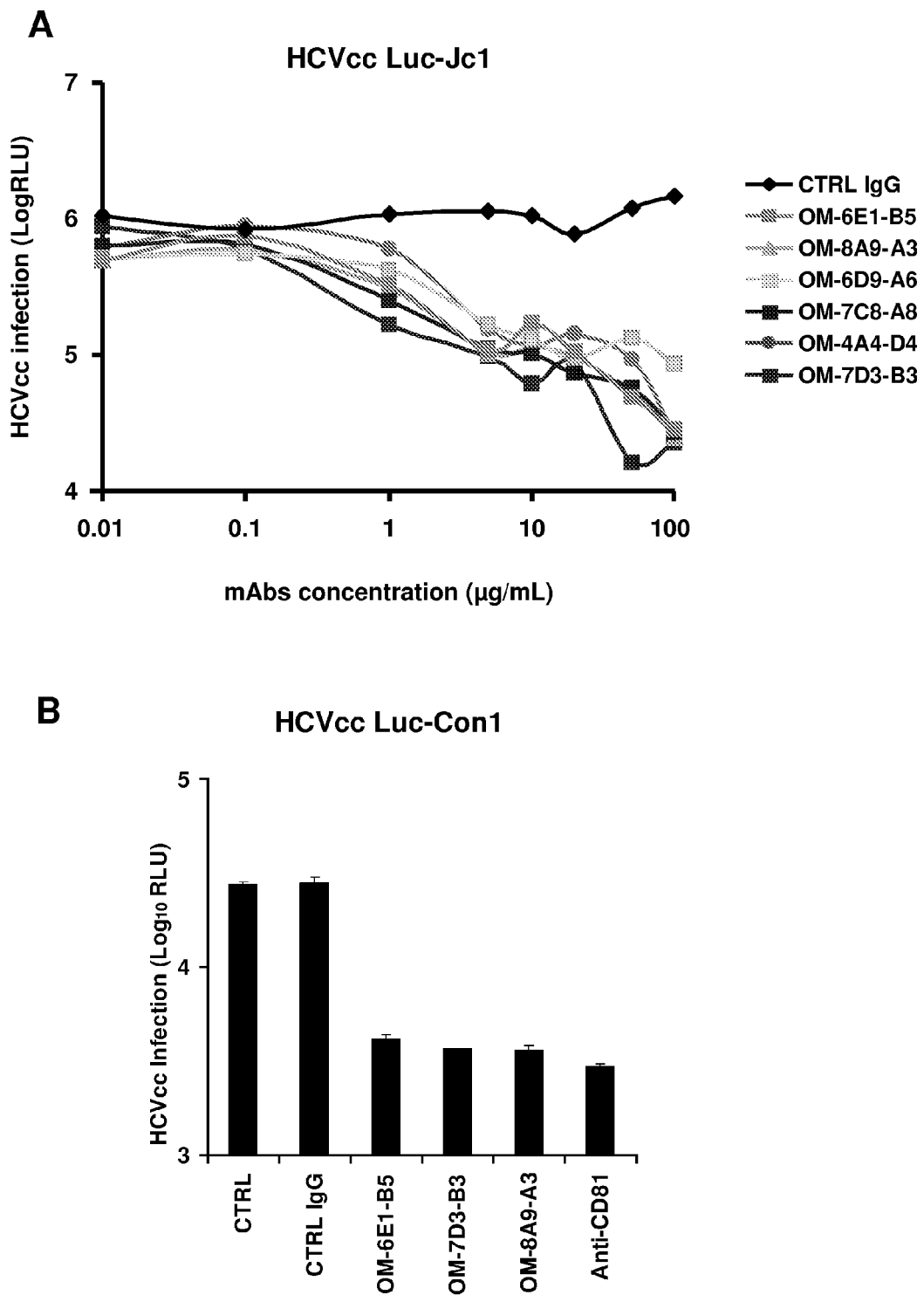
FIG. 11 is a graph showing the dose-dependent inhibition of HCVcc infection by anti-CLDN1 antibodies using infectious virions containing the structural proteins of the HCV genotype 2a J6 strain (Luc-Jc1) and the genotype 1b Con1 strain (Luc-Con1). (A) Huh7.5.1 cells were pre-incubated with increasing concentrations of rat anti-CLDN1 or isotype control antibodies (CTRL IgI) for 1 hour at 37° C. before infection with Luc-Jc1 HCVcc (genotype 2a), (B) Huh7.5.1 cells were pre-incubated with rat anti-CLDN1 (10 μg/μL of antibodies OM6E1-B5; OM-7D3-B3; OM-8A9-A3), anti-CD81 (10 μg/μL) or isotype control antibodies (CTRL IgG; 10 μg/μL) or in the absence of antibody (CTRL) before incubation with HCVcc Luc-Con1 for 4 hours at 37° C. HCVcc Luc-Con1 contains the HCV structural proteins of genotype 1b strain Con1. HCV infection was assessed by measurement of luciferase activity 48 hours post-infection as described in Example 2. Mean±SD from a representative experiment performed in triplicate are shown.
Figure 12:
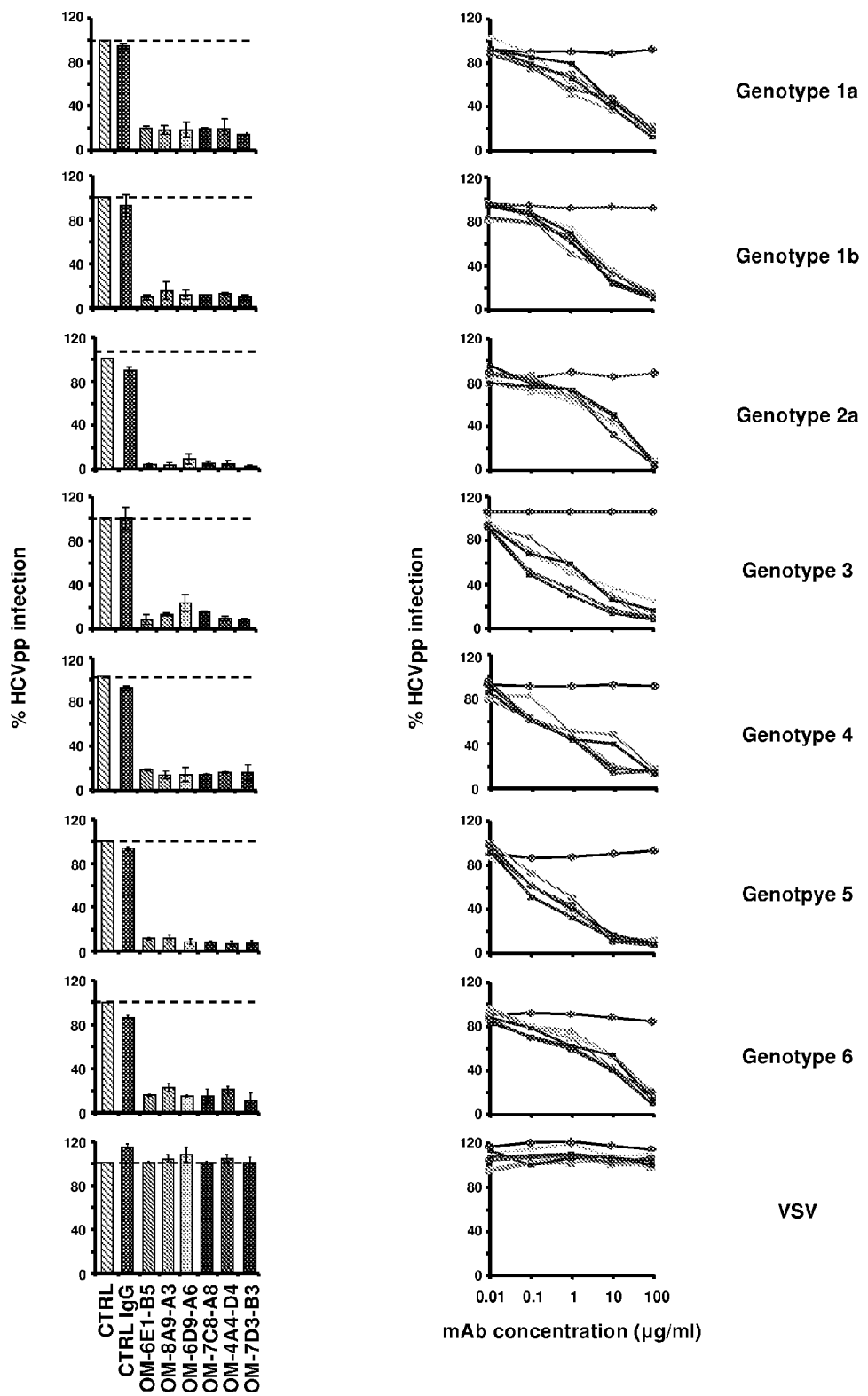
FIG. 12 is a set of graphs showing that anti-CLDN1 monoclonal antibodies cross-neutralize HCVpp bearing envelope glycoproteins derived from the major HCV genotypes. Different strains of MLV-based HCVpp bearing envelope glycoproteins of strains H77 (genotype 1a), HCV-J (genotype 1b), JFH1 (genotype 2a), UKN3a 1.28 (genotype 3), UKN4a 21.16 (genotype 4), UKN 5.14.4 (genotype 5), and UKN 6.5.340 (genotype 6). VSV pseudo-particles were used as a control. HCVpp and VSVpp were produced as described in Example 2. Huh7 cells were pre-incubated with increasing concentrations of rat anti-CLDN1 or rat isotype control antibodies for 1 hour at 37° C. before infection with HCVpp or VSVpp for 4 hours at 37° C. HCVpp and VSV infection was assessed by measurement of luciferase activity 72 hours post-infection as described in Example 2. Mean±SD from a representative experiment performed in triplicate are shown.
Figure 13:
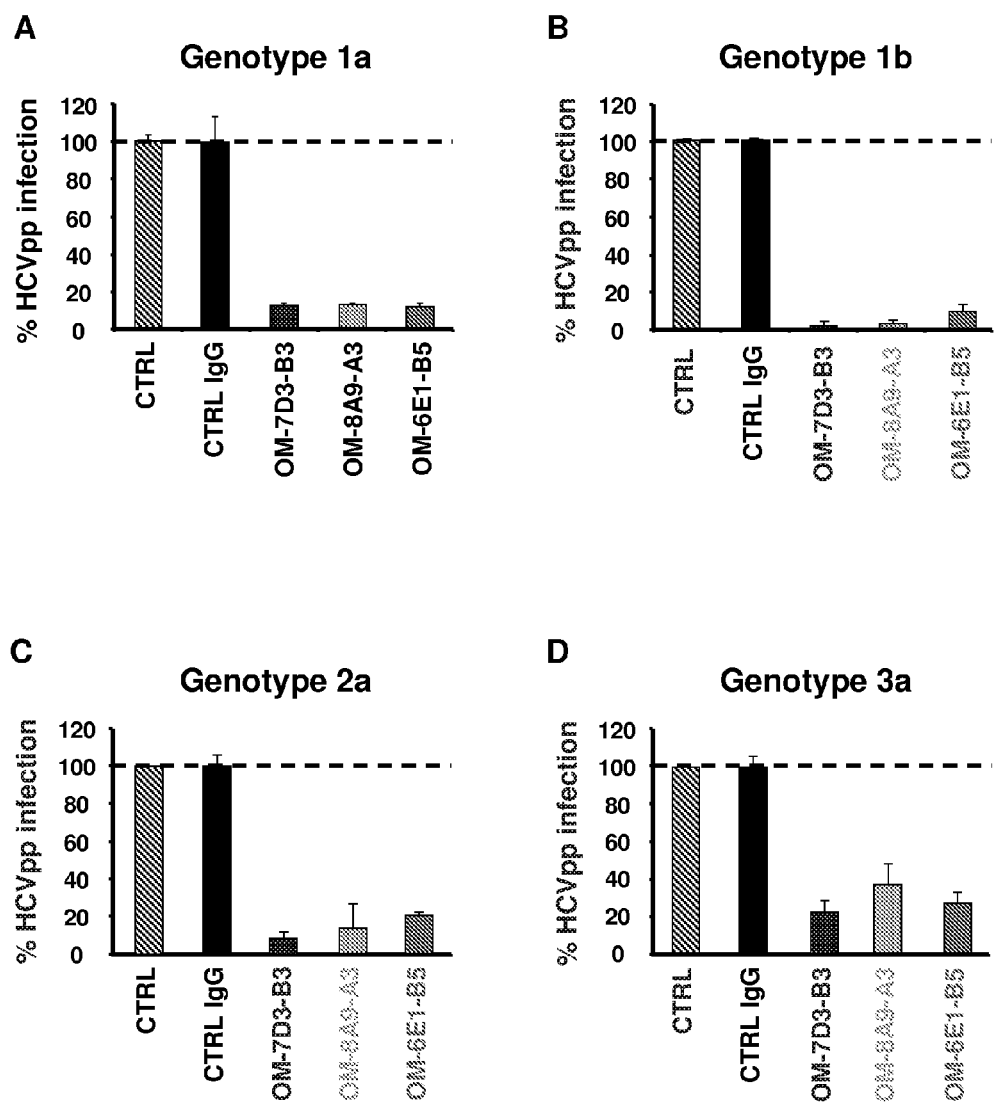
FIG. 13 is a set of graphs showing the inhibition of HCVpp infection in primary human hepatocytes. HIV-based HCVpp bearing envelope glycoproteins of strains HCV H77 (genotype 1a), HCV-J (genotype 1b), JFH-1 (genotype 2a), UKN3A.1.28 (genotype 3) were produced as described in Example 2. Primary human hepatocytes were pre-incubated with rat anti-CLDN1 or rat isotype control antibodies (10 μg/mL) for 1 hour at 37° C. before infection with HCVpp for 4 hours at 37° C. HCVpp infection was assessed by measurement of luciferase activity 72 hours post-infection as described in Example 2. Mean±SD from representative experiments performed in triplicate are shown.

Cross-neutralization of HCV Isolates of all Major Genotypes and Individual Quasispecies by anti-CLDN1 antibodies. To investigate whether the antibodies produced by genetic immunization were able to inhibit HCV infection, Huh7.5.1 cells were infected with chimeric J6/CF-JFH1 firefly luciferase reporter virus Luc-J1 (Koutsoudakis, 2006) in the presence of anti-CLDN1 or isotype control antibodies. FIG. 11 shows that monoclonal anti-CLDN1 antibodies inhibited HCV infection of Huh7.5.1 cells by Luc-Jc1 and Luc-Con1 virus in a dose-dependent manner whereas isotype control antibodies had no inhibitory effect. Taken together, these data demonstrate that antibodies directed against the CLDN1 extracellular loops inhibit HCV infection. To address whether anti-CLDN1 antibodies were able to cross-neutralize HCV infection from all major genotypes, the impact of antibodies on entry of HCV pseudotyped particles (HCVpp) bearing HCV envelope glycoproteins from HCV genotypes 1-6 was analyzed. As shown in FIG. 12, monoclonal anti-CLDN1 antibodies efficiently and dose-dependently inhibited infection of Huh7.5.1 cells with HCVpp from genotypes 1-6 with an $IC_{50}$ for inhibition of HCV infection ranging from 0.1 to 5 µg/mL. Similar results were found on infection of primary human hepatocytes (FIG. 13).

A major challenge for the development of antivirals and immunosuppressive strategies is the high variability of the virus. HCV has a very high replication rate and the highly error prone viral polymerase allow for rapid production of minor viral variants called "quasispecies" that may outspace humoral and cellular immune responses (Aurora, 2009; Farci, 2006; Ray, 2005; Uebelhoer, 2008). These variants are under constant immune pressure in the infected host, and selection processes lead to domination of the viral quasispecies by the most fit virus that can evade immune recognition or confer resistance to antiviral therapies.

Figure 14A:
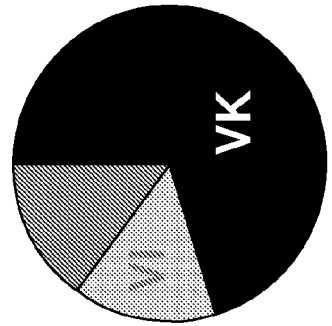
FIG. 14(A) shows the relative distribution of the three variants termed VJ, VI, VK (subtype 1b) in the first HCV-infected patient based on alignment of HVR1 sequences. Deduced amino acid of selected domains of envelope glycoproteins are shown on the right. Amino acid changes are indicated in red bold letters.
Figure 14D:
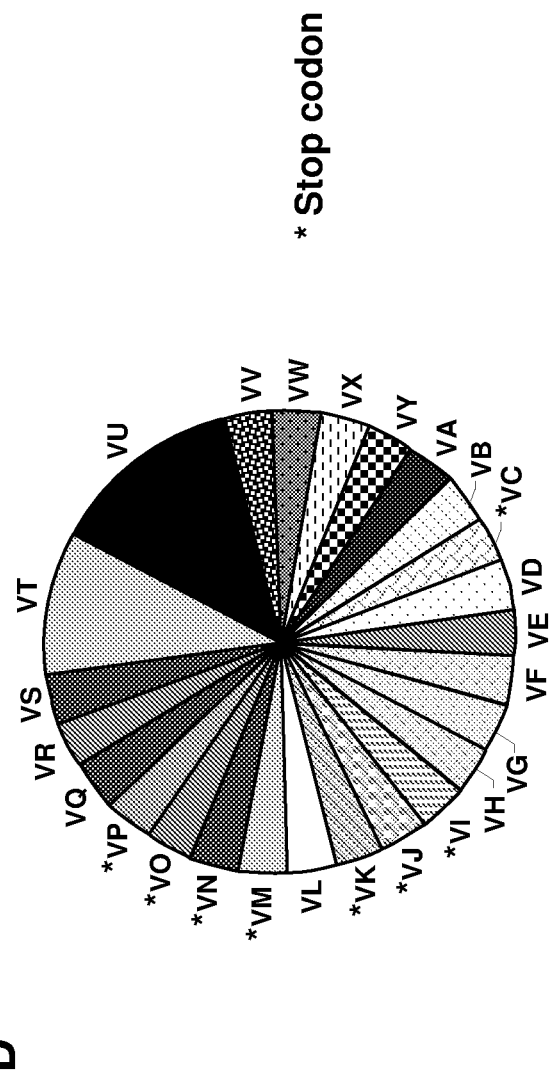
FIG. 14(D) shows the relative distribution of the variants (termed VA-VY; subtype 1b) in a second patient with chronic HCV infection based on alignment of complete E1E2 sequences.

To address whether anti-CLDN1 antibodies efficiently inhibited the population of quasispecies in individual patients, the envelope glycoproteins of two individual patients chronically infected with HCV was cloned, sequenced and expressed. As shown in FIG. 14, anti-CLDN1 antibodies broadly neutralized HCV infection of HCVpp bearing envelope glycoproteins from quasispecies from two individual patients. These data demonstrate that anti-CLDN1 antibodies cross-neutralize HCV infection of all major genotypes as well as isolates of the quasispecies population of an individual patient.

Neutralization of HCV Quasispecies and Viral Strains having Escaped Host Neutralizing Antibodies and Re-infecting the Liver Graft. End-stage liver disease due to chronic HCV infection is a leading cause for liver transplantation. Due to viral evasion from host immune responses and the absence of preventive antiviral strategies, re-infection of the graft is universal and characterized by accelerated progression of liver disease. Using primary human hepatocytes and retroviral HCV pseudotypes bearing viral envelope glycoproteins derived from HCV-infected patients undergoing liver transplantion, the Applicants have previously demonstrated that enhanced viral entry and escape from antibody-mediated neutralization are key determinants for selection of viral variants during HCV re-infection of the liver graft (Fafi-Kremer, 2009, submitted for publication).

In the present study, HCVpp displaying envelope glycoproteins from patients undergoing liver transplantation and HCV re-infection were used to assess whether anti-CLDN1 antibodies are able to inhibit infection of primary human hepatocytes with viral isolates which had escaped host neutralizing responses and had resulted in re-infection of the liver graft. To achieve that goal, the Applicants have studied the effect of anti-CLDN1 antibodies on the entry of HCVpp bearing envelope glycoproteins from HCV strains selected during transplantation and re-infecting the liver graft (HCV strains VD, VH, VK). As shown in FIG. 15, pre-incubation of cells with anti-CLDN1 antibody markedly inhibited entry of patient-derived HCVpp in primary human hepatocytes. These data clearly demonstrate that anti-CLDN1 specifically inhibits HCV entry of patient-derived isolates re-infecting the liver graft.

Cell viability analyses based on MTT testing were performed to address potential toxic effects of anti-CLDN1 antibodies. No toxic effects were detected in a side-by-side analysis of cell viability based on MTT testing even at high doses of anti-CLDN1 (FIG. 16). In contrast, compound C—a well characterized AMPK-inhibitor with known toxicity—resulted in easily detectable toxicity (FIG. 16).

Monoclonal anti-CLDN1 antibodies Binding is Dependent on Conservation of the Highly Conserved Motif W(30)-GLW (51)-C(54)-C(64) in CLDN1 Extracellular Loops. Finally, the Applicants aimed to map the epitope(s) targeted by the monoclonal anti-CDLN1 antibodies. Cross-competition experiments were performed using the six monoclonal antibodies to investigate whether anti-CLDN1 MAbs recognize a similar or different, unrelated epitopes. Binding of labelled OM-8A9-A3 or OM-7D3-B3 to Huh7.5.1 cells was measured after pre-incubation with increasing concentrations of either a control isotype-matched IgG or the anti-CLDN1 mAbs. Co-incubation with all anti-CLDN1 mAb reduced the binding of 8A9-A3 to cell-surface-displayed anti-CLDN1 by almost 80%, while the control IgG did not impair the recognition of Huh7.5.1 cells (FIG. 17A). Similar results were obtained not only for OM-8A9-A3 or OM-7D3-B3 but for all labelled OM mAbs demonstrated using saturated concentrations of inhibiting mAbs (FIG. 17B). The results obtained in the binding assay were confirmed by performing cross-competition studies in infection experiments. As shown in FIG. 17C, combination of different anti-CLDN1 antibodies did not show a marked additive or synergistic effect on the magnitude of inhibition of HCV infection. In addition to confirming the results obtained in binding studies, these results suggest that all six anti-CDLN1 antibodies recognize a similar or closely related motif on the CLDN1 extracellular loops. Provisional sequencing data however, on two of the monoclonal antibodies indicate that they vary in sequence for both the heavy and light chains (data not shown).

Figure 18A:
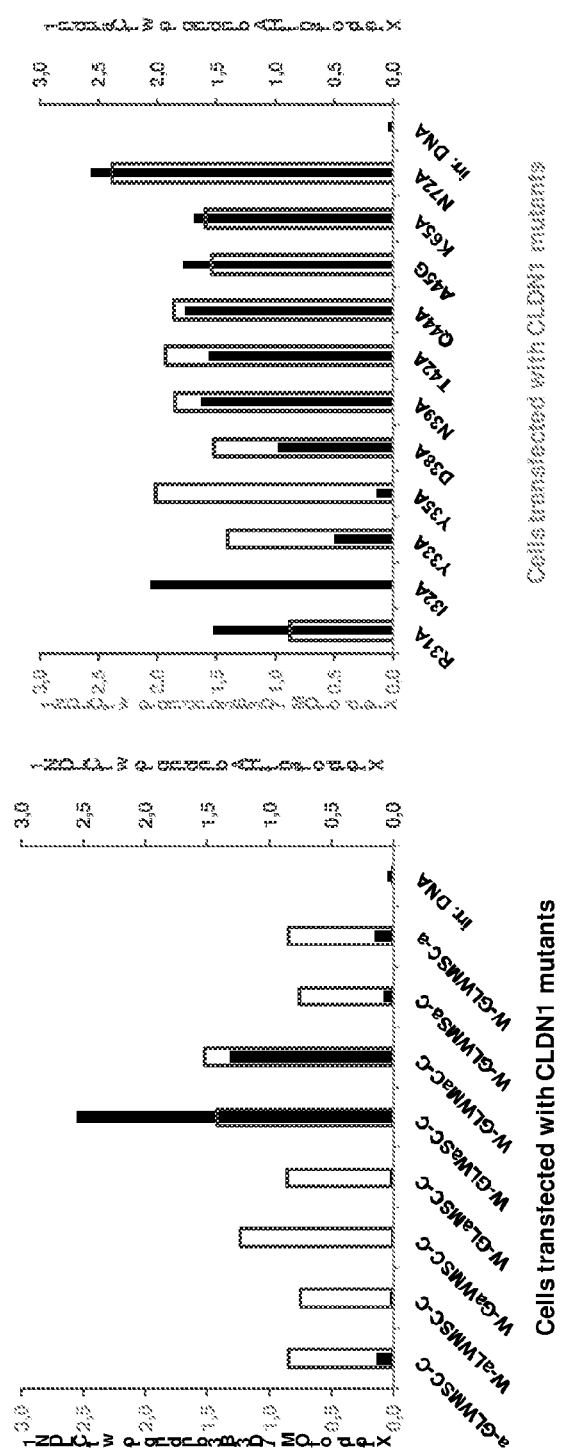
FIG. 18 is a set of graphs showing that monoclonal anti-CLDN1 antibodies bind to an epitope that is strongly dependent on conservation of the highly conserved claudin motif: W(30)-GLW(51)-C(54)-C(64). Antibody binding was performed as described in Example 2 using pQCXIN-hClaudin1 plasmids encoding for wild-type CLDN1 or CLDN1 containing defined mutations indicated on the x-axis. Binding of monoclonal anti-CLDN1 antibodies (OM-7D3-B3 (A) and OM-8A9-A3 (B)) to mutant CLDN1 relative to binding to wild-type CLDN1 is shown (black bars). Proper expression of wild-type and mutant CLDN1 in transiently transfected Bosc cells was confirmed by flow cytometric analysis of HA-tag expression levels and anti-HA antibody (open bars) except for mutant I32A where the HA tag was absent and expression of CLDN1 was assessed. Binding of anti-HA antibody to HA of mutant CLDN1 relative to HA of wild-type CLDN1 is shown as internal control for the expression of mutant CLDN1 (open bars).

The interactions of the six monoclonal antibodies with a panel of CLDN1 mutants described by Cukierman and coworkers (Cukierman, 2009) were studied in order to further define the motif targeted by the antibodies. Using an alanine scanning mutagenesis approach, Cukierman and coworkers had identified seven residues in the CLDN1 first extracellular loop that are critical for entry of HCV isolates drawn from six different subtypes. Most of the critical residues belong to the motif W(30)-GLW(51)-C(54)-C(64), which is highly conserved among all human claudins (Cukierman, 2009). Using transiently transfected BOSC23 cells expressing wild-type and mutant CLDN1 molecules, the Applicants have demonstrated that replacement of amino acid residues by alanine at positions 30, 35, 49, 50, 51, 54, and 64 of CLDN1 drastically reduced binding of monoclonal antibody OM-7D3-B3, whereas the other mutations did not affect the interaction of antibodies (FIG. 18A).

Figure 18B:
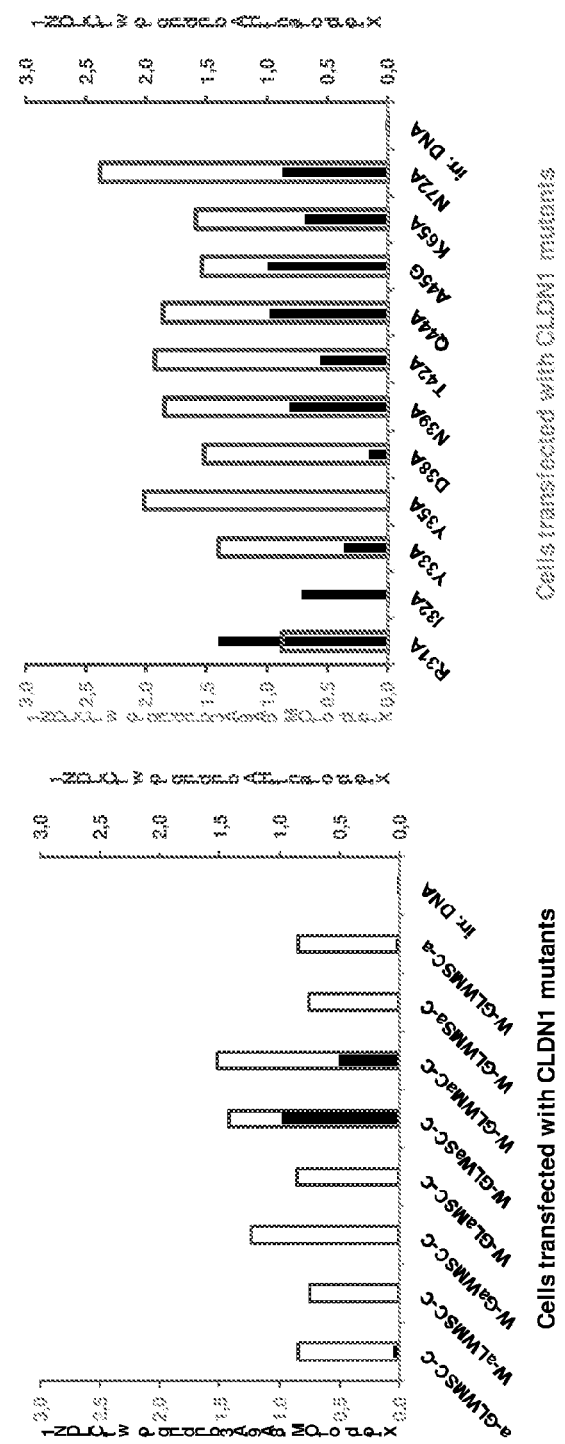

Previous studies have shown that residue I32 is important for entry (Evans, 2007) and the proximal D38 residue (Cukierman, 2009) was equally important for viral entry. Interestingly, mutagenesis of these residues still allowed partial binding of anti-CLDN1 antibodies (FIG. 18) suggesting that these residues play a less important role for anti-CLDN1-CLDN1 interaction. Furthermore, analysis of anti-CLDN1 binding to mutant CLDN1 demonstrate that residue Y35 appears to be recognized by monoclonal anti-CLDN1 antibodies (FIGS. 18A and B). Proper expression of wild-type and mutant CLDN1 in transiently transfected BOSC23 cells was confirmed by flow cytometry analysis of HA-tag expression levels and anti-HA antibody (FIG. 18AB) except for mutant I32A where the HA tag was absent (FIG. 18AB) and expression of CLDN1 was assessed by FACS analysis using an unrelated antibody directed against the non mutated CLDN1 C-terminal domain (mutant I32A: data not shown). A similar pattern was observed for antibody OM-8A9-A3 (FIG. 18B). These results suggest that the mAbs recognize conformation-dependent epitopes affected by the W(30)-GLW(51)-C(54)-C(64) motif which have been identified as essential co-residues for HCV entry (Cukierman, 2009).

Discussion

For the first time, monoclonal antibodies have been generated against the extracellular loops of Claudin 1 that potently cross-neutralize HCV infection from all major genotypes. Recognition is strongly dependent on conservation of the motif W(30)-GLW(51)-C(54)-C(64) of human CLDN1 extracellular loop 1. Whether this motif represents the epitope, or whether the mutations affecting recognition cause conformational changes that lead to loss of or masking of this epitope remains to be determined. Anti-CLDN1 antibodies cross-inhibit entry of HCV isolates in individual patients as well as entry of major HCV variants selected during liver transplantation using HCVpp bearing patient-derived envelope glycoproteins from four patients with HCV re-infection during liver transplantation.

A major limitation of current and evolving antiviral therapies targeting the virus is the rapid development of viral resistance. A major challenge for the development of antivirals and immunopreventive strategies is the high variability of the virus. HCV has a very high replication rate and the highly error prone viral polymerase allows for rapid production of minor viral variants called "quasispecies" that may outpace humoral and cellular immune response and result in viral isolates conferring viral resistance to conventional antiviral therapy (Aurora, 2009). Targeting essential host factors may represent a complementary alternative. If viral escape occurs, it will consist of different mechanisms and viral factors. The fact that anti-CLDN1 antibodies similarly inhibit HCV infection of viral isolates of all genotypes and quasispecies in individual patients suggests the absence of pre-existing variants or genotypes resistant to anti-CLDN1 antibodies.

By developing anti-CLDN1 antibodies efficiently cross-neutralizing HCV infection, the Applicants had demonstrated a proof-of-concept for CLDN1 as a target for novel antiviral strategies. Since HCV entry is the first step of virus-host interactions and a major target of host neutralizing responses, it represents a promising target for antiviral therapies that may complement ongoing efforts to block intracellular replication events with inhibitors of the HCV proteases and polymerase (Stamataki, 2008; Timpe and McKeating, 2008; Zeisel, 2008). The successful clinical development of entry inhibitors for other viral infections such as HIV (Este and Telenti, 2007) underlines the relevance of the viral entry step as a therapeutic or preventive target.

An important application of monoclonal antibodies may be the prevention of HCV re-infection following liver transplantation. A major current limitation of liver transplantation (LT) is the universal HCV re-infection of the graft followed by an accelerated course of HCV-induced liver disease (Brown, 2005). A prophylactic strategy for prevention of re-infection is lacking and interferon-based antiviral therapies have limited efficacy and tolerability in LT recipients (Brown, 2005). Due to viral evasion from host immune responses and the absence of preventive antiviral strategies, re-infection of the graft is universal and characterized by accelerated progression of liver disease (Brown, 2005). Using primary human hepatocytes and retroviral HCV pseudotypes bearing viral envelope glycoproteins derived from HCV-infected patients undergoing liver transplantation, the team of one of the Applicants has previously demonstrated that enhanced viral entry and escape from antibody-mediated neutralization are key determinants for selection of viral variants during HCV re-infection of the liver graft (Fafi-Kremer, 2009, submitted for publication).

In the present study, the Applicants have shown that anti-CLDN1 monoclonal antibodies efficiently inhibited HCV infection of primary human hepatocytes with isolates having escaped host cell immune response during liver transplantation. The efficient neutralization of viral variants having escaped the patient's neutralizing responses by a cross-neutralizing anti-CLDN1 antibody demonstrates that HCV entry is a viable target for antiviral strategies preventing re-infection of the graft. This finding is further supported by recent studies in a humanized mouse model for HCV infection, demonstrating that monoclonal anti-E2 and anti-CD81 antibodies were capable of neutralizing genetically diverse HCV isolates and protect against heterologous HCV quasispecies challenge (Meuleman, 2008; Law, 2008). Thus, administration of monoclonal cross-neutralization anti-CLDN1 antibodies, with or without concomitant antiviral therapy, may offer a viable and promising option to prevent HCV re-infection of the transplanted liver.

A potential limitation for the use of anti-receptor antibodies for prevention or treatment of HCV infection could be toxicity. Host cell factors have important functions which may be linked to mechanism of viral entry. Thus, antibodies binding to HCV entry factors may alter the function or expression of receptors resulting in side effects. Interestingly, no toxic effects were detected in a side-by-side analysis of cell viability based on MTT testing even at high doses of anti-CLDN1 (FIG. 16). In this regard, it is of interest to note that the Applicants have previously demonstrated that polyclonal anti-CLDN1 antiserum had no effect on tight junction permeability and integrity in polarized HepG2 hepatoma cells (Krieger, 2009, manuscript submitted). Although further studies are needed to address toxicity in vivo, the pilot toxicity studies performed by the Applicants in HCV permissive cells and human hepatocytes suggest that anti-CLDN1 antibodies may be well tolerated.

What is the mechanism of neutralization of HCV infection by monoclonal anti-CLDN1 antibodies? CLDNs are critical components of tight junctions and have a tetraspanin topology with four transmembrane domains, two extracellular and one intracellular loop, and N- and C-terminal cytoplasmic domains (Van Itallie and Anderson, 2006). CLDN1 extracellular loop 1 (EL1) has been shown to be required for HCV entry (Evans, 2007) and is involved in barrier function and contributes to pore formation between polarized cells (Krause, 2008). Mutagenesis studies in non-polarized HEK293T cells have demonstrated that CLDN1 enrichment at cell-cell contacts may be important for HCV entry (Cukierman, 2009). Using a variety of imaging and biochemical techniques, several laboratories have reported that CLDN1 associates with CD81. Most recent data of the Applicants laboratory, have shown that CLDN1 mediates HCV entry by forming a virus/co-receptor complex including HCV E2, CD81 and CLDN1, which is required for viral entry (see Example 3). The Applicants further demonstrated that anti-CLDN1 antibodies neutralize HCV infectivity by reducing E2 association with the cell surface and disrupting CD81-CLDN1 interactions (see Example 3).

Interestingly, whereas the magnitude of inhibition appeared to be similar for infection of Huh7.5.1 cells with HCVcc (FIG. 11) and HCVpp (FIG. 12), the magnitude of inhibition of HCVpp infection appeared to be more pronounced in primary human hepatocytes compared to Huh7.5.1 cells (FIG. 13-15 and data not shown). This may be due to the fact that expression of receptors or co-receptor complexes may be different in partially polarized primary human hepatocytes compared to non-polarized Huh7 hepatoma cell lines.

Figure 17:
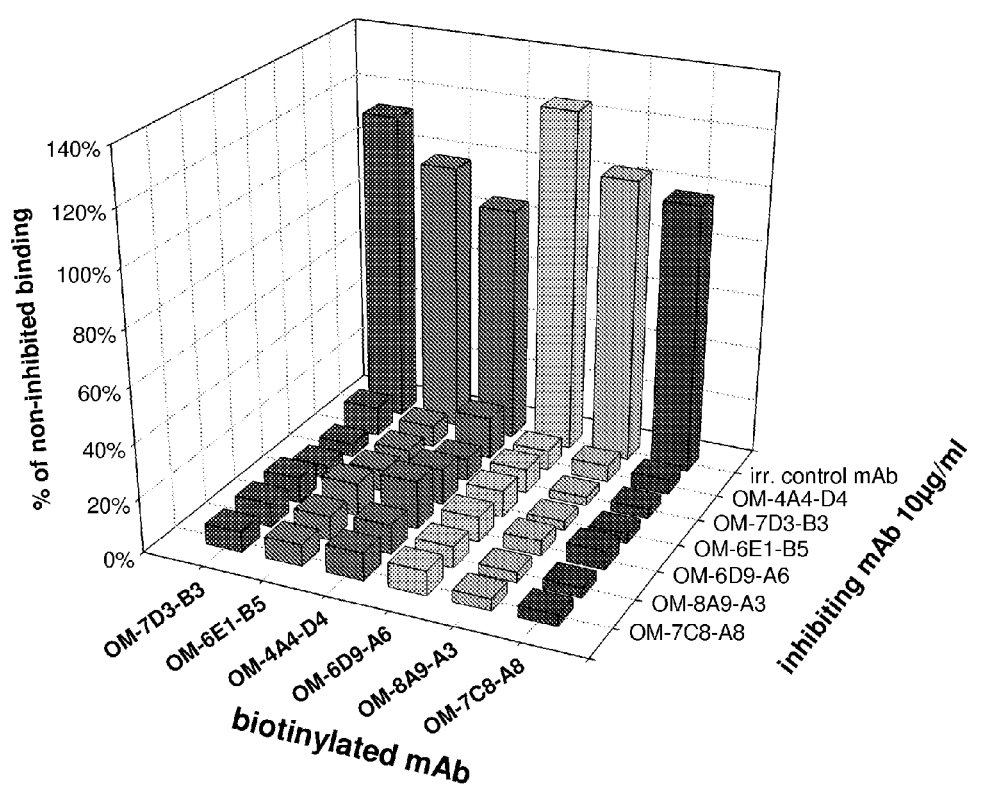
FIG. 17 is a set of graphs showing the cross-competition of two anti-CLDN1 monoclonal antibodies in binding and infection studies.
Figure 17:
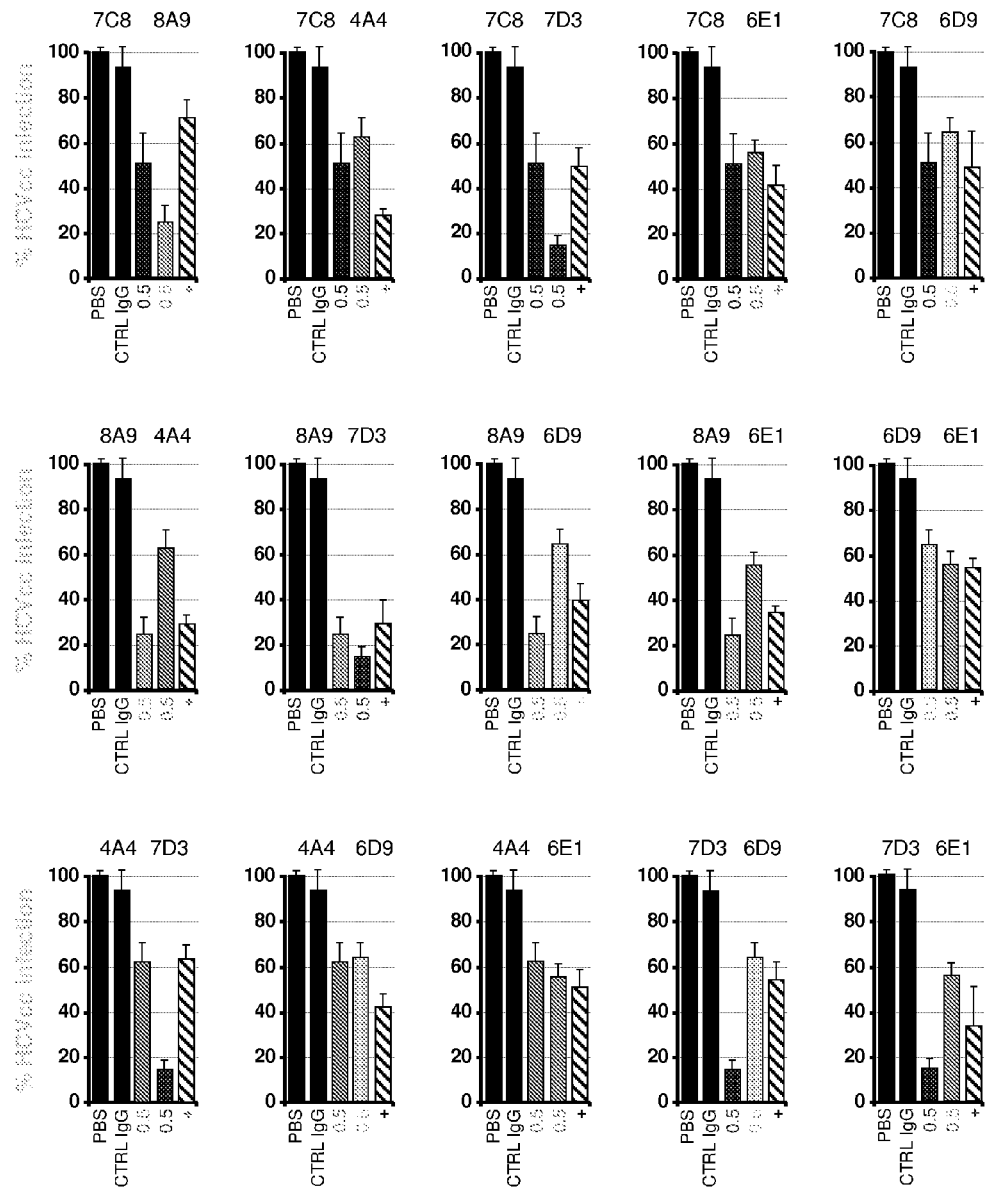

Cross-competition antibody binding and infection studies clearly showed that monoclonal antibodies targeted a closely related epitope domain (FIG. 17). Using a panel of well characterized CLDN1 mutants, the Applicants have demonstrated that the replacement of amino acids at positions 30, 35, 49, 50, 51, 54 and 64 of CLDN1 EL1 by alanine drastically reduced binding of monoclonal antibody OM-7D3-B3 to CLDN1, whereas the interaction of antibodies with other mutants was not affected at all or affected to a lesser extent (FIG. 19).

Figure 20:
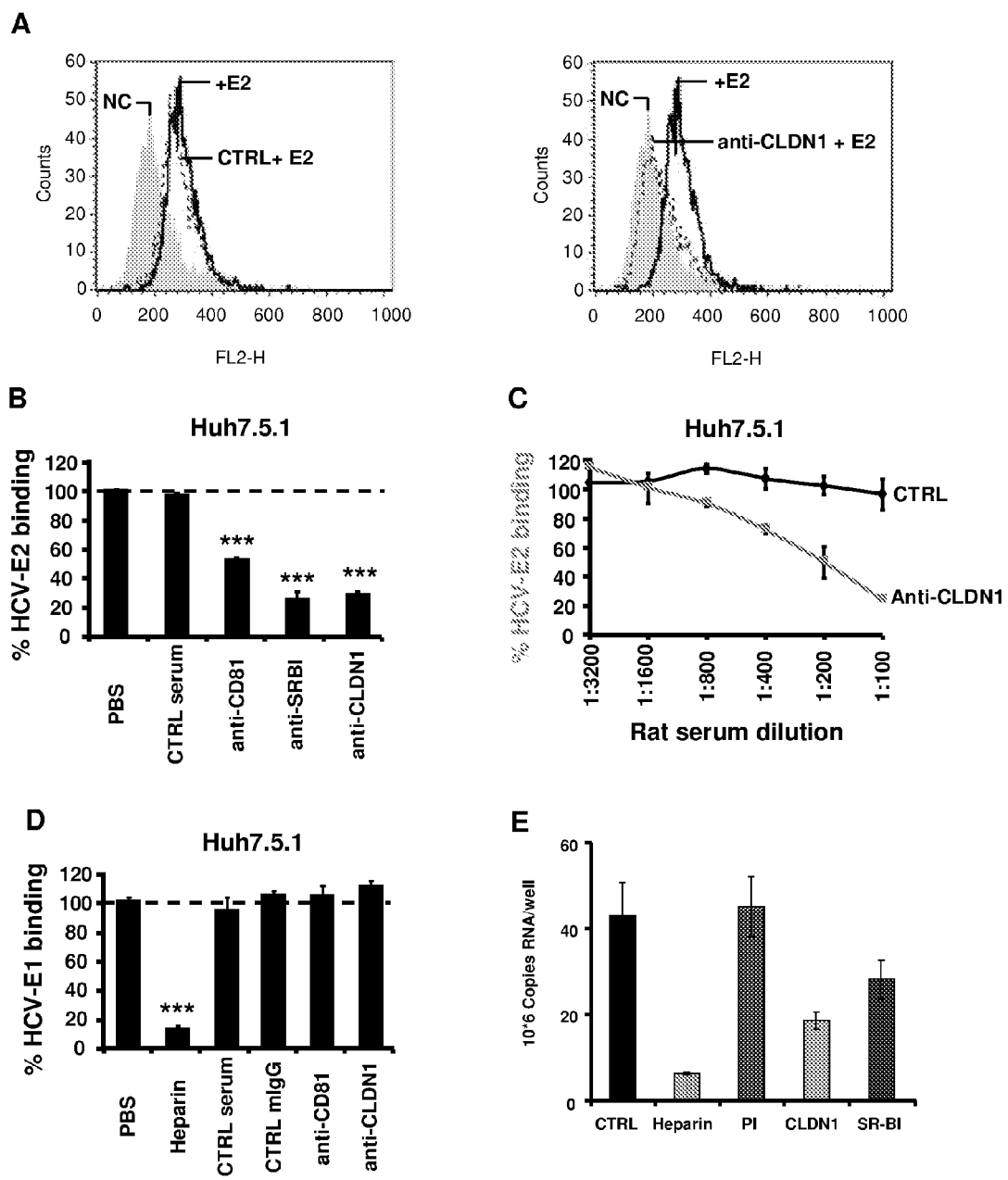
FIG. 20 is a set of graphs showing the dose-dependent inhibition of E2 binding to permissive cell lines by anti-CLDN1 antibodies. (A) Binding of recombinant E2 glycoprotein to permissive Huh7.5.1 cells. Huh7.5.1 cells were pre-incubated with control rat pre-immune serum (CTRL: left panel) or rat anti-CLDN1 antibodies (right panel) diluted 1/100 for 1 hour at room temperature. Binding of E2 was detected by flow cytometry. Cells incubated in the absence of antibody and E2 (PBS) served as negative control (NC—light shaded histograms). A representative experiment is shown. (B) Binding of recombinant E2 glycoprotein to permissive Huh7.5.1 cells. Huh7.5.1 cells were pre-incubated with rat anti-CD81, rat anti-SR-BI and rat anti-CLDN1 antibodies or control rat pre-immune serum (all diluted 1/100) for 1 hour at room temperature. Binding to E2 was detected by flow cytometry. Results are expressed as percent E2 binding in the absence of antibody (PBS). Mean±SD of four independent experiments performed in duplicate are shown. (C) Dose-dependent inhibition of E2 binding to Huh7.5.1 cells by anti-CLDN1. Huh7.5.1. cells were pre-incubated with different dilutions of polyclonal rat anti-CLDN1 (grey squares) antibodies or control rat pre-immune serum (black diamonds). Results are expressed as percent E2 binding in the absence of antibody. Mean±SD of four independent experiments performed in duplicate are shown. (D) Binding of recombinant E1 glycoprotein to permissive Huh7.5.1 cells. Huh7.5.1 cells were pre-incubated with heparin, mouse anti-CD81 (JS-81; 5 µg/mL), control (CTRL) mouse IgG (5 µg/mL), rat anti-CLDN1 (1/100), rat pre-immune serum (1/100) for 1 hour at room temperature. Binding of E1 was detected by flow cytometry. Results are expressed as percent E1 binding in the absence of antibody (PBS). Mean±SD of two independent experiments performed in duplicate are shown. Results are expressed as percentage E2 binding in the absence of antibody (PBS). Mean±SD of two independent experiments performed in duplicate are shown. ***P<0.0001 (t test). (E) Binding of HCVcc to permissive Huh7.5.1 cells. Huh7.5.1 cells were pre-incubated with heparin, rat anti-CLDN1, rat anti-SR-BI or control rat pre-immune serum (PI) (all diluted 1/100) for 1 hour at room temperature prior to incubation with HCVcc (Jc1 strain) which had been partially purified from cell culture supernatants using gradient ultracentrifugation. Following incubation with HCVcc, non bound HCVcc were removed by washing of cells with PBS. Binding of HCVcc was then quantified by RT-PCR of cell bound HCV RNA, which is indicated on the y axis.

These data suggest that mAbs recognize an epitope either present within the cluster of amino acid residues comprising W(30)-GLW(51)-C(54)-C(64) of the CLDN1 EL1 or an epitope that may become lost or masked through structural changes. In the former case, as these conserved amino acids are structurally not grouped together, it is likely that the recognized epitopes are conformation-dependent. This hypothesis is further supported by the finding that pre-incubation of antibodies with linear peptides encoding for amino acids of the CLDN1 EL1 were not able to revert antibody-mediated inhibition of infection (data not shown). Furthermore, anti-CLDN1 antibodies produced by genetic immunization did not show an easily detectable interaction with linear CLDN1 peptides as antigens in an ELISA (data not shown).

The identified residues in the CLDN1 first extracellular loop and targeted by the monoclonal antibodies have been shown to be critical for entry of HCV isolates drawn from six different subtypes (Cukierman, 2009). The fact that monoclonal anti-CLDN1 antibodies targeting this epitope efficiently cross-neutralize entry of HCV isolates from six different isolates further underline the relevance of these CLDN1 residues for HCV entry. It is of interest to note that alanine substitutions of these residues did not impair CLDN1 cell surface expression (Cukierman, 2009). Since polyclonal antibodies produced by the same approach have been shown to disrupt virus/co-receptor complex including HCV E2, CD81 and CLDN1 (Example 3), it is conceivable that the targeted amino acid residues in EL1 play a key role for the formation of a E2-CD81-CLDN1 co-receptor complex which is essential for viral entry. Further studies are underway to address this issue.

In conclusion, monoclonal antibodies that are dependent on the conservation of the W(30)-GLW(51)-C(54)-C(64) motif in CLDN1 EL1 have been produced that cross-neutralize HCV infection. These results define residues in CLDN1 EL1 which are crucial for HCV entry and are accessible for antibodies blocking HCV infection. Finally, the data suggest that targeting CLDN1 EL1 using monoclonal anti-CLDN1 antibodies constitutes a novel antiviral approach to prevent primary HCV infection, such as after liver transplantation and might also restrain virus spread in chronically infected patients.

Example 3

Mechanism of Action of Anti-CLDN1 Monoclonal Antibodies

Materials and Methods

Cell Lines. As described in Example 2. HEK293T/CLDN1+ cells (clone IIIA6) were obtained by stable transfection of HEK293T cells with a pcDNA3.1 vector encoding CLDN1 cDNA.

Antibodies. As described in Example 2. In addition, polyclonal rat anti-SR-BI or CD81 antibodies were obtained by genetic immunization as described (Zeisel, 2007). R-phycoerythrin-conjugated goat anti-rat IgG was from Jackson ImmunoResearch Laboratories, mouse IgG from Caltag, mouse anti-CD81 (JS-81) from BD Biosciences.

Cellular Binding of HCV envelope Glycoproteins and Infectious Virions. Production and binding of C-terminally truncated envelope glycoproteins E1 and E2 to target cells has been described (Haberstroh, 2008; Dreux, 2009). For the study of E2-entry factor interaction, CHO cells were transiently transfected with pcDNA3 based expression vectors encoding SR-BI; CD81 or CLDN1 (Barth, 2005). Expression of entry factors was assessed by flow cytometry using anti-receptor antibodies as described previously (Barth, 2005). For the study of envelope glycoprotein binding in the presence of anti-receptor antibodies, Huh7.5.1 cells (Zhong, 2005) were pre-incubated for 1 hour at room temperature with rat anti-SR-BI, anti-CLDN1, and anti-CD81 serum (1/100) or mouse anti-human CD81 (JS-81, 5 μg/mL) or control antibodies (1/100 or 5 μg/mL). Recombinant E2 (30 μL of concentrated cell culture supernatant) or E1 (10 μg/mL) was added to cells for 1 hour at room temperature. Following washing with PBS, bound envelope glycoproteins were detected using flow cytometry and human anti-E1 (IGH526; Haberstroh, 2008) or mouse anti-His (RGS-His, Qiagen) and PE-conjugated secondary antibodies (Dreux, 2009; Barth, 2008). For the study of binding of HCVcc to permissive Huh7.5.1 cells, Huh7.5.1 cells were pre-incubated with heparin, rat anti-CLDN1, rat anti-SR-BI or control rat pre-immune serum (PI) (all diluted 1/100) for 1 hour at room temperature prior to incubation with HCVcc (Jc1 strain) which had been partially purified from cell culture supernatants using gradient ultracentrifugation. Following incubation with HCVcc, non bound HCVcc were removed by washing of cells with PBS. Binding of HCVcc was then quantified by RT-PCR of cell bound HCV-RNA as described by Ploss et al. (2009).

Receptor Association using Fluorescence Resonance Energy Transfer (FRET). Homotypic and heterotypic interactions of CD81 and CLDN1 were analyzed as described (Harris, 2008; Mee, 2009). Briefly, HEK293T cells transduced to express AcGFP and DsRED tagged CD81 and CLDN1 were grown on glass coverslips and fixed in ice-cold methanol. The cells were imaged on a Zeiss meta head LSCM, with microscope settings optimized for each fluorescent protein to obtain the highest signal-to-noise ratio. For FRET analysis, the gradual acceptor photobleaching method of FRET was used, which entailed photobleaching the DsRED fluorophore gradually over time while monitoring AcGFP fluorescent intensity (Harris, 2008). After background and cross-talk correction, any increase in AcGFP intensity following DsRED photobleaching is due to FRET between proteins, implying a distance of less than 10 nm. The percentage FRET is defined as the number of pixels that display FRET over the total number of pixels analyzed at the plasma membrane of the cells (Harris, 2008). The intensity of AcGFP and DsRED tagged CD81 and CLDN1 (arbitrary fluorescence units/pixel) at the plasma membrane provides 500 to 1000 measurements per cell. The data from 10 cells were normalized and the localized expression was calculated.

Results

Anti-CLDN1 inhibits Binding of Envelope Glycoprotein E2 and Infectious Virions to HCV Permissive Cells in the Absence of CLDN1-E2 interaction. To investigate whether anti-CLDN1 antibodies could interfere with E2 binding to permissive cell lines, binding studies were performed using recombinant E1 and E2 glycoproteins in the presence of anti-receptor or control antibodies. As shown in FIG. 20B, anti-CD81, anti-CD81, and anti-SR-BI and anti-CLDN1 antibodies inhibited the binding of E2 to Huh7.5.1 cells. In contrast, pre-immune or unrelated control serum had no effect (FIG. 20A-C). Interestingly, the magnitude of inhibition of E2 binding to Huh7.5.1 cells (FIG. 20C) correlated with the magnitude of inhibition of HCV infection, suggesting that inhibition of binding of E2-cell surface interactions provides a mechanism of action for the neutralizing activity of the anti-CLDN1 antibodies. The relevance of these observations for infectious virions was further confirmed by binding studies using HCVcc (FIG. 20E). In contrast, E1 binding was not affected by anti-CLDN1 (FIG. 20D).

Figure 21:
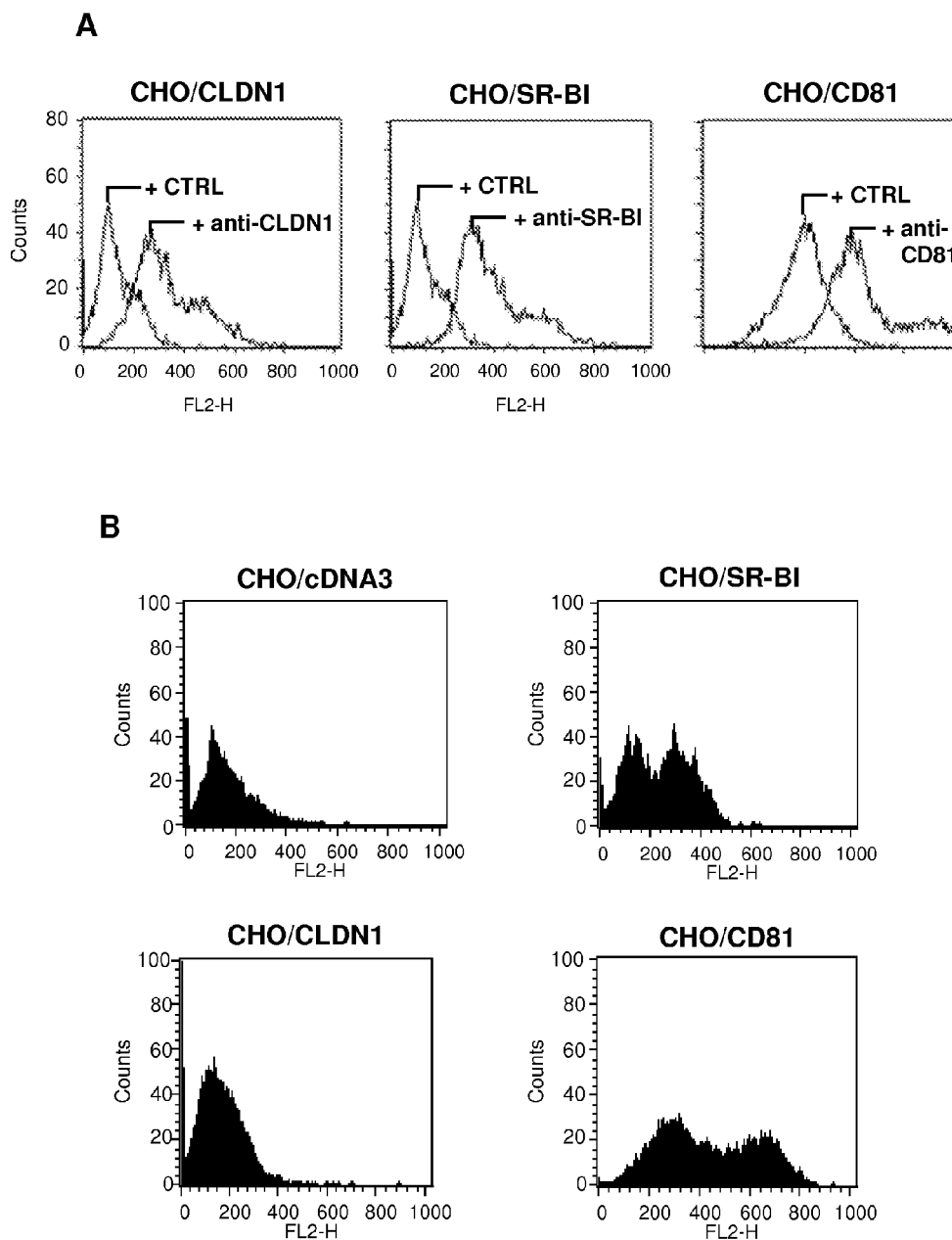
FIG. 21 is a set of graphs showing cellular binding of envelope glycoprotein E2 to CHO cells expressing CD81 and SR-BI but not cells expressing CLDN1. (A) Expression of human entry factors in transfected CHO cells. CHO cells were transfected with expression plasmids encoding human CLDN1, SR-BI or CD81 as described in Example 3. Transfected CHO cells were analyzed by flow cytometry using rat control (CTRL), rat anti-CLDN1 (left panel), rat anti-SR-BI (middle panel) or mouse control IgG and anti-CD81 (JS-81; right panel). (B) Binding of envelope glycoprotein E2 to CHO cells expressing human HCV entry factors. CHO cells were transfected with individual expression plasmids encoding human CLDN1, SR-BI or CD81 as indicated. Cellular E2 binding was analyzed by flow cytometry. A representative experiment performed in duplicate is shown.

To study whether antibody inhibition of E2 binding to permissive cell lines was attributable to CLDN1 interactions with E2, the Applicants have investigated whether CLDN1 was able to bind recombinant truncated glycoprotein E2. To address this question, CHO cells were engineered to express human CLDN1, SR-BI or CD81 (FIG. 21A). Cell surface expression of human CD81 or human SR-BI conferred E2 binding to CHO cells (FIG. 21B), whereas CLDN1 expression had no effect (FIG. 21B). These data suggest that CLDN1 does not interact directly with HCV envelope glycoprotein E2 and that antibody blocking of E2-cell surface interactions may be mediated by indirect mechanisms.

Figure 22:
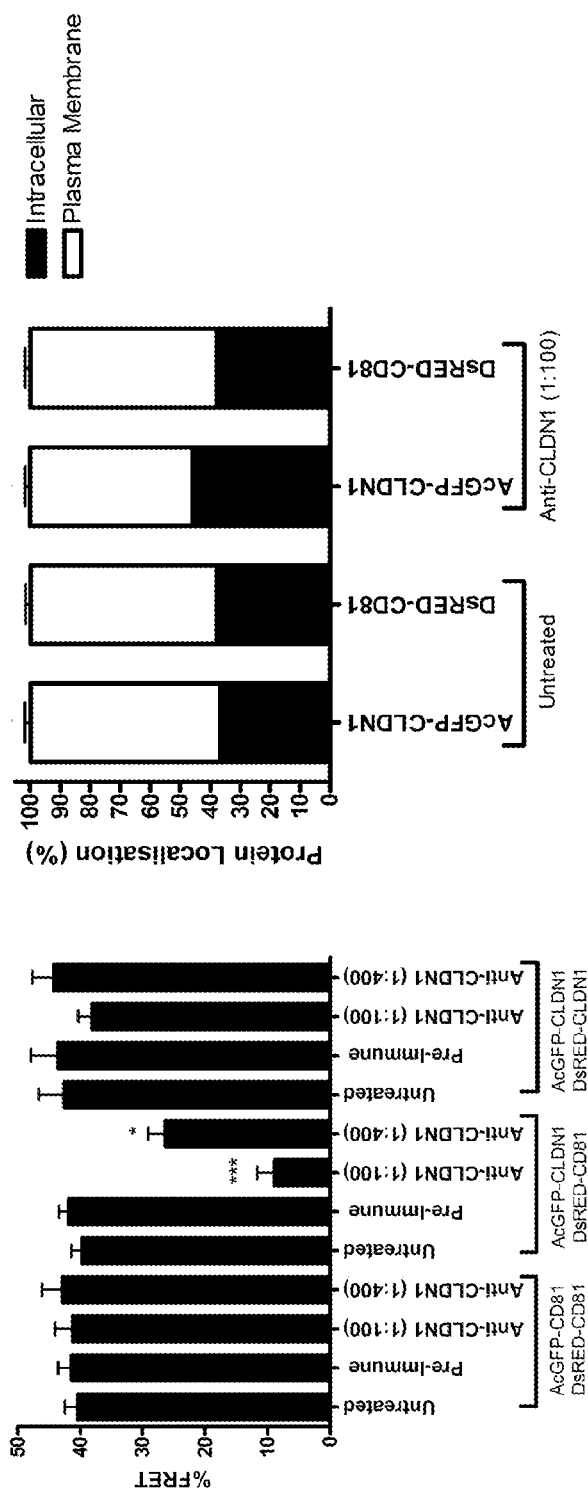
FIG. 22 is a set of two graphs showing anti-CLDN1 inhibition of CD81-CLDN1 co-receptor association using FRET analysis. HEK293T cells co-transfected to express AcGFP, CD81 and DsRED.CD81, AcGFP.CLDN1 and DsRED.CD81, or AcGFP.CLDN1 and DsRED.CLDN1 were seeded onto glass coverslips and treated with pre-immune or anti-CLDN1 sera for 1 hour. Cells were fixed, imaged by laser scanning confocal microscopy and FRET between AcGFP donor and DsRED acceptor proteins was measured. Percentage FRET is defined as the frequency of pixels demonstrating FRET relative to the total number of pixels analyzed at the plasma membrane of ten cells. *P<0.0001,  P<0.01 (t test). AcGFP.CLDN1 and DsRED.CLDN1 at intracellular (black) and plasma membrane (white) locations in untreated and anti-CLDN1 treated cells were quantified and the percentage of CLDN1 at each location determined.

Anti-CLDN1 Antibodies Inhibit CLDN1-CD81 Co-receptor Association(s). Since anti-CLDN1 antibodies inhibit E2 binding to HCV permissive cells in the absence of a direct CLDN1-E2 interaction (FIG. 21B), the Applicants have hypothesized that anti-CLDN1 antibodies may interfere with CD81-CLDN1 co-receptor complexes. To assess whether anti-CLDN1 antibodies alter CLDN1-CD81 association, HEK293T cells were transfected to express Ac-GFP-CD81 and DsRED-CD81 or AcGFP-CLDN1 and DsRED-CD81 or AcGFP-CLDN1 and DsRED-CLDN1, incubated with pre-immune and anti-CLDN1 serum (1/100 and 1/400) and co-receptor interaction(s) analyzed by FRET. As shown in FIG. 22, anti-CLDN1 antibodies significantly reduced FRET between CD81 and CLDN1 in a dose-dependent manner. Pre-incubation of cells with control serum did not modify CD81-CLDN1 co-receptor interaction(s). Inhibition of CD81-CLDN1 co-receptor interaction was specific as shown by the unchanged FRET between CD81-CD81 and CLDN1-CLDN1 following pre-incubation with anti-CLDN1 serum. Taken together, these data suggest that anti-CLDN1 antibodies interfere with CD81-CLDN1 heterodimer association.

Discussion

CLDN1 is an essential co-factor conferring HCV entry. However, the precise role of CLDN1 in the multi-step entry process remains poorly understood. Using transfected CHO cells expressing human HCV entry factors, the Applicants have demonstrated that in contrast to CD81 and SR-BI, CLDN1 does not directly interact with envelope glycoprotein E2 at the cell surface. Using a FRET-base system to study CD81-CLDN1 co-receptor association, neutralizing anti-CLDN1 antibodies of the invention were shown to specifically disrupt CD81-CLDN1 FRET (FIG. 22).

These data suggest that antibodies targeting CLDN1 neutralize HCV infectivity by reducing E2 associations with the cell surface and reducing CD81-CLDN1 interactions. CD81-CLDN1 co-receptor complexes are critical for HCV entry and CLDN1 may potentiate CD81 association with HCV particles via E2 interactions. They also provide a new avenue for antiviral strategies targeting E2-CD81-CLDN1 interactions.

Example 4

Anti-CLDN1 Monoclonal Antibodies Inhibit HCV Cell-Cell Transmission and Block Viral Dissemination when Added Post-Infection Materials and Methods Cell-Cell Transmission Assay. Huh7.5.1 cells were provided by Dr. F. Chisari (The Scripps Research Institute, USA; Zhong, 2005) and were cultured as described (Zeisel, 2007; Barth, 2008; Dimitrova, 2008). Huh7 GFP cells were provided by Dr. Patel (University of Glasgow, UK; Witteveldt, 2009). Huh7 derived cell lines had been obtained by transduction with a retrovirus vector carrying enhanced green fluorescent protein (EGFP), followed by selection in medium supplemented with 300 µg G418/mL (Witteveldt, 2009). To detect cell-cell transmission of HCV, freshly electroporated Huh7.5.1 cells were seeded and incubated for a 24 hour period, and then washed with medium to remove residual cell-surface bound HCV before adding the EGFP-expressing recipient cells with 10 µg/mL anti-CLDN1 antibodies. The co-cultured cells were grown to confluency, trypsinized, fixed with 1% paraformaldehyde and permeabilized with 0.1% saponin for FACS analysis. The cells were stained using mouse anti-core antibody followed by a phycoerythrin (PE)-conjugated secondary antibody for FACS analysis as described previously for SR-BI (Barth, 2006; Barth, 2008).

Results and Discussion

In general, viruses can disseminate within a host by two mechanisms including release of cell-free virions and direct passage between infected and uninfected cells. Direct cell-cell transfer is considered to be more rapid and efficient than cell-free spread because it obviates rate-limiting early steps in the virus life cycle, such as virion attachment. Moreover, cell-cell transfer of viral infectivity may allow viruses to evade elements of the immune response, such as neutralizing antibodies.

Recent studies have shown that HCV infection of hepatoma cells results in focal areas of infection that are potentiated by cell-cell contact, suggesting localized transmission between adjacent cells. Indeed, using labelled producer or recipient cells, two laboratories have demonstrated that HCV can be transmitted in vitro by both cell-free virus infection and direct transfer between cells, the latter offering a novel route for evading neutralizing antibodies (Timpe, 2008; Witteveldt, 2009).

To assess the ability of anti-CLDN1 monoclonal antibodies to inhibit cell-to-cell transmission, an HCV cell-to-cell transmission assay was established based on labelled recipient cells expressing green fluorescence protein (GFP). In this assay, HCV producer cells are co-cultured with GFP-labelled recipient cells in the presence or absence of anti-receptor antibodies. By blocking cell-free virus transmission with anti-CD81 antibodies (Timpe, 2008; Witteveldt, 2009), this assay allows to study the specific effect of antivirals on cell-cell transmission by quantifying HCV+, GFP+ recipient cells in FACS analysis.

Figure 23:
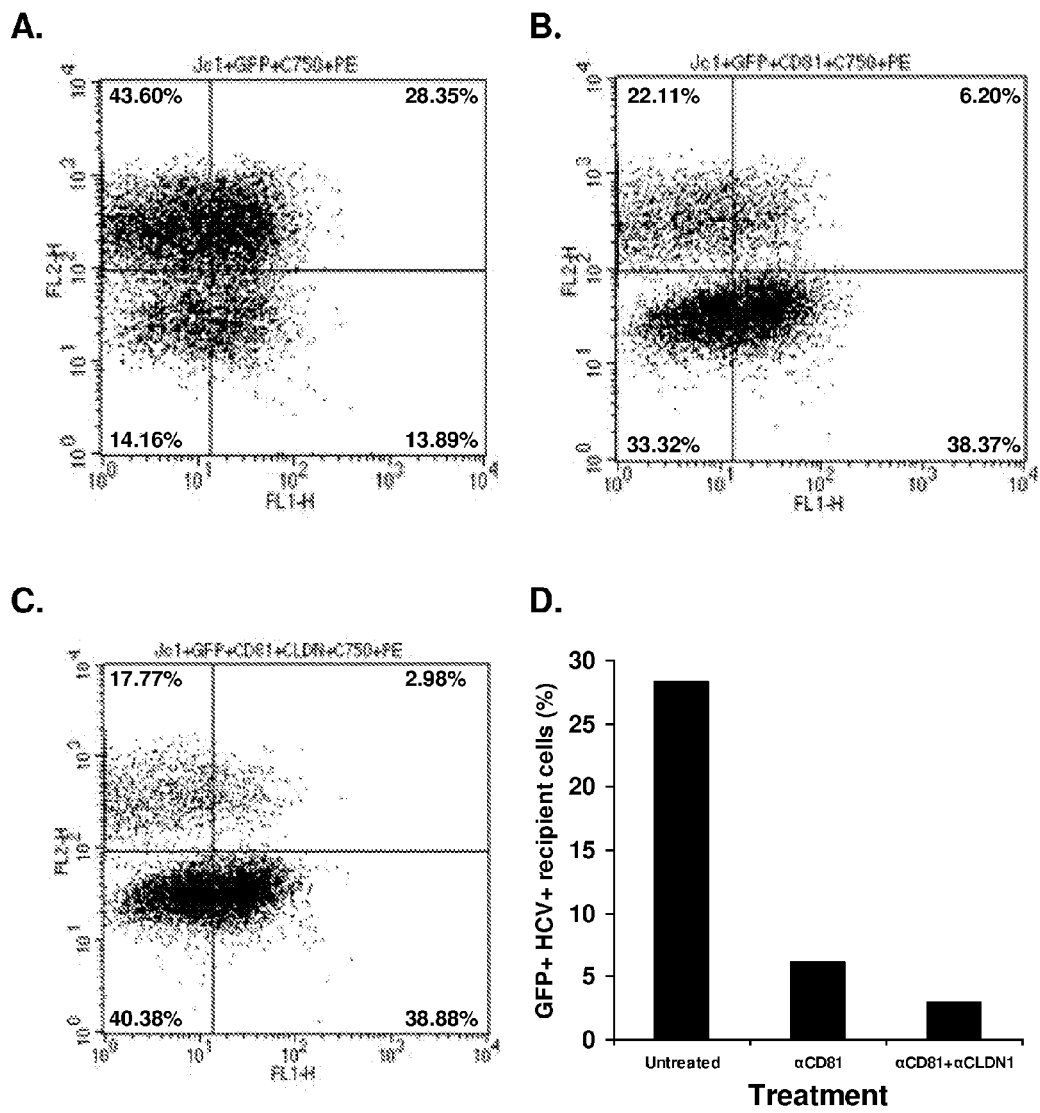
FIG. 23 is a set of graphs showing the inhibition of HCV cell-to-cell transmission by an anti-CLDN1 monoclonal antibody. Jc1 electroporated Huh7.5.1 producer cells were co-cultured for 24 hours with Huh7.5 GFP+ recipient cells in the absence of antibodies (A) or in the presence of anti-CD81 (10 mg/mL) antibody to block HCV cell-free transmission (B) or in the presence of anti-CD81 and anti-CLDN1 to block HCV cell free and cell-to-cell transmission (C). In each panel, the lower quadrants contain uninfected cells (lower left represents GFP− HCV− cells, lower right represents GFP+HCV− cells); the upper left represents GFP− HCV+ infected producer cells; and the upper right represents newly infected GFP+HCV+ recipient cells. In the dot plot, FL1-height (FL1-H) represents the fluorescence intensity of GFP and FL2-height (FL2-H) represents the fluorescence intensity of anti-core antibodies/PE (A-C). The relative frequency of GFP+ HCV+ recipient cells under the different treatments is depicted in (D). Results of a representative experiment are shown. Incubation of cells with rat isotype control antibodies was shown to have no effect on the level of HCV infection (data not shown).

Following a 24 hour co-culture of producer and recipient cells in the absence of antibodies (or control antibodies), 43.6% of all cells to correspond HCV+ GFP+ recipient cells (FIG. 23A). When blocking cell-free transmission by anti-CD81 antibodies (FIG. 23B), the number of HCV GFP+ recipient cells decreased to 6.20%. These cells correspond to cells exclusively infected by cell to cell transmission as shown previously by two other laboratories (Timpe, 2008; Witteveldt, 2009) and the laboratory of the Applicants (Baumert, unpublished observations). As shown in FIG. 23C, anti-CLDN1 monoclonal antibodies markedly reduced the number of HCV+, GFP+ recipient cells. Addition of anti-CLDN1 monoclonal antibody 7D3 reduced the percentage of HCV infected GFP+ recipient cells from 6.20% to 2.98%, suggesting that the anti-CLDN1 monoclonal antibody was able to reduce infection by cell-cell transmission by more than 50%. In contrast, isotype control antibodies had no effect (data not shown). These results indicate that anti-CLDN1 monoclonal antibodies inhibit HCV cell-to-cell transmission.

Figure 24:
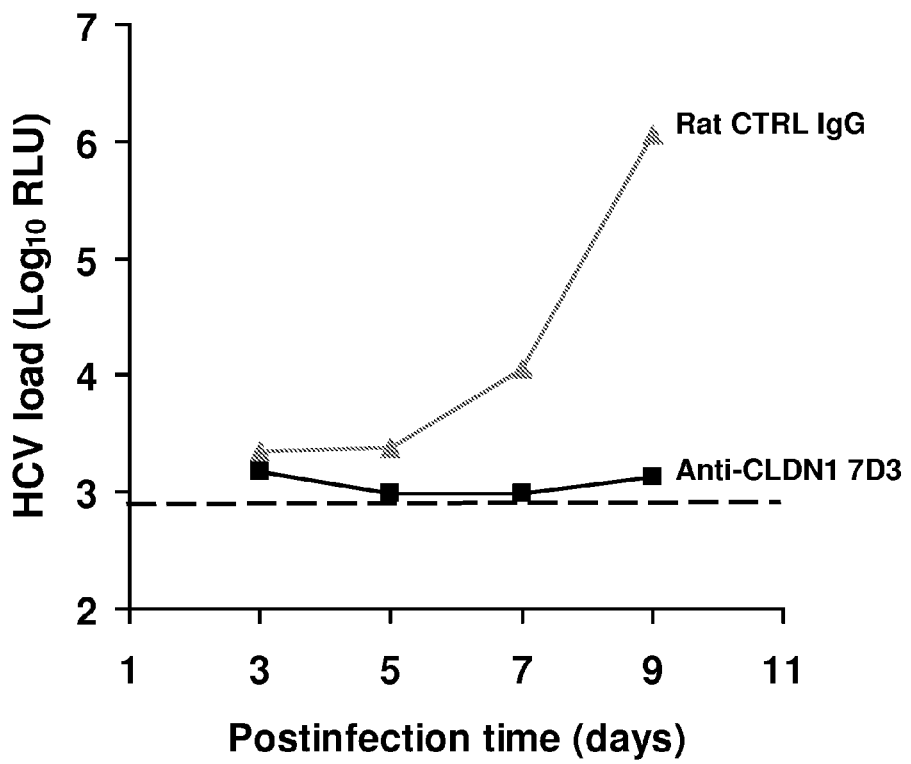
FIG. 24 is a graph showing the inhibition of HCV infection by an anti-CLDN1 monoclonal antibody (7D3) added post-infection. Huh7.5.1 cells were infected with HCVcc Luc-Jc1. Four hours post-infection, the anti-CLDN1 monoclonal antibody (7D3) or a rat isotype control monoclonal antibody (50 µg/mL) were added to cells. HCV infection was quantified by luciferase reporter expression on days 3, 5, 7 and 9 post-infection and is depicted as viral load ($Log_{10}$ RLU). Medium was changed every 2 days with replacement of fresh antibodies (50 µg/mL). The threshold for positive detection of viral load in this assay is 800 RLU (dotted line). Results of a representative experiment are shown. Values are means of duplicates. Abbreviations: RLU—relative light units.

To confirm the relevance of this finding for viral spread in an infectious tissue culture system, the Applicants have performed time course experiments in Huh7.5.1 cells. To study the effect of monoclonal anti-CLDN1 antibodies on viral spread, the anti-CLDN1 monoclonal antibody OM-7D3 was added 4 hours post-infection of cells with cell-free virus. As shown in FIG. 24, the anti-CLDN1 monoclonal antibody efficiently inhibited viral spread. Whereas incubation of Huh7.5.1 cells post-infection with isotype control antibodies resulted in a time-dependent increase of viral load over a time period of 7 days (>$10^6$ relative light units), addition of anti-CLDN1 post-infection resulted in low-levels of viral load close to the detection limit (approximately $10^3$ relative light units). These data further indicate the relevance of the effect of anti-CLDN1 antibodies on cell-cell transmission of viral spread in an infectious cell culture system and suggest that the inventive anti-CLDN1 monoclonal antibodies may not only be useful in prevention of HCV infection but also in the control of chronic viral infection.

References

R. Aurora et al., J. Clin. Invest., 2009, 119: 225-236.
H. Barth et al., J. Biol. Chem., 2003, 278: 41003-41012.
H. Barth et al., J. Virol., 2005, 79: 5774-5785.
H. Barth et al., J. Virol., 2008, 82: 3466-3479.
B. Bartosch et al., J. Exp. Med., 2003, 197: 633-642.
K. J. Blight et al., J. Virol., 2002, 76: 13001-13014.
R. S; Brown, Nature, 2005, 436: 973-978
M. T. Catanese et al., J. Virol., 2007, 81: 8063-8071
F. V. Chisari, Nature, 2005, 435: 930-932
L. Cocquerel et al., J: Gen. Virol., 2006, 87: 1075-1084
A. Codran et al., J. Gen. Virol., 2006, 87: 2583-2593.
L. Cukierman et al., J. Virol., 2009, 83: 5477-5484.
P. David et al., Hum. Exp. Toxicol., 1998, 17: 544-553.
M. C. Dimitrova et al., Proc. Natl. Acad. Sci. USA, 2008, 105: 16320-16325.
M. Dreux et al., PLoS Pathog 2009; 5:e1000310.
J A. Este and A. Telenti, Lancet, 2007, 370: 81-88.
M. J. Evans et al., Nature, 2007, 446: 801-805
S. Fafi-Kremer et al., "Escape from antibody-mediated neutralization and viral entry are key determinants for hepatitis C virus re-infection in liver transplantation", 2009, submitted for publication.
P. Farci et al., Proc. Natl. Acad. Sci. USA, 2006, 103: 8475-5480.
J. J. Feld et al., Nature, 2005, 436: 967-972
J. T. Grove et al., J. Virol., 2007, 81: 3162-3169
A. Haberstroh et al., Gastroenterology, 2008, 135: 1719-1728.
H. J. Harris et al., J. Virol., 2008, 82: 5007-5020.
J. H. Hoofnagle, Hepatology, 2002, 36: S21-S29
M. Hsu et al., Proc. Natl. Acad. Sci. USA, 2003, 100: 7271-727
S. B. Kapadia et al., J. Virol., 2007, 81: 374-383
T. Kato et al., J. Virol., 2007, 81: 4405-4411
G. Koutsoudakis et al., J. Virol, 2006, 80: 5308-5320.
G. Krause et al., Biochim. Biophys. Acta, 2008, 1778: 631-645.
S E. Krieger et al., "Inhibition of hepatitis C virus infection by anti-claudin antibodies is mediated by neutralization of E2-CD81-Claudin 1 association(s)", 2009, submitted for publication.
L. Lan et al., J. Immunol., 2008, 181: 4926-4935.
G. M. Lauer et al., N. Engl. J. Med., 2001, 345: 41-52
D. Lavillette et al., Hepatology, 2005, 41: 265-274.
M. Law et al., Nature Med., 2008, 14: 25-27.
J. W. Lee et al., Gynecol. Oncol., 2005, 97: 53-59
B. D. Lindenbach et al., Science, 2005, 309: 623-626.
B. D. Lindenbach et al., Proc. Natl. Acad. Sci. USA, 2006, 103: 3805-3809
J. Lorhmann et al., Curr. Drug Disc., 2003, October, 17-21.
C. J. Mee et al., J. Virol., 2009, 83: 6211-6221.
P. Meuleman et al., Hepatology, 2008, 48: 1761-1768.
S. Morohashi et al., Int. J. Mol. Med., 2007, 20: 139-143
T. Mosmann, J. Immunol., 1983, 65: 55-63.
Pawlotsky, Trends Microbiol., 2004, 12: 96-102
W S. Pear et al., Proc. Natl. Acad. Sci. USA., 1993, 90: 8392-8396.
J M. Pestka et al., Proc. Natl. Acad. Sci. USA., 2007, 104: 6026-6030.
T. Pietschmann et al., Proc. Natl. Acad. Sci. USA, 2006, 103: 7408-7413.
P. Pileri et al., Science, 1998, 282: 938-941
A. Ploss et al., Nature, 2009, 457: 882-886
K. A. Powers et al., Liver Transpl., 2006, 12: 207-216
S C. Ray et al., J. Exp. Med., 2005, 201: 1753-1759.
M. B. Resnick et al., Mod. Pathol., 2005, 18: 511-518
L. B. Seeff, Semin. Gastrointest., 1995, 6: 20-27.
L. B. Seeff and J. H. Hoofnagle, Hepatology, 2002, 36: 1-2
E. Scarselli et al., EMBO J., 2002, 21: 5017-5025
G. M. Sheeban et al., Hum. Pathol., 2007, 38: 564-569
G. Sobel et al., Hum. Pathol., 2005, 36: 162-169
Z. Stamataki et al., Clin. Liver Dis., 2008, 12: 693-712.
D. Steinmann et al., J. Virol., 2004, 78: 9030-9040.
M. Timpe and J A. McKeating, Gut, 2008, 57: 1728-1727.
J. M. Timpe et al., Hepatology, 2008, 47: 17-24.
D M. Tscherne et al., J. Virol., 2006, 80: 1734-1741.
L. Uebelhoer et al., PLoS Pathog, 2008, 4: e1000143.
C M. Van Itallie and J M. Anderson, Annu. Rev. Physiol., 2006, 68: 403-429.
T. Wakita et al., Nat. Med., 2005, 11: 791-796.
J. Witteveldt et al., J. Gen. Virol., 2009, 90(Pt 1): 48-58.
M. Yi et al., Proc. Natl. Acad. Sci. USA, 2006, 103: 2310-2315
M. B. Zeisel et al., Hepatology, 2007, 46: 1722-1731.
M B. Zeisel et al., "Hepatology, 2008, 48: 299-307.
J. Zhong et al., Proc. Natl. Acad. Sci. USA, 2005, 102: 9294-9299.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A hybridoma cell line deposited at the DSMZ on Jul. 29, 2008 under an Accession Number selected from the group consisting of DSM ACC2931, DSM ACC2932, DSM ACC2933, DSM ACC2934, DSM ACC2935, DSM ACC2936, DSM ACC2937, and DSM ACC2938.

2. A monoclonal antibody secreted by a hybridoma cell line deposited at the DSMZ on Jul. 29, 2008 under an Accession Number selected from the group consisting of DSM ACC2931, DSM ACC2932, DSM ACC2933, DSM ACC2934, DSM ACC2935, DSM ACC2936, DSM ACC2937, and DSM ACC2938, or a biologically active fragment thereof that binds Claudin 1 extracellular domain.

3. The monoclonal antibody or biologically active fragment thereof according to claim 2, wherein the monoclonal antibody or biologically active fragment binds to an epitope comprising the conserved motif W(30)-GLW(51)-C(54)-C(64) in Claudin 1 first extracellular loop.

4. The monoclonal antibody or biologically active fragment thereof according to claim 2, wherein the monoclonal antibody or biologically active fragment thereof does not bind to rodent Claudin 1 but binds to non-human primate Claudin 1.

5. The monoclonal antibody or biologically active fragment thereof according to claim 2, wherein the monoclonal antibody is humanized, de-immunized or chimeric.

6. A monoclonal antibody comprising the complementary determining regions (CDRs), or portions thereof, derived from a monoclonal antibody secreted by a hybridoma cell line deposited at the DSMZ on Jul. 29, 2008 under an Accession Number selected from the group consisting of DSM ACC2931, DSM ACC2932, DSM ACC2933, DSM ACC2934, DSM ACC2935, DSM ACC2936, DSM ACC2937, and DSM ACC2938, or a biologically active fragment thereof that binds Claudin 1 extracellular domain.

7. The monoclonal antibody or biologically active fragment thereof according to claim 6, wherein the monoclonal antibody is humanized, de-immunized or chimeric.

8. The monoclonal antibody or biologically active fragment thereof according to claim 2, wherein the monoclonal antibody or fragment thereof inhibits:
binding of HCV envelope glycoprotein E2 or infectious virions to HCV permissive cell lines,
CD81-Claudin-1 association or associations, and/or
HCV cell-to-cell transmission and viral dissemination.

9. The monoclonal antibody or biologically active fragment thereof according to claim 2, wherein the monoclonal antibody, or fragment thereof, is attached to a detectable moiety or a therapeutic agent.

10. A method for treating HCV infection or a HCV-related disease in a subject in need thereof, the method comprising administering to the subject an effective amount of the monoclonal antibody or biologically active fragment thereof according to claim 2.

11. A method for blocking HCV entry into at least one cell of a subject, the method comprising administering to the subject an effective amount of the monoclonal antibody or biologically active fragment thereof according to claim 2.

12. The method according to claim 10, wherein treating HCV infection or a HCV-related disease in the subject comprises inhibiting HCV infection in the subject.

13. The method according to claim 12, wherein inhibiting HCV infection comprises inhibiting HCV infection by the entire quasispecies population present in the HCV chronically infected subject.

14. The method according to claim 10, wherein the HCV infection or HCV-related disease is due to HCV of a genotype selected from the group consisting of genotype 1, genotype 2, genotype 3, genotype 4, genotype 5 and genotype 6.

15. The method according to claim 12, wherein the HCV infection is due to HCV of a genotype selected from the group consisting of genotype 1, genotype 2, genotype 3, genotype 4, genotype 5 and genotype 6.

16. The method according to claim 14, wherein the HCV infection or HCV-related disease is due to HCV of a subtype selected from the group consisting of subtype 1a, subtype 1b, subtype 2a, subtype 2b, subtype 2c, subtype 3a, subtype 4a-f, subtype 5a, and subtype 6a.

17. The method according to claim 15, wherein the HCV infection is due to HCV of a subtype selected from the group consisting of subtype 1a, subtype 1b, subtype 2a, subtype 2b, subtype 2c, subtype 3a, subtype 4a-f, subtype 5a, and subtype 6a.

18. A method for reducing the likelihood of HCV re-infection and recurrence in a liver transplantation subject, the method comprising administering to the subject an effective amount of the monoclonal antibody or biologically active fragment thereof according to claim 2.

19. A pharmaceutical composition comprising an effective amount of a monoclonal antibody or biologically active fragment thereof according to claim 2, and at least one pharmaceutically acceptable carrier or excipient.

20. The pharmaceutical composition according to claim 19 further comprising at least one anti-viral agent.

21. The pharmaceutical composition according to claim 20; wherein the anti-viral agent is selected from the group consisting of interferons, rabivirin, anti-hepatitis C virus monoclonal antibodies, anti-hepatitis C virus polyclonal antibodies, RNA polymerase inhibitors, protease inhibitors, IRES inhibitors, helicase inhibitors, antisense compounds, ribozymes, and any combination thereof.

22. A kit for the detecting Claudin-1 in a biological sample comprising a monoclonal antibody, or biologically active fragment thereof, according to claim 2, wherein the monoclonal antibody or fragment thereof is attached to a detectable moiety.

* * * * *

UNITED STATES PATENT AND TRADEMARK OFFICE
CERTIFICATE OF CORRECTION

PATENT NO. : 8,518,408 B2  
APPLICATION NO. : 13/119233  
DATED : August 27, 2013  
INVENTOR(S) : Baumert et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 234 days.

Signed and Sealed this  
Third Day of February, 2015

Michelle K. Lee  
*Deputy Director of the United States Patent and Trademark Office*

SEQUENCE LISTING

<160> NUMBER OF SEQ ID NOS: 9

<210> SEQ ID NO 1
<211> LENGTH: 20
<212> TYPE: PRT
<213> ORGANISM: Hepatitis C virus -continued

```
<400> SEQUENCE: 1

Asn Ser Ser Ile Val Tyr Glu Ala Glu Asp Met Ile Met His Thr Pro
1               5                   10                  15

Gly Cys Val Pro
            20

<210> SEQ ID NO 2
<211> LENGTH: 20
<212> TYPE: PRT
<213> ORGANISM: Hepatitis C virus

<400> SEQUENCE: 2

Asn Ser Ser Ile Val Tyr Glu Ala Glu Asp Met Ile Met His Thr Pro
1               5                   10                  15

Gly Cys Val Pro
            20

<210> SEQ ID NO 3
<211> LENGTH: 20
<212> TYPE: PRT
<213> ORGANISM: Hepatitis C virus

<400> SEQUENCE: 3

Asn Ser Ser Ile Val Tyr Glu Thr Val Asp Met Ile Met His Thr Pro
1               5                   10                  15

Gly Cys Val Pro
            20

<210> SEQ ID NO 4
<211> LENGTH: 29
<212> TYPE: PRT
<213> ORGANISM: Hepatitis C virus

<400> SEQUENCE: 4

Glu Thr Thr Val Ser Gly Gly Ala Ala Ala Lys Asp Val Phe Arg Phe
1               5                   10                  15

Ala Gly Ile Phe Ser Thr Gly Pro Ala Gln Glu Ile Lys
            20                  25

<210> SEQ ID NO 5
<211> LENGTH: 10
<212> TYPE: PRT
<213> ORGANISM: Hepatitis C virus

<400> SEQUENCE: 5

Tyr Ile Val Gln Leu Phe Leu Leu Leu Ala
1               5                   10

<210> SEQ ID NO 6
<211> LENGTH: 29
<212> TYPE: PRT
<213> ORGANISM: Hepatitis C virus

<400> SEQUENCE: 6

Glu Thr Thr Val Ser Gly Gly Ala Ala Ala Lys Asp Val Phe Arg Phe
1               5                   10                  15

Thr Gly Ile Phe Ser Ser Gly Pro Thr Gln Asn Ile Lys
            20                  25

<210> SEQ ID NO 7
<211> LENGTH: 10
<212> TYPE: PRT
<213> ORGANISM: Hepatitis C virus
```

-continued

```
<400> SEQUENCE: 7

Tyr Ile Val Leu Leu Phe Leu Leu Leu Ala
1               5                   10

<210> SEQ ID NO 8
<211> LENGTH: 29
<212> TYPE: PRT
<213> ORGANISM: Hepatitis C virus

<400> SEQUENCE: 8

Glu Thr Thr Val Ser Gly Gly Ala Ala Ala Arg Asp Val Phe Arg Phe
1               5                   10                  15

Ala Gly Ile Phe Ser Thr Gly Pro Ala Gln Glu Ile Lys
            20                  25

<210> SEQ ID NO 9
<211> LENGTH: 10
<212> TYPE: PRT
<213> ORGANISM: Hepatitis C virus

<400> SEQUENCE: 9

Tyr Ile Val Leu Leu Phe Leu Leu Leu Ala
1               5                   10
```